United States Patent
Hassan et al.

(10) Patent No.: US 12,016,899 B2
(45) Date of Patent: Jun. 25, 2024

(54) COMPOSITIONS COMPRISING SEL1-DERIVED PEPTIDES AND METHODS OF TREATMENT/PREVENTION OF EXCESS OXALATE LEVELS AND ASSOCIATED CONDITIONS/DISEASES THEREWITH

(71) Applicant: The University of Chicago, Chicago, IL (US)

(72) Inventors: Hatim A. Hassan, Chicago Ridge, IL (US); Donna Arvans, Chicago, IL (US)

(73) Assignee: The University of Chicago, Chicago, IL (US)

( * ) Notice: Subject to any disclaimer, the term of this patent is extended or adjusted under 35 U.S.C. 154(b) by 0 days.

(21) Appl. No.: 17/260,690

(22) PCT Filed: Jul. 18, 2019

(86) PCT No.: PCT/US2019/042416
§ 371 (c)(1),
(2) Date: Jan. 15, 2021

(87) PCT Pub. No.: WO2020/018799
PCT Pub. Date: Jan. 23, 2020

(65) Prior Publication Data
US 2021/0275629 A1    Sep. 9, 2021

Related U.S. Application Data

(60) Provisional application No. 62/699,975, filed on Jul. 18, 2018.

(51) Int. Cl.
*A61K 38/16*    (2006.01)
*A61P 7/08*    (2006.01)
*A61P 13/04*    (2006.01)

(52) U.S. Cl.
CPC .............. *A61K 38/164* (2013.01); *A61P 7/08* (2018.01); *A61P 13/04* (2018.01)

(58) Field of Classification Search
CPC ........... A61K 38/164; A61P 7/08; A61P 13/04
See application file for complete search history.

(56) References Cited

U.S. PATENT DOCUMENTS

| | | | |
|---|---|---|---|
| 5,359,030 A | 10/1994 | Ekwuribe | |
| 5,681,811 A | 10/1997 | Ekwuribe | |
| 6,200,562 B1 | 3/2001 | Allison et al. | |
| 6,552,167 B1 | 4/2003 | Rose | |
| 2012/0308600 A1 | 12/2012 | Castantino et al. | |
| 2014/0030324 A1 | 1/2014 | Sidhu et al. | |
| 2015/0202279 A1* | 7/2015 | Soriani | A61K 39/095 424/190.1 |
| 2020/0188451 A1* | 6/2020 | Hassan | A61K 35/741 |

FOREIGN PATENT DOCUMENTS

| | | |
|---|---|---|
| EP | 3016669 | 5/2016 |
| WO | WO 2005/097176 | 10/2005 |
| WO | WO 2018/136779 | 7/2018 |

OTHER PUBLICATIONS

Drumm et al, Genetic Variation and Clinical Heterogeneity in Cystic Fibrosis, Annu. Rev. Pathol. Mech. Dis., 2012, 7, pp. 267-282.*
Yampolsky et al, The Exchangeability of Amino Acids in Proteins, Genetics, 2005, 170, pp. 1459-1472.*
International Report and Written Opinion for PCT/US19/42416, dated Oct. 25, 2019. 15 pages.
Extended European Search Report for PCT/US2019042416, dated Apr. 2, 2022. 14 pages.
Alexander et al., Kidney stones and kidney function loss: a cohort study. BMJ. Aug. 29, 2012;345:e5287.
Allison et al., *Oxalobacter formigenes* gen. nov., sp. nov.: oxalate-degrading anaerobes that inhabit the gastrointestinal tract. Arch Microbiol. Feb. 1985;141(1):1-7.
Allmendinger et al., Fluoroolefin Dipeptide Isosteres. Tetrahydron Lett., 1990, 31, 7297-7300.
Amin et al., Extracellular nucleotides inhibit oxalate transport by human intestinal Caco-2-BBe cells through PKC-δ activation. Am J Physiol Cell Physiol. Jul. 1, 2013;305(1):C78-89.
Amin et al., Reduced active transcellular intestinal oxalate secretion contributes to the pathogenesis of obesity-associated hyperoxaluria. Kidney Int. May 2018;93(5):1098-1107.
Arvans et al., Oxalobacter formigenes—Derived Bioactive Factors Stimulate Oxalate Transport by Intestinal Epithelial Cells. J Am Soc Nephrol. Mar. 2017;28(3):876-887.
Borthakur et al., The probiotic Lactobacillus acidophilus stimulates chloride/hydroxyl exchange activity in human intestinal epithelial cells. J Nutr. Jul. 2008;138(7):1355-9.
Caudarella et al., Renal stone formation in patients with inflammatory bowel disease. Scanning Microsc. Mar. 1993;7(1):371-9; discussion 379-80.
Chorev et al., A Dozen Years of Retro-Inverso Peptidomimetics. Acc. Chem. Res, 1993, 26, 266-273.
Coe et al., Kidney stone disease. J Clin Invest. Oct. 2005;115(10):2598-608.
Daniel et al., Microbial degradation of oxalate in the gastrointestinal tracts of rats. Appl Environ Microbiol. Aug. 1987;53(8):1793-7.
Danpure et al., Peroxisomal alanine:glyoxylate aminotransferase deficiency in primary hyperoxaluria type I. FEBS Lett. May 26, 1986;201(1):20-4.

(Continued)

*Primary Examiner* — Li N Komatsu
(74) *Attorney, Agent, or Firm* — David W. Staple; Casimir Jones, S.C.

(57) ABSTRACT

Provided herein are compositions comprising Sel1-derived peptides thereof, and method of use thereof for the treatment/prevention excess oxalate levels and conditions and diseases related thereto. In particular, peptides comprise Sel-like repeat (SLR) domains and/or tetratricopeptide (TPR) domains and may be linked together or with other peptides or polypeptides to treat/prevent diseases/conditions related to excess oxalate levels, such as hyperoxaluria and/or hyperoxalemia.

13 Claims, 15 Drawing Sheets

Specification includes a Sequence Listing.

(56) References Cited

OTHER PUBLICATIONS

Database UniProt[online] Ward D; The Genome Sequence of Oxalobacter formigenes OXCC13. Jun. 16, 2009. 2 pages.
Dawson et al., Urolithiasis and hepatotoxicity are linked to the anion transporter Sat1 in mice. J Clin Invest. Mar. 2010;120(3):706-12.
Delgado et al., The uses and properties of PEG-linked proteins. Crit Rev Ther Drug Carrier Syst. 1992;9(3-4):249-304.
DI. Strategic approaches to optimizing peptide ADME properties. AAPS J. Jan. 2015;17(1):134-43.
Duncan et al., Oxalobacter formigenes and its potential role in human health. Appl Environ Microbiol. Aug. 2002;68(8):3841-7.
Eisner et al., Diabetic kidney stone formers excrete more oxalate and have lower urine pH than nondiabetic stone formers. J Urol. Jun. 2010;183(6):2244-8.
Francis et al., PEGylation of cytokines and other therapeutic proteins and peptides: the importance of biological optimisation of coupling techniques. Int. J. Hematology, 1998. 68:1. 11 pages.
Freel et al., Ileal oxalate absorption and urinary oxalate excretion are enhanced in Slc26a6 null mice. Am J Physiol Gastrointest Liver Physiol. Apr. 2006;290(4):G719-28.
Freel et al., Parsing apical oxalate exchange in Caco-2BBe1 monolayers: siRNA knockdown of SLC26A6 reveals the role and properties of PAT-1. Am J Physiol Gastrointest Liver Physiol. Nov. 2009;297(5):G918-29.
Gombotz et al., Biodegradable polymers for protein and peptide drug delivery. Bioconjug Chem. Jul.-Aug. 1995;6(4):332-51.
Hassan et al., Cholinergic signaling inhibits oxalate transport by human intestinal T84 cells. Am J Physiol Cell Physiol. Jan. 1, 2012;302(1):C46-58.
Hatch et al., A human strain of Oxalobacter (HC-1) promotes enteric oxalate secretion in the small intestine of mice and reduces urinary oxalate excretion. Urolithiasis. Oct. 2013;41(5):379-84.
Hatch et al., Enteric oxalate elimination is induced and oxalate is normalized in a mouse model of primary hyperoxaluria following intestinal colonization with Oxalobacter. Am J Physiol Gastrointest Liver Physiol. Mar. 2011;300(3):G461-9.
Hatch et al., Intestinal transport of an obdurate anion: oxalate. Urol Res. Feb. 2005;33(1):1-16.
Hatch et al., *Oxalobacter* sp. reduces urinary oxalate excretion by promoting enteric oxalate secretion. Kidney Int. Feb. 2006;69(4):691-8.
Hoffman et al., The Stereoselective Synthesis of 2-Alkyl .gamma.—Keto Acid and Heterocyclic Ketomethylene Peptide Isostere Core Units Using Chiral Alkylation by 2-Triflyloxy Esters. J. Org. Chem. 1995, 60, 16, 5107-5113.
Hoppe et al., Oxalate degrading bacteria: new treatment option for patients with primary and secondary hyperoxaluria? Urol Res. Nov. 2005;33(5):372-5.
Hoppe et al., Oxalobacter formigenes: a potential tool for the treatment of primary hyperoxaluria type 1. Kidney Int. Oct. 2006;70(7):1305-11.
In et al., Enterohemorrhagic *Escherichia coli* reduce mucus and intermicrovillar bridges in human stem cell-derived colonoids. Cell Mol Gastroenterol Hepatol. Jan. 1, 2016;2(1):48-62.e3.
Jiang et al., Calcium oxalate urolithiasis in mice lacking anion transporter Slc26a6. Nat Genet. Apr. 2006;38(4):474-8.
Jiang et al., Specificity of anion exchange mediated by mouse Slc26a6. J Biol Chem. Sep. 13, 2002;277(37):33963-7.
Kasidas et al., Continuous-flow assay for urinary oxalate using immobilised oxalate oxidase. Ann Clin Biochem. Jul. 1985;22 ( Pt 4):412-9.
Knappe et al., Easy strategy to protect antimicrobial peptides from fast degradation in serum. Antimicrob Agents Chemother. Sep. 2010;54(9):4003-5.
Krogsgaard et al., Chapter 14 of "Drug Design and Development". Horwood Acad. Publishers. 1996. p. 486-528.
Langmead et al., Ultrafast and memory-efficient alignment of short DNA sequences to the human genome. Genome Biol. 2009;10(3):R25. 10 pages.
Lavielle et al., Importance of the leucine side-chain to the spasmogenic activity and binding of substance P analogues. Int J Pept Protein Res. Sep. 1993;42(3):270-7.
Love et al., Moderated estimation of fold change and dispersion for RNA-seq data with DESeq2. Genome Biol. 2014;15(12):550. 21 pages.
Luisi et al., $\psi$(SO2-NH) transition state isosteres of peptides. Synthesis of the glutathione disulfide analogue. Tetrahedron Letters. 1993: vol. 34(14). pp. 2391-2392.
Mehta et al., The role of the microbiome in kidney stone formation. Int J Surg. Dec. 2016;36(Pt D):607-612.
Mittl et al., Sel1-like repeat proteins in signal transduction. Cell Signal. Jan. 2007;19(1):20-31.
Nelson et al., Enteric hyperoxaluria, nephrolithiasis, and oxalate nephropathy: potentially serious and unappreciated complications of Roux-en-Y gastric bypass. Surg Obes Relat Dis. Sep.-Oct. 2005;1(5):481-5.
Ostresh et al., "Libraries from libraries": chemical transformation of combinatorial libraries to extend the range and repertoire of chemical diversity. Proc Natl Acad Sci U S A. Nov. 8, 1994;91(23):11138-42.
Pardi et al., Renal and urologic complications of inflammatory bowel disease. Am J Gastroenterol. Apr. 1998;93(4):504-14.
Robertson et al., The cause of idiopathic calcium stone disease: hypercalciuria or hyperoxaluria? Nephron. 1980;26(3):105-10.
Salido et al., Alanine-glyoxylate aminotransferase-deficient mice, a model for primary hyperoxaluria that responds to adenoviral gene transfer. Proc Natl Acad Sci U S A. Nov. 28, 2006;103(48):18249-54.
Sasaki et al., Protection of $\psi$(CH2NH) Peptide Bond with 2, 4-Dimethoxybenzyl Group in Solid-Phase Peptide Synthesis. J. Chem. Pharm. Bull. 1997. 45(1) 13-17.
Schmidt et al., Structure-activity relationships of dermorphin analogues containing N-substituted amino acids in the 2-position of the peptide sequence. Int J Pept Protein Res. Jul. 1995;46(1):47-55.
Sherman et al., Compatibility of Thioamides with reverse turn features: Synthesis and conformational analysis of two model cyclic pseudopeptides containing thioamides as backbone modifications. J. Am. Chem. Soc. 1990, 112, 433-441.
Sidhu et al., Direct correlation between hyperoxaluria/oxalate stone disease and the absence of the gastrointestinal tract-dwelling bacterium Oxalobacter formigenes: possible prevention by gut recolonization or enzyme replacement therapy. J Am Soc Nephrol. Nov. 1999;10 Suppl 14:S334-40.
Spatola. Synthesis of Pseudopeptides. Methods Neurosci, 1993, 13, p. 19-42.
Tao et al., Soluble factors from Lactobacillus GG activate MAPKs and induce cytoprotective heat shock proteins in intestinal epithelial cells. Am J Physiol Cell Physiol. Apr. 2006;290(4):C1018-30.
UniProtKB Accession No. C3X9N1_OXAFO "Sel1 repeat protein" Jun. 16, 2009 [online]. URL: https://www.uniprot.org/uniprot/C3X9N1. downloaded Jun. 29, 2022. 2 pages.
Whittamore et al., The role of intestinal oxalate transport in hyperoxaluria and the formation of kidney stones in animals and man. Urolithiasis. Feb. 2017;45(1):89-108.
Zachos et al., Human Enteroids/Colonoids and Intestinal Organoids Functionally Recapitulate Normal Intestinal Physiology and Pathophysiology. J Biol Chem. Feb. 19, 2016;291(8):3759-66.
Zalipsky. Functionalized poly(ethylene glycol) for preparation of biologically relevant conjugates. Bioconjug Chem. Mar.-Apr. 1995;6(2):150-65.

\* cited by examiner

SEQUENCE LISTING

<160> NUMBER OF SEQ ID NOS: 47

<210> SEQ ID NO 1
<211> LENGTH: 1572
<212> TYPE: DNA
<213> ORGANISM: Artificial sequence
<220> FEATURE:
<223> OTHER INFORMATION: Synthetic

<400> SEQUENCE: 1
atgtcgtccg tcattgctga ttcgcagcag cctgcagttt cagaagaaaa cgcaaataaa      60
attatccttg atgaggaaaa ggcggtcatc caatgtaacg aaagatataa gacggaaaat     120
gatgaaaagg gcgatgaaga aaccgtttca tggtgccgaa aagccgcgaa gtctggtaat     180
gcggaggcac aatatctttt tggcatgctg gtttatgatg gcagaggcgt gcagcaggat     240
aattgtgttg ccatgttatg gtggatgaaa gcagcagagc agaatcatgc caaggcactc     300
gttatgctgg gaaatcttca tcgtaaaggt cagtgcattg ctgagaatta tccgaaagcc     360
attgcctatt ggaagagagc tgctgttcag aataacgtat gggcatatca taatttaggg     420
acagcttatt acgatggtat cggtgtggat aaaaatcctc atgaagctgt tcgctggtgg     480
aagaaggcag ccgaattggg ttttcctgaa tctcagaaca atctgggtgc tttatacaat     540

```
gatgggaatg gtgttgatcg tgattatcag gaggctgttt tctggtacag aaaaagtgcc    600
ctgcagggcg acgaattggg acagtacaat cttggggtgg cttattatta cggcagaggg    660
ataaaaaaag atttttctga agcagtgtcg tggtacaaaa aatcagcaga acaagactat    720
gcacaagcac agcataatct tggtgttacg tattacgaag gtgagggaat aaaaaaagat    780
tacgccaagg ctgtgtactg gtggaaaaag gcagcagaac aggggattcc ccaatctcag    840
tataaccttg gcattgcata tgaagaaggc tggggcgctg aaaaaaatcc ggagaatgct    900
gttttttggt acagaaaagc ggctgaacag gacatgctg atgctcaaaa cagacttggc    960
atcgcttaca ggtatggaac cggagtcagg aaaaatcccg cattgtctgt caaatggctg   1020
gaaaaagcgg caaagcaggg gcttgcaaga gcacagttca atttggggaa aaccttctat   1080
atcggagcag gcattaacaa gaatacagac aaagcggttt actggttcat aaaagctgcc   1140
aatcagggtt tcacagaagc acaggcttat attggtatga tttattttaa aggtaaatat   1200
gtcgccaaga acgaaaaaaa aggttttttac tggttaaaaa aagcagcaga aaaagacagt   1260
gctaaagcac aagcatttct tggcgcttta tacattgcag gaaatgaagt gaagccaaat   1320
ataaaggaag gcgttgcctt gacaaaaaaa gcggcattac agggtaatta cgaggcacaa   1380
accctgctcg gttttttgcta cgagaatggc ttggaagtaa aaaaagacct gattgccgca   1440
tatgcgcttt acttgtcggc gtcacctcat ttcgattttg cagaaaaggc gcgtcttgat   1500
cttgaacgga aattaagcga acaggaaata gcaaaggcaa tatccgttaa tacagcaaaa   1560
ttgtttgagt ga                                                      1572
```

<210> SEQ ID NO 2
<211> LENGTH: 523
<212> TYPE: PRT
<213> ORGANISM: Artificial sequence
<220> FEATURE:
<223> OTHER INFORMATION: Synthetic

<400> SEQUENCE: 2

Met Ser Ser Val Ile Ala Asp Ser Gln Gln Pro Ala Val Ser Glu Glu
1               5                   10                  15

Asn Ala Asn Lys Ile Ile Leu Asp Glu Glu Lys Ala Val Ile Gln Cys
            20                  25                  30

Asn Glu Arg Tyr Lys Thr Glu Asn Asp Glu Lys Gly Asp Glu Glu Thr
        35                  40                  45

Val Ser Trp Cys Arg Lys Ala Ala Lys Ser Gly Asn Ala Glu Ala Gln
    50                  55                  60

Tyr Leu Phe Gly Met Leu Val Tyr Asp Gly Arg Gly Val Gln Gln Asp
65                  70                  75                  80

Asn Cys Val Ala Met Leu Trp Trp Met Lys Ala Ala Glu Gln Asn His
                85                  90                  95

Ala Lys Ala Leu Val Met Leu Gly Asn Leu His Arg Lys Gly Gln Cys
            100                 105                 110

Ile Ala Glu Asn Tyr Pro Lys Ala Ile Ala Tyr Trp Lys Arg Ala Ala
        115                 120                 125

Val Gln Asn Asn Val Trp Ala Tyr His Asn Leu Gly Thr Ala Tyr Tyr
    130                 135                 140

Asp Gly Ile Gly Val Asp Lys Asn Pro His Glu Ala Val Arg Trp Trp
145                 150                 155                 160

Lys Lys Ala Ala Glu Leu Gly Phe Pro Glu Ser Gln Asn Asn Leu Gly
                165                 170                 175

```
Ala Leu Tyr Asn Asp Gly Asn Gly Val Asp Arg Asp Tyr Gln Glu Ala
            180                 185                 190

Val Phe Trp Tyr Arg Lys Ser Ala Leu Gln Gly Asp Glu Leu Gly Gln
        195                 200                 205

Tyr Asn Leu Gly Val Ala Tyr Tyr Gly Arg Gly Ile Lys Lys Asp
    210                 215                 220

Phe Ser Glu Ala Val Ser Trp Tyr Lys Ser Ala Glu Gln Asp Tyr
225                 230                 235                 240

Ala Gln Ala Gln His Asn Leu Gly Val Thr Tyr Tyr Glu Gly Glu Gly
                245                 250                 255

Ile Lys Lys Asp Tyr Ala Lys Ala Val Tyr Trp Trp Lys Lys Ala Ala
            260                 265                 270

Glu Gln Gly Ile Pro Gln Ser Gln Tyr Asn Leu Gly Ile Ala Tyr Glu
        275                 280                 285

Glu Gly Trp Gly Ala Glu Lys Asn Pro Glu Asn Ala Val Phe Trp Tyr
    290                 295                 300

Arg Lys Ala Ala Glu Gln Gly His Ala Asp Ala Gln Asn Arg Leu Gly
305                 310                 315                 320

Ile Ala Tyr Arg Tyr Gly Thr Gly Val Arg Lys Asn Pro Ala Leu Ser
                325                 330                 335

Val Lys Trp Leu Glu Lys Ala Ala Lys Gln Gly Leu Ala Arg Ala Gln
            340                 345                 350

Phe Asn Leu Gly Lys Thr Phe Tyr Ile Gly Ala Gly Ile Asn Lys Asn
        355                 360                 365

Thr Asp Lys Ala Val Tyr Trp Phe Ile Lys Ala Asn Gln Gly Phe
    370                 375                 380

Thr Glu Ala Gln Ala Tyr Ile Gly Met Ile Tyr Phe Lys Gly Lys Tyr
385                 390                 395                 400

Val Ala Lys Asn Glu Lys Lys Gly Phe Tyr Trp Leu Lys Lys Ala Ala
                405                 410                 415

Glu Lys Asp Ser Ala Lys Ala Gln Ala Phe Leu Gly Ala Leu Tyr Ile
            420                 425                 430

Ala Gly Asn Glu Val Lys Pro Asn Ile Lys Glu Gly Val Ala Leu Thr
        435                 440                 445

Lys Lys Ala Ala Leu Gln Gly Asn Tyr Glu Ala Gln Thr Leu Leu Gly
    450                 455                 460

Phe Cys Tyr Glu Asn Gly Leu Glu Val Lys Lys Asp Leu Ile Ala Ala
465                 470                 475                 480

Tyr Ala Leu Tyr Leu Ser Ala Ser Pro His Phe Asp Phe Ala Glu Lys
                485                 490                 495

Ala Arg Leu Asp Leu Glu Arg Lys Leu Ser Glu Gln Glu Ile Ala Lys
            500                 505                 510

Ala Ile Ser Val Asn Thr Ala Lys Leu Phe Glu
        515                 520

<210> SEQ ID NO 3
<211> LENGTH: 1470
<212> TYPE: DNA
<213> ORGANISM: Artificial sequence
<220> FEATURE:
<223> OTHER INFORMATION: Synthetic

<400> SEQUENCE: 3
atgaaaagac gggttttgta tggtgtgctg tttgcggtgc tggcggggtg ttctgccggt      60
gcgttggcgt ccgtgtccgg cttgtcggat gggctggcgc agcttgaacg gaggcagttc     120
```

```
gaatcggctt atgcgacgct catgccggag gcggagaagg ggaatccccg tgcggcgctg    180
gaggtgggga agctgctgtt gacggggcgc ggggtggcaa aggatgaagc ggcggcggtg    240
aagtggcttc tggtggcggc ggatagtggc aaccgggatg cgcagtatat gctgggggcg    300
atgtcggtgg aggggatcgg tctgccgaag gattctcagg tggcgttgac ctggctgtcg    360
aaggcggcgg cgcaggggga tgcgcgtgcg aagacggctt tggggattct gatgcagtcc    420
gccgggccgg gatcgcagca tacgaacag gcagcccggt ggttcgagag gcggcggcg     480
tcagggaac cggaggcgca acggcgctgg gcgctgatgc tggcgtctgg ccggggggtg    540
gccaaaaatg gggtgaggc actgaaatgg tttaagaagg cggctgtcgc ggggatgtg    600
gaagcgcagc gcaatctggg gattatgctc tcgacgggaa agggggtgac gggcggcaag    660
ccggattttg cggaagcggc acgctggtac ggcctggcag cgaagaaggg ggatgcgaag    720
gcgcagtatg ggttgggcat tttgtatgcg aaggggcagg gggtggcgcc cgatcaggaa    780
aaggcgctga ttctgtatcg catggcggcg actcaggggc tggcgacggc ggagtatgcc    840
gtcgggctgg cgtatgcgta tggacggggg acggcacaaa atgatgtgaa ggcggccgac    900
tggttcgagg cggcggcgca gcaggggtg gtgcgtgcgc aatataatct cgctctgatg    960
ctggaggcgg gtcgcggtcg gcctgtggat acggtggcgg cgagcaagtg gtttttgatg   1020
gcggcggaga agggcttgcg ggaggcacaa tacaatatgg ggtatcacta tgccgagggg   1080
aaggggtgc cacgcgatca gggcaaggcg gtgttctggt atgaaaaggc ggcggctgcc   1140
ggggatgtga aggcccagta caatctgggg atgctgtatc tgaacggggt taatggcaag   1200
gcggatgacg aaaaggcggc ttttttctac cggatggcgg ccggggcggg atatggcccg   1260
gcgatgtacc ggctggcggt gttgtatgag aaggccgtg gggtaaagca gagttatcag   1320
ctggcagggg aatggtatga gcgggcggat ctggccgcga aagtgaagat tgacgaggcg   1380
atgaaaaaga atccgcatcc gtttgtgcaa cggactctgc aggtgccgga tgatttgaat   1440
caatcttcag ataaattggc gggacattag                                    1470
```

<210> SEQ ID NO 4
<211> LENGTH: 489
<212> TYPE: PRT
<213> ORGANISM: Artificial sequence
<220> FEATURE:
<223> OTHER INFORMATION: Synthetic

<400> SEQUENCE: 4

```
Met Lys Arg Arg Val Leu Tyr Gly Val Leu Phe Ala Val Leu Ala Gly
1               5                   10                  15

Cys Ser Ala Gly Ala Leu Ala Ser Val Ser Gly Leu Ser Asp Gly Leu
            20                  25                  30

Ala Gln Leu Glu Arg Arg Gln Phe Glu Ser Ala Tyr Ala Thr Leu Met
        35                  40                  45

Pro Glu Ala Glu Lys Gly Asn Pro Arg Ala Ala Leu Glu Val Gly Lys
    50                  55                  60

Leu Leu Leu Thr Gly Arg Gly Val Ala Lys Asp Glu Ala Ala Val
65                  70                  75                  80

Lys Trp Leu Leu Val Ala Ala Asp Ser Gly Asn Arg Asp Ala Gln Tyr
                85                  90                  95

Met Leu Gly Ala Met Ser Val Glu Gly Ile Gly Leu Pro Lys Asp Ser
            100                 105                 110

Gln Val Ala Leu Thr Trp Leu Ser Lys Ala Ala Ala Gln Gly Asp Ala
```

```
                115                 120                 125
Arg Ala Lys Thr Ala Leu Gly Ile Leu Met Gln Ser Ala Gly Pro Gly
        130                 135                 140

Ser Gln His Thr Glu Gln Ala Arg Trp Phe Glu Arg Ala Ala Ala
145                 150                 155                 160

Ser Gly Glu Pro Glu Ala Gln Arg Arg Trp Ala Leu Met Leu Ala Ser
                165                 170                 175

Gly Arg Gly Val Ala Lys Asn Glu Gly Glu Ala Leu Lys Trp Phe Lys
                180                 185                 190

Lys Ala Ala Val Ala Gly Asp Val Glu Ala Gln Arg Asn Leu Gly Ile
                195                 200                 205

Met Leu Ser Thr Gly Lys Gly Val Thr Gly Gly Lys Pro Asp Phe Ala
        210                 215                 220

Glu Ala Ala Arg Trp Tyr Gly Leu Ala Ala Lys Lys Gly Asp Ala Lys
225                 230                 235                 240

Ala Gln Tyr Gly Leu Gly Ile Leu Tyr Ala Lys Gly Gln Gly Val Ala
                245                 250                 255

Pro Asp Gln Glu Lys Ala Leu Ile Leu Tyr Arg Met Ala Ala Thr Gln
                260                 265                 270

Gly Leu Ala Thr Ala Glu Tyr Ala Val Gly Leu Ala Tyr Ala Tyr Gly
        275                 280                 285

Arg Gly Thr Ala Gln Asn Asp Val Lys Ala Ala Asp Trp Phe Glu Ala
        290                 295                 300

Ala Ala Gln Gln Gly Val Val Arg Ala Gln Tyr Asn Leu Ala Leu Met
305                 310                 315                 320

Leu Glu Ala Gly Arg Gly Arg Pro Val Asp Thr Val Ala Ala Ser Lys
                325                 330                 335

Trp Phe Leu Met Ala Ala Glu Lys Gly Leu Arg Glu Ala Gln Tyr Asn
                340                 345                 350

Met Gly Tyr His Tyr Ala Glu Gly Lys Gly Val Pro Arg Asp Gln Gly
        355                 360                 365

Lys Ala Val Phe Trp Tyr Glu Lys Ala Ala Ala Gly Asp Val Lys
        370                 375                 380

Ala Gln Tyr Asn Leu Gly Met Leu Tyr Leu Asn Gly Val Asn Gly Lys
385                 390                 395                 400

Ala Asp Asp Glu Lys Ala Ala Phe Phe Tyr Arg Met Ala Ala Gly Ala
                405                 410                 415

Gly Tyr Gly Pro Ala Met Tyr Arg Leu Ala Val Leu Tyr Glu Glu Gly
                420                 425                 430

Arg Gly Val Lys Gln Ser Tyr Gln Leu Ala Gly Glu Trp Tyr Glu Arg
        435                 440                 445

Ala Asp Leu Ala Ala Lys Val Lys Ile Asp Glu Ala Met Lys Lys Asn
        450                 455                 460

Pro His Pro Phe Val Gln Arg Thr Leu Gln Val Pro Asp Asp Leu Asn
465                 470                 475                 480

Gln Ser Ser Asp Lys Leu Ala Gly His
                485

<210> SEQ ID NO 5
<211> LENGTH: 35
<212> TYPE: PRT
<213> ORGANISM: Artificial sequence
<220> FEATURE:
<223> OTHER INFORMATION: Synthetic
```

```
<400> SEQUENCE: 5

Ala Asp Ala Gln Asn Arg Leu Gly Ile Ala Tyr Arg Tyr Gly Thr Gly
1               5                   10                  15

Val Arg Lys Asn Pro Ala Leu Ser Val Lys Trp Leu Glu Lys Ala Ala
            20                  25                  30

Lys Gln Gly
        35

<210> SEQ ID NO 6
<211> LENGTH: 30
<212> TYPE: PRT
<213> ORGANISM: Artificial sequence
<220> FEATURE:
<223> OTHER INFORMATION: Synthetic

<400> SEQUENCE: 6

Gln Tyr Asn Leu Gly Val Ala Tyr Tyr Tyr Gly Arg Gly Ile Lys Lys
1               5                   10                  15

Asp Phe Ser Glu Ala Val Ser Trp Tyr Lys Lys Ser Ala Glu
            20                  25                  30

<210> SEQ ID NO 7
<211> LENGTH: 33
<212> TYPE: PRT
<213> ORGANISM: Artificial sequence
<220> FEATURE:
<223> OTHER INFORMATION: Synthetic

<400> SEQUENCE: 7

Ala Tyr His Asn Leu Gly Thr Ala Tyr Tyr Asp Gly Ile Gly Val Asp
1               5                   10                  15

Lys Asn Pro His Glu Ala Val Arg Trp Trp Lys Lys Ala Ala Glu Leu
            20                  25                  30

Gly

<210> SEQ ID NO 8
<211> LENGTH: 35
<212> TYPE: PRT
<213> ORGANISM: Artificial sequence
<220> FEATURE:
<223> OTHER INFORMATION: Synthetic

<400> SEQUENCE: 8

Gln Ser Gln Tyr Asn Leu Gly Ile Ala Tyr Glu Glu Gly Trp Gly Ala
1               5                   10                  15

Glu Lys Asn Pro Glu Asn Ala Val Phe Trp Tyr Arg Lys Ala Ala Glu
            20                  25                  30

Gln Gly His
        35

<210> SEQ ID NO 9
<211> LENGTH: 35
<212> TYPE: PRT
<213> ORGANISM: Artificial sequence
<220> FEATURE:
<223> OTHER INFORMATION: Synthetic

<400> SEQUENCE: 9

Ala Arg Ala Gln Phe Asn Leu Gly Lys Thr Phe Tyr Ile Gly Ala Gly
1               5                   10                  15

Ile Asn Lys Asn Thr Asp Lys Ala Val Tyr Trp Phe Ile Lys Ala Ala
            20                  25                  30
```

Asn Gln Gly
        35

<210> SEQ ID NO 10
<211> LENGTH: 35
<212> TYPE: PRT
<213> ORGANISM: Artificial sequence
<220> FEATURE:
<223> OTHER INFORMATION: Synthetic

<400> SEQUENCE: 10

Glu Ser Gln Asn Asn Leu Gly Ala Leu Tyr Asn Asp Gly Asn Gly Val
1               5                   10                  15

Asp Arg Asp Tyr Gln Glu Ala Val Phe Trp Tyr Arg Lys Ser Ala Leu
            20                  25                  30

Gln Gly Asp
        35

<210> SEQ ID NO 11
<211> LENGTH: 35
<212> TYPE: PRT
<213> ORGANISM: Artificial sequence
<220> FEATURE:
<223> OTHER INFORMATION: Synthetic

<400> SEQUENCE: 11

Glu Ala Gln Tyr Asn Met Gly Tyr His Tyr Ala Glu Gly Lys Gly Val
1               5                   10                  15

Pro Arg Asp Gln Gly Lys Ala Val Phe Trp Tyr Glu Lys Ala Ala Ala
            20                  25                  30

Ala Gly Asp
        35

<210> SEQ ID NO 12
<211> LENGTH: 35
<212> TYPE: PRT
<213> ORGANISM: Artificial sequence
<220> FEATURE:
<223> OTHER INFORMATION: Synthetic

<400> SEQUENCE: 12

Asp Ala Gln Tyr Met Leu Gly Ala Met Ser Val Glu Gly Ile Gly Leu
1               5                   10                  15

Pro Lys Asp Ser Gln Val Ala Leu Thr Trp Leu Ser Lys Ala Ala Ala
            20                  25                  30

Gln Gly Asp
        35

<210> SEQ ID NO 13
<211> LENGTH: 35
<212> TYPE: PRT
<213> ORGANISM: Artificial sequence
<220> FEATURE:
<223> OTHER INFORMATION: Synthetic

<400> SEQUENCE: 13

Ala Lys Ala Gln Tyr Gly Leu Gly Ile Leu Tyr Ala Lys Gly Gln Gly
1               5                   10                  15

Val Ala Pro Asp Gln Glu Lys Ala Leu Ile Leu Tyr Arg Met Ala Ala
            20                  25                  30

Thr Gln Gly
        35

```
<210> SEQ ID NO 14
<211> LENGTH: 35
<212> TYPE: PRT
<213> ORGANISM: Artificial sequence
<220> FEATURE:
<223> OTHER INFORMATION: Synthetic

<400> SEQUENCE: 14

Ala Thr Ala Glu Tyr Ala Val Gly Leu Ala Tyr Ala Tyr Gly Arg Gly
1               5                   10                  15

Thr Ala Gln Asn Asp Val Lys Ala Ala Asp Trp Phe Glu Ala Ala
            20                  25                  30

Gln Gln Gly
        35

<210> SEQ ID NO 15
<211> LENGTH: 35
<212> TYPE: PRT
<213> ORGANISM: Artificial sequence
<220> FEATURE:
<223> OTHER INFORMATION: Synthetic

<400> SEQUENCE: 15

Glu Ala Gln Arg Arg Trp Ala Leu Met Leu Ala Ser Gly Arg Gly Val
1               5                   10                  15

Ala Lys Asn Glu Gly Glu Ala Leu Lys Trp Phe Lys Lys Ala Ala Val
            20                  25                  30

Ala Gly Asp
        35

<210> SEQ ID NO 16
<211> LENGTH: 36
<212> TYPE: PRT
<213> ORGANISM: Artificial sequence
<220> FEATURE:
<223> OTHER INFORMATION: Synthetic

<400> SEQUENCE: 16

Ala Leu Ala Gln Ser Asn Leu Gly Val Leu Tyr Ala Ser Gly Arg Gly
1               5                   10                  15

Val Glu Ser Ser Pro Lys Arg Ala Leu Glu Trp Tyr Lys Lys Ala Ala
            20                  25                  30

Val Gln Gly Asn
        35

<210> SEQ ID NO 17
<211> LENGTH: 36
<212> TYPE: PRT
<213> ORGANISM: Artificial sequence
<220> FEATURE:
<223> OTHER INFORMATION: Synthetic

<400> SEQUENCE: 17

Ser Gln Ala Gln Phe Ser Leu Gly Asn Met Tyr Glu Asp Gly Ser Gly
1               5                   10                  15

Val Glu Lys Asn Leu Ala Val Ala Ala Trp Tyr Gln Lys Ser Ala
            20                  25                  30

Glu Gln Gly Asn
        35

<210> SEQ ID NO 18
```

```
<211> LENGTH: 28
<212> TYPE: PRT
<213> ORGANISM: Artificial sequence
<220> FEATURE:
<223> OTHER INFORMATION: Synthetic

<400> SEQUENCE: 18

Ala Glu Ala Gln Thr Asn Leu Gly Val Leu Tyr Ser Tyr Gly Leu Gly
1               5                   10                  15

Val Asp Lys Asp Leu Ser Lys Ala Phe Tyr Trp Tyr
            20                  25

<210> SEQ ID NO 19
<211> LENGTH: 34
<212> TYPE: PRT
<213> ORGANISM: Artificial sequence
<220> FEATURE:
<223> OTHER INFORMATION: Synthetic

<400> SEQUENCE: 19

Glu Ser Gln Asp Arg Leu Gly Leu Met Leu Thr Asn Gly Val Gly Val
1               5                   10                  15

Lys Gln Asp Tyr Lys Gln Ala Tyr Ser Trp Phe Arg Lys Ala Ala Arg
            20                  25                  30

Gln Gly

<210> SEQ ID NO 20
<211> LENGTH: 31
<212> TYPE: PRT
<213> ORGANISM: Artificial sequence
<220> FEATURE:
<223> OTHER INFORMATION: Synthetic

<400> SEQUENCE: 20

Ala Glu Ser Gln Asn Asn Leu Gly Val Leu Tyr Ala Arg Gly Leu Gly
1               5                   10                  15

Val Glu Lys Asp Tyr Lys Gln Ala Val Ala Trp Tyr Arg Lys Ala
            20                  25                  30

<210> SEQ ID NO 21
<211> LENGTH: 33
<212> TYPE: PRT
<213> ORGANISM: Artificial sequence
<220> FEATURE:
<223> OTHER INFORMATION: Synthetic

<400> SEQUENCE: 21

Gln Ala Gln Phe Asn Leu Gly Thr Met Tyr Leu Gln Gly His Gly Val
1               5                   10                  15

Lys Gln Asp Val Lys Gln Ala Arg His Trp Phe Thr Lys Ala Ala Ala
            20                  25                  30

Gln

<210> SEQ ID NO 22
<211> LENGTH: 35
<212> TYPE: PRT
<213> ORGANISM: Artificial sequence
<220> FEATURE:
<223> OTHER INFORMATION: Synthetic

<400> SEQUENCE: 22

Ala Gln Ala Gln His Asn Leu Gly Val Thr Tyr Tyr Glu Gly Glu Gly
1               5                   10                  15
```

```
Ile Lys Lys Asp Tyr Ala Lys Ala Val Tyr Trp Trp Lys Lys Ala Ala
            20                  25                  30

Glu Gln Gly
        35

<210> SEQ ID NO 23
<211> LENGTH: 36
<212> TYPE: PRT
<213> ORGANISM: Artificial sequence
<220> FEATURE:
<223> OTHER INFORMATION: Synthetic

<400> SEQUENCE: 23

Pro Gln Ser Gln Tyr Asn Leu Gly Ile Ala Tyr Glu Glu Gly Trp Gly
1               5                   10                  15

Ala Glu Lys Asn Pro Glu Asn Ala Val Phe Trp Tyr Arg Lys Ala Ala
            20                  25                  30

Glu Gln Gly His
        35

<210> SEQ ID NO 24
<211> LENGTH: 35
<212> TYPE: PRT
<213> ORGANISM: Artificial sequence
<220> FEATURE:
<223> OTHER INFORMATION: Synthetic

<400> SEQUENCE: 24

Glu Ala Gln Ala Tyr Ile Gly Met Ile Tyr Phe Lys Gly Lys Tyr Val
1               5                   10                  15

Ala Lys Asn Glu Lys Lys Gly Phe Tyr Trp Leu Lys Lys Ala Ala Glu
            20                  25                  30

Lys Asp Ser
        35

<210> SEQ ID NO 25
<211> LENGTH: 33
<212> TYPE: PRT
<213> ORGANISM: Artificial sequence
<220> FEATURE:
<223> OTHER INFORMATION: Synthetic

<400> SEQUENCE: 25

Ala Leu Tyr Gly Leu Gly Val Met Ala Thr Asn Gly Leu Gly Met Pro
1               5                   10                  15

Arg Asn Asp Glu Lys Ala Leu Val Trp Phe Arg Glu Gly Ala Ala Lys
            20                  25                  30

Gly

<210> SEQ ID NO 26
<211> LENGTH: 34
<212> TYPE: PRT
<213> ORGANISM: Artificial sequence
<220> FEATURE:
<223> OTHER INFORMATION: Synthetic

<400> SEQUENCE: 26

Glu Ala Gln Phe Gly Leu Gly Ala Met Tyr Asp Leu Ser Arg Gly Val
1               5                   10                  15

Arg Gln Asp Met Thr Leu Ala Ile Asp Trp Tyr Glu Lys Ser Ala Arg
            20                  25                  30

Ala Gly
```

<210> SEQ ID NO 27
<211> LENGTH: 32
<212> TYPE: PRT
<213> ORGANISM: Artificial sequence
<220> FEATURE:
<223> OTHER INFORMATION: Synthetic

<400> SEQUENCE: 27

Gln Leu Tyr Leu Gly Leu Met Tyr Gly His Gly Lys Gly Val Pro Arg
1               5                   10                  15

Asp Leu Asn Lys Ser Leu Phe Trp Val Glu Lys Ala Ala Asp Arg Gly
            20                  25                  30

<210> SEQ ID NO 28
<211> LENGTH: 34
<212> TYPE: PRT
<213> ORGANISM: Artificial sequence
<220> FEATURE:
<223> OTHER INFORMATION: Synthetic

<400> SEQUENCE: 28

Ala Gln Tyr Leu Met Gly Met Ala Tyr Leu Glu Gly Lys Ser Val Pro
1               5                   10                  15

Gln Asp Leu Pro Val Ala Ala Ala Trp Phe Tyr Lys Ala Ala Met Gln
            20                  25                  30

Gly Asn

<210> SEQ ID NO 29
<211> LENGTH: 36
<212> TYPE: PRT
<213> ORGANISM: Artificial sequence
<220> FEATURE:
<223> OTHER INFORMATION: Synthetic

<400> SEQUENCE: 29

Ala Asp Ala Gln Leu Arg Leu Gly Tyr Met Tyr Ala Arg Gly Ile Gly
1               5                   10                  15

Val Pro Val Asp Lys Pro Lys Ala Val Ala Trp Leu Glu Lys Ala Ala
            20                  25                  30

Ser Ala Gly Asn
        35

<210> SEQ ID NO 30
<211> LENGTH: 29
<212> TYPE: PRT
<213> ORGANISM: Artificial sequence
<220> FEATURE:
<223> OTHER INFORMATION: Synthetic

<400> SEQUENCE: 30

Gly Ser Met Leu Ser Gln Gly Lys Gly Val Glu Lys Asp Pro Lys Lys
1               5                   10                  15

Gly Leu Glu Trp Phe Val Gln Ala Gly Gln Asp Gly Asp
            20                  25

<210> SEQ ID NO 31
<211> LENGTH: 36
<212> TYPE: PRT
<213> ORGANISM: Artificial sequence
<220> FEATURE:
<223> OTHER INFORMATION: Synthetic

<400> SEQUENCE: 31

```
Ser Glu Ala Gln Gln Met Met Gly Phe Leu Tyr Gly Glu Gly Trp Gly
1               5                   10                  15

Ala Lys Arg Asp Pro Val Lys Ala Glu Tyr Trp Phe Asp Lys Ala Ala
                20                  25                  30

Ala Ser Gly Asp
            35

<210> SEQ ID NO 32
<211> LENGTH: 34
<212> TYPE: PRT
<213> ORGANISM: Artificial sequence
<220> FEATURE:
<223> OTHER INFORMATION: Synthetic

<400> SEQUENCE: 32

Gln Ala Glu His Glu Met Gly Ser Leu Tyr Leu Met Gly Ile Gly Val
1               5                   10                  15

Ala Gln Ser Asn Val Met Ala Val Ala Trp Tyr Arg Lys Ala Ala Ile
                20                  25                  30

Gln Gly

<210> SEQ ID NO 33
<211> LENGTH: 36
<212> TYPE: PRT
<213> ORGANISM: Artificial sequence
<220> FEATURE:
<223> OTHER INFORMATION: Synthetic

<400> SEQUENCE: 33

Ala Pro Ser Gln Thr Ala Met Gly Tyr Ala Tyr Glu Glu Gly Ala Gly
1               5                   10                  15

Val Pro Gln Asp Ala Asp Leu Ala Arg Tyr Trp Phe Asp Lys Ala Ala
                20                  25                  30

Ala Gln Gly Asn
            35

<210> SEQ ID NO 34
<211> LENGTH: 33
<212> TYPE: PRT
<213> ORGANISM: Artificial sequence
<220> FEATURE:
<223> OTHER INFORMATION: Synthetic

<400> SEQUENCE: 34

Ala Gln Ala Gly Leu Gly Trp Met Tyr Ala Ala Gly Arg Gly Val Asn
1               5                   10                  15

Lys Asp Glu Thr Leu Ser Phe Ser Trp Tyr Glu Arg Ala Ala Val Ala
                20                  25                  30

Gly

<210> SEQ ID NO 35
<211> LENGTH: 34
<212> TYPE: PRT
<213> ORGANISM: Artificial sequence
<220> FEATURE:
<223> OTHER INFORMATION: Synthetic

<400> SEQUENCE: 35

Ala Gln Tyr Met Leu Gly Arg Tyr Tyr Glu Lys Gly Ile Gly Val Ala
1               5                   10                  15

Lys Asp Arg Val Leu Ala Lys Glu Trp Tyr Glu Lys Ala Ala Ala Gln
```

-continued

```
                    20                  25                  30

Gly Asn

<210> SEQ ID NO 36
<211> LENGTH: 80
<212> TYPE: PRT
<213> ORGANISM: Artificial sequence
<220> FEATURE:
<223> OTHER INFORMATION: Synthetic

<400> SEQUENCE: 36

Lys Ala Ala Lys Ser Gly Asn Ala Glu Ala Gln Tyr Leu Phe Gly Met
1               5                   10                  15

Leu Val Tyr Asp Gly Arg Gly Val Gln Gln Asp Asn Cys Val Ala Met
                20                  25                  30

Leu Trp Trp Met Lys Ala Ala Glu Gln Asn His Ala Lys Ala Leu Val
            35                  40                  45

Met Leu Gly Asn Leu His Arg Lys Gly Gln Cys Ile Ala Glu Asn Tyr
50                  55                  60

Pro Lys Ala Ile Ala Tyr Trp Lys Arg Ala Ala Val Gln Asn Asn Val
65                  70                  75                  80

<210> SEQ ID NO 37
<211> LENGTH: 98
<212> TYPE: PRT
<213> ORGANISM: Artificial sequence
<220> FEATURE:
<223> OTHER INFORMATION: Synthetic

<400> SEQUENCE: 37

Leu Gly Thr Ala Tyr Tyr Asp Gly Ile Gly Val Asp Lys Asn Pro His
1               5                   10                  15

Glu Ala Val Arg Trp Trp Lys Lys Ala Ala Glu Leu Gly Phe Pro Glu
                20                  25                  30

Ser Gln Asn Asn Leu Gly Ala Leu Tyr Asn Asp Gly Asn Gly Val Asp
            35                  40                  45

Arg Asp Tyr Gln Glu Ala Val Phe Trp Tyr Arg Lys Ser Ala Leu Gln
50                  55                  60

Gly Asp Glu Leu Gly Gln Tyr Asn Leu Gly Val Ala Tyr Tyr Gly Arg
65                  70                  75                  80

Gly Ile Lys Lys Asp Phe Ser Glu Ala Val Ser Trp Tyr Lys Lys Ser
                85                  90                  95

Ala Glu

<210> SEQ ID NO 38
<211> LENGTH: 87
<212> TYPE: PRT
<213> ORGANISM: Artificial sequence
<220> FEATURE:
<223> OTHER INFORMATION: Synthetic

<400> SEQUENCE: 38

Tyr Arg Lys Ala Ala Glu Gln Gly His Ala Asp Ala Gln Asn Arg Leu
1               5                   10                  15

Gly Ile Ala Tyr Arg Tyr Gly Thr Gly Val Arg Lys Asn Pro Ala Leu
                20                  25                  30

Ser Val Lys Trp Leu Glu Lys Ala Ala Lys Gln Gly Leu Ala Arg Ala
            35                  40                  45

Gln Phe Asn Leu Gly Lys Thr Phe Tyr Ile Gly Ala Gly Ile Asn Lys
```

50                  55                  60

Asn Thr Asp Lys Ala Val Tyr Trp Phe Ile Lys Ala Ala Asn Gln Gly
 65                  70                  75                  80

Phe Thr Glu Ala Gln Ala Tyr
                 85

<210> SEQ ID NO 39
<211> LENGTH: 35
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-terminal Acetyl modification

<400> SEQUENCE: 39

Asp Ala Gln Tyr Met Leu Gly Ala Met Ser Val Glu Gly Ile Gly Leu
 1               5                  10                  15

Pro Lys Asp Ser Gln Val Ala Leu Thr Trp Leu Ser Lys Ala Ala Ala
                 20                  25                  30

Gln Gly Asp
         35

<210> SEQ ID NO 40
<211> LENGTH: 34
<212> TYPE: PRT
<213> ORGANISM: Artificial sequence
<220> FEATURE:
<223> OTHER INFORMATION: Synthetic

<400> SEQUENCE: 40

Asp Ala Gln Tyr Met Leu Gly Ala Met Ser Val Glu Gly Ile Leu Pro
 1               5                  10                  15

Lys Ser Gln Val Ala Leu Thr Trp Leu Ser Lys Ala Ala Ala Gln
         20                  25                  30

Gly Asp

<210> SEQ ID NO 41
<211> LENGTH: 35
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (35)..(35)
<223> OTHER INFORMATION: C-terminal Amide modification

<400> SEQUENCE: 41

Asp Ala Gln Tyr Met Leu Gly Ala Met Ser Val Glu Gly Ile Gly Leu
 1               5                  10                  15

Pro Lys Asp Ser Gln Val Ala Leu Thr Trp Leu Ser Lys Ala Ala Ala
                 20                  25                  30

Gln Gly Asp
         35

<210> SEQ ID NO 42
<211> LENGTH: 31
<212> TYPE: PRT
<213> ORGANISM: Artificial sequence
<220> FEATURE:
<223> OTHER INFORMATION: Synthetic

<400> SEQUENCE: 42

Asp Ala Gln Tyr Met Leu Ala Met Ser Val Glu Ile Leu Pro Lys Asp
1               5                   10                  15

Ser Gln Val Ala Leu Thr Trp Leu Ser Lys Ala Ala Ala Gln Asp
            20                  25                  30

<210> SEQ ID NO 43
<211> LENGTH: 35
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-terminal Acetyl modification

<400> SEQUENCE: 43

Ala Lys Ala Gln Tyr Gly Leu Gly Ile Leu Tyr Ala Lys Gly Gln Gly
1               5                   10                  15

Val Ala Pro Asp Gln Glu Lys Ala Leu Ile Leu Tyr Arg Met Ala Ala
            20                  25                  30

Thr Gln Gly
        35

<210> SEQ ID NO 44
<211> LENGTH: 34
<212> TYPE: PRT
<213> ORGANISM: Artificial sequence
<220> FEATURE:
<223> OTHER INFORMATION: Synthetic

<400> SEQUENCE: 44

Ala Lys Ala Gln Tyr Gly Leu Gly Ile Leu Tyr Ala Lys Gly Gln Val
1               5                   10                  15

Ala Pro Asp Gln Glu Lys Ala Leu Ile Leu Tyr Arg Met Ala Ala Thr
            20                  25                  30

Gln Gly

<210> SEQ ID NO 45
<211> LENGTH: 35
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (35)..(35)
<223> OTHER INFORMATION: C-terminal Amide modification

<400> SEQUENCE: 45

Ala Lys Ala Gln Tyr Gly Leu Gly Ile Leu Tyr Ala Lys Gly Gln Gly
1               5                   10                  15

Val Ala Pro Asp Gln Glu Lys Ala Leu Ile Leu Tyr Arg Met Ala Ala
            20                  25                  30

Thr Gln Gly
        35

<210> SEQ ID NO 46
<211> LENGTH: 30
<212> TYPE: PRT
<213> ORGANISM: Artificial sequence
<220> FEATURE:

```
<223> OTHER INFORMATION: Synthetic

<400> SEQUENCE: 46

Ala Lys Ala Gln Tyr Leu Ile Leu Tyr Ala Lys Gln Val Ala Pro Asp
1               5                   10                  15

Gln Glu Lys Ala Leu Ile Leu Tyr Arg Met Ala Ala Thr Gln
            20                  25                  30

<210> SEQ ID NO 47
<211> LENGTH: 36
<212> TYPE: PRT
<213> ORGANISM: Artificial sequence
<220> FEATURE:
<223> OTHER INFORMATION: Synthetic

<400> SEQUENCE: 47

Arg Asp Ala Gln Tyr Met Leu Gly Ala Met Ser Val Glu Gly Ile Gly
1               5                   10                  15

Leu Pro Lys Asp Ser Gln Val Ala Leu Thr Trp Leu Ser Lys Ala Ala
            20                  25                  30

Ala Gln Gly Asp
            35
```

COMPOSITIONS COMPRISING SEL1-DERIVED PEPTIDES AND METHODS OF TREATMENT/PREVENTION OF EXCESS OXALATE LEVELS AND ASSOCIATED CONDITIONS/DISEASES THEREWITH This invention was made with government support under grant numbers DK067245, DK042086 and DK101643 awarded by The National Institutes of Health. The government has certain rights in the invention.

SEQUENCE LISTING

The text of the computer readable sequence listing filed herewith, titled "36476-252_SEQUENCE_LISTING_ST25.txt", created Nov. 2, 2023, having a file size of 32,391 bytes, is hereby incorporated by reference in its entirety.

FIELD

Provided herein are compositions comprising Sel1-derived peptides, and method of use thereof for the treatment/prevention of excess oxalate levels and conditions and diseases related thereto. In particular, peptides comprise Sel-like repeat (SLR) domains and/or tetratricopeptide (TPR) domains and may be linked together or administered with other peptides or polypeptides to treat/prevent diseases/conditions related to excess oxalate levels, such as hyperoxaluria and/or hyperoxalemia.

BACKGROUND

Nephrolithiasis, or the formation of mineral deposit blockages in the kidney (kidney stones (KS)), is the second most prevalent kidney disease in USA after hypertension, with a rising prevalence and complications including advanced chronic kidney disease (CKD) and end stage renal disease (ESRD). It remains a major source of patient discomfort and disability, lost working days, and health-care expenditure, with an annual economic cost approaching $10 billion. Hyperoxaluria (HO) is a major risk factor for KS, and 70-80% of KS are composed of calcium oxalate. Urinary oxalate is an important determinant of supersaturation, and the risk for stone formation is affected by small increases in urine oxalate. Oxalate is a metabolic end product that cannot be further metabolized and is highly toxic. The mammalian intestine plays a crucial role in oxalate homeostasis, by regulating the amount of absorbed dietary oxalate and providing an avenue for enteric oxalate excretion. Anion exchanger SLC26A6 (A6)-mediated intestinal oxalate secretion plays a critical role in preventing hyperoxaluria and calcium oxalate kidney stones (COKS). Inflammatory bowel disease patients have a significantly increased risk of KS due to the associated enteric hyperoxaluria. Obesity is a risk factor for KS and obese stone formers often have mild to moderate hyperoxaluria. Hyperoxaluria is also emerging as a major complication (developing in >50% of patients) of bariatric surgery for obesity. With the rising prevalence of obesity and increased utilization of bariatric surgery, it is expected that the incidence of hyperoxaluria and related COKS (including the associated cost burden) will continue to increase at a significant rate. Primary hyperoxaluria (PH) is an inherited disease in which there is endogenous oxalate overproduction, which leads to recurrent KS and/or progressive nephrocalcinosis, ESRD, as well as significant hyperoxalemia, systemic oxalosis and premature death. Systemic deposition of calcium oxalate (oxalosis) leads to bone disease, cardiac arrhythmias, cardiomyopathy, skin ulcers, erythropoietin refractory anemia, and digital gangrene. The only treatment known to fully correct the underlying metabolic defect is liver transplantation or combined kidney-liver transplantation once ESRD develops. In addition, significant hyperoxalemia is also seen in ESRD. Cardiovascular diseases are the leading cause of morbidity and mortality in ESRD patients, and a recent report suggest that the ESRD-associated hyperoxalemia may contribute to this increased risk.

Kidney stones (KS) affect ~1 in 5 men and ~1 in 11 women, are costly (>$10B annually), and are associated with CKD and ESRD. High recurrence rates (50% in 5 years and up to 80% in 10 years), indicate that current interventions are inadequate and alternative therapies are needed. Most KS are composed of calcium oxalate and very small increases in urine oxalate concentration enhance the risk for stone formation. Lower urinary calcium oxalate (CaOx) supersaturation definitively reduces KS formation. Currently no 1-DA approved drugs reduce urinary oxalate excretion. The gut bacterium *Oxalobacter formigens* (Of) induces colonic oxalate secretion and reduces urinary oxalate excretion via a secretagogue. Given the difficulties with recolonization, Of alone is not therapeutically feasible and underscores the need to utilize the secretagogue that induces colonic oxalate secretion.

SUMMARY

Provided herein are compositions comprising Sel1-derived peptides, and method of use thereof for the treatment/prevention of excess oxalate levels and conditions and diseases related thereto. In particular, peptides comprise Sel-like repeat (SLR) domains and/or tetratricopeptide (TPR) domains and may be linked together or administered with other peptides or polypeptides to treat/prevent diseases/conditions related to excess oxalate levels, such as hyperoxaluria and/or hyperoxalemia.

In some embodiments, provided herein are compositions comprising a Sel1-derived peptide sequence at least 60% (e.g., 60%, 65%, 70%, 75%, 80%, 85%, 90%, 95%, 99%, 100%, or ranges therebetween) sequence identity to one of SEQ ID NOs: 5-46, wherein the composition is not a product of nature. In some embodiments, the Sel1-derived peptide sequence has less than 100% sequence identity to SEQ ID NOs: 5-46. In some embodiments, the Sel1-derived peptide sequence is fused to a second peptide or polypeptide sequence. In some embodiments, the second peptide or polypeptide sequence is a carrier moiety, therapeutic moiety, detectable moiety, or Sel1-derived peptide sequence. In some embodiments, the composition comprises 2 or more Sel1-derived peptide sequences with at least 60% sequence identity to one of SEQ ID NOs: 5-46. In some embodiments, the Sel1-derived peptide sequences are fused directly or indirectly to each other. In some embodiments, the Sel1-derived peptide sequences are not fused to each other. In some embodiments, (i) one or more of the amino acid residues in the peptide sequence(s) are D-enantiomers, (ii) the peptide sequence(s) comprise a one or more unnatural amino acids, (iii) the peptide sequence(s) comprise a one or more amino acid analogs, and/or (iv) the peptide sequence(s) comprise a one or more peptoid amino acids. In some embodiments, the peptide sequence(s) or an amino acid therein comprises a modification selected from the group consisting of phosphorylation, glycosylation, ubiquitination, S-nitrosylation, methylation, N-acetylation, lipidation, lipoylation, deimination, eliminylation, disulfide bridging, isoaspartate formation, racemization, glycation; carbamylation, carbonylation, isopeptide bond formation, sulfation, succinylation, S-sulfonylation, S-sulfinylation, S-sulfenylation, S-glutathionylation, pyroglutamate formation, propionylation, adenylylation, nucleotide addition, iodination, hydroxylation, malonylation, butyrylation, amidation, alkylation, acylation, biotinylation, carbamylation, oxidation, and pegylation. In some embodiments, the peptide sequence(s) exhibit enhanced stability relative to one of SEQ ID NOs: 5-46. In some embodiments, the peptide sequence(s) exhibit enhanced oxalate-transport stimulation relative to one of SEQ ID NOs: 5-46.

In some embodiments, provided herein are pharmaceutical compositions comprising a Sel1-derived peptide composition described herein and a pharmaceutically-acceptable carrier. In some embodiments, the pharmaceutical composition further comprises one or more additional therapeutic agents. In some embodiments, the additional therapeutic agent is an oxalate degrading enzyme (e.g., oxalate oxidase, oxalate decarboxylase, oxalyl-CoA decarboxylase, formyl-CoA transferase, etc.). In some embodiments, the additional therapeutic agent is an oxalate degrading organism (e.g., bacteria, etc.).

In some embodiments, provided herein are methods of stimulating oxalate transport comprising administering to a subject a composition described herein. In some embodiments, administration comprises rectal administration, oral administration, and/or injection. In some embodiments, the subject suffers from or is at risk for hyperoxaluria and/or hyperoxalemia. In some embodiments, the subject's risk of the risk of calcium oxalate kidney stones, nephrocalcinosis, oxalate nephropathy, end stage renal disease, chronic kidney disease, and/or systemic oxalosis is lowered by the method.

In some embodiments, provided herein are methods of treating or preventing hyperoxaluria and/or hyperoxalemia comprising administering a pharmaceutical composition (e.g., comprising a Sel1-derived peptide) described herein to a subject. In some embodiments, treating or preventing hyperoxaluria and/or hyperoxalemia lowers the subject's risk of the risk of calcium oxalate kidney stones, nephrocalcinosis, oxalate nephropathy, end stage renal disease, and/or systemic oxalosis.

DEFINITIONS

Figure 1:
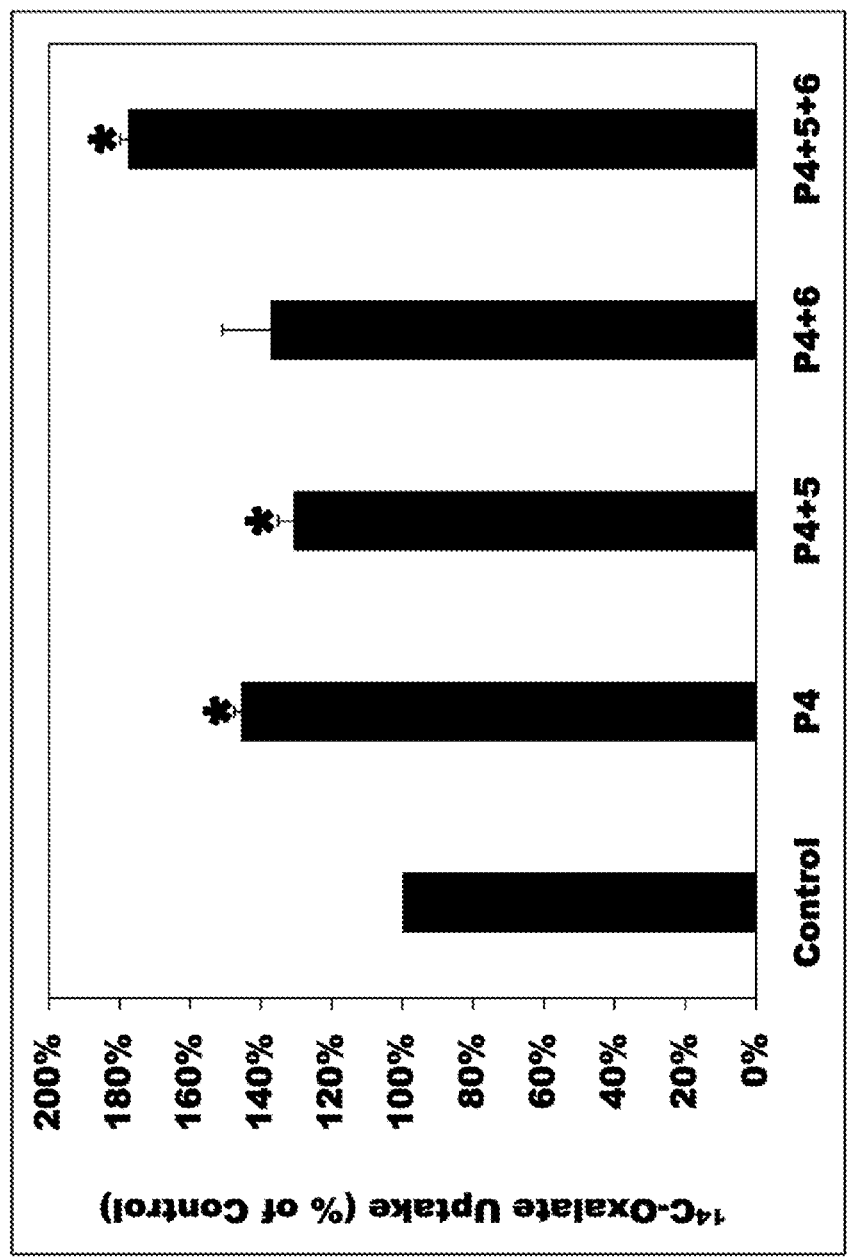
FIG. 1. 301-derived peptides (individually or in combination) significantly stimulate $^{14}C$-oxalate influx into human Caco2-BBE (C2) cells.

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a Sel1-derived peptide" is a reference to one or more Sel1-derived peptides and equivalents thereof known to those skilled in the art, and so forth.

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

As used herein, the term "hyperoxaluria" refers to the excessive urinary excretion of oxalate by a subject (e.g., >25 mg/day).

As used herein, the term "hyperoxalemia" refers to excessive plasma levels of oxalate in a subject. Various studies report a normal range of oxalate in the plasma of 1 to 3 µmol per liter. Subjects with levels exceeding that range are considered to suffer from hyperoxalemia.

The term "amino acid" refers to natural amino acids, unnatural amino acids, and amino acid analogs, all in their D and L stereoisomers, unless otherwise indicated, if their structures allow such stereoisomeric forms.

Natural amino acids include alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), Lysine (Lys or K), methionine (Met or M), phenylalanine (Phe or F), proline (Pro or P), serine (Ser or S), threonine (Thr or T), tryptophan (Trp or W), tyrosine (Tyr or Y) and valine (Val or V).

Unnatural amino acids include, but are not limited to, azetidinecarboxylic acid, 2-aminoadipic acid, 3-aminoadipic acid, beta-alanine, naphthylalanine ("naph"), aminopropionic acid, 2-aminobutyric acid, 4-aminobutyric acid, 6-aminocaproic acid, 2-aminoheptanoic acid, 2-aminoisobutyric acid, 3-aminoisbutyric acid, 2-aminopimelic acid, tertiary-butylglycine ("tBuG"), 2,4-diaminoisobutyric acid, desmosine, 2,2'-diaminopimelic acid, 2,3-diaminopropionic acid, N-ethylglycine, N-ethylasparagine, homoproline ("hPro" or "homoP"), hydroxylysine, allo-hydroxylysine, 3-hydroxyproline ("3Hyp"), 4-hydroxyproline ("4Hyp"), isodesmosine, allo-isoleucine, N-methylalanine ("MeAla" or "Nime"), N-alkylglycine ("NAG") including N-methylglycine, N-methylisoleucine, N-alkylpentylglycine ("NAPG") including N-methylpentylglycine. N-methylvaline, naphthylalanine, norvaline ("Norval"), norleucine ("Norleu"), octylglycine ("OctG"), ornithine ("Orn"), pentylglycine ("pG" or "PGly"), pipecolic acid, thioproline ("ThioP" or "tPro"), homoLysine ("hLys"), and homoArginine ("hArg").

The term "amino acid analog" refers to a natural or unnatural amino acid where one or more of the C-terminal carboxy group, the N-terminal amino group and side-chain functional group has been chemically blocked, reversibly or irreversibly, or otherwise modified to another functional group. For example, aspartic acid-(beta-methyl ester) is an amino acid analog of aspartic acid; N-ethylglycine is an amino acid analog of glycine; or alanine carboxamide is an amino acid analog of alanine. Other amino acid analogs include methionine sulfoxide, methionine sulfone, S-(carboxymethyl)-cysteine, S-(carboxymethyl)-cysteine sulfoxide and S-(carboxymethyl)-cysteine sulfone.

As used herein, the term "peptide" refers a short polymer of amino acids linked together by peptide bonds. In contrast to other amino acid polymers (e.g., proteins, polypeptides, etc.), peptides are of about 50 amino acids or less in length. A peptide may comprise natural amino acids, non-natural amino acids, amino acid analogs, and/or modified amino acids. A peptide may be a subsequence of naturally occurring protein or a non-natural (synthetic) sequence.

As used herein, the term "mutant peptide" or "variant peptide" refers to a peptide having a distinct amino acid sequence from the most common variant occurring in nature, referred to as the "wild-type" sequence. A mutant peptide may be a subsequence of a mutant protein or polypeptide (e.g., a subsequence of a naturally-occurring protein that is not the most common sequence in nature) or may be a peptide that is not a subsequence of a naturally occurring protein or polypeptide. For example, a "mutant SLR peptide" (e.g., a "mutant Sel1 protein") may be a subsequence of a mutant version of SLR protein (e.g., Sel1 protein) or may be distinct sequence not found in naturally-occurring SLR proteins (e.g., Sel1 proteins).

As used herein, the term "mutant polypeptide" or "variant polypeptide" refers to a polypeptide having a distinct amino acid sequence from the "wild-type" sequence. A mutant polypeptide may be a naturally-occurring protein that is not the most common sequence in nature (or a polypeptide fragment thereof) or may be a polypeptide that is not a subsequence of a naturally occurring protein or polypeptide. For example, a "mutant SLR polypeptide" may be a naturally occurring SLR protein (e.g., Sel1 protein), a polypeptide fragment of a SLR protein (e.g., Sel1 protein), or may be distinct sequence not found in naturally-occurring SLR proteins (e.g., Sel1 proteins).

As used herein, the term "artificial peptide" or "artificial polypeptide" refers to a peptide or polypeptide having a distinct amino acid sequence from those found in natural peptides and/or proteins. An artificial protein is not a subsequence of a naturally occurring protein, either the wild-type (i.e., most abundant) or mutant versions thereof. For example, an artificial SLR peptide or polypeptide is not a subsequence of naturally occurring SLR protein (e.g., Sel1 protein). An artificial peptide or polypeptide may be produced or synthesized by any suitable method (e.g., recombinant expression, chemical synthesis, enzymatic synthesis, etc.).

The terms "peptide mimetic" or "peptidomimetic" refer to a peptide-like molecule that emulates a sequence derived from a protein or peptide. A peptide mimetic or peptidomimetic may contain amino acids and/or non-amino acid components. Examples of peptidomimtecs include chemically modified peptides, peptoids (side chains are appended to the nitrogen atom of the peptide backbone, rather than to the α-carbons), (β-peptides (amino group bonded to the β carbon rather than the α carbon), etc.

As used herein, a "conservative" amino acid substitution refers to the substitution of an amino acid in a peptide or polypeptide with another amino acid having similar chemical properties, such as size or charge. For purposes of the present disclosure, each of the following eight groups contains amino acids that are conservative substitutions for one another:
  1) Alanine (A) and Glycine (G);
  2) Aspartic acid (D) and Glutamic acid (E);
  3) Asparagine (N) and Glutamine (Q);
  4) Arginine (R) and Lysine (K);
  5) Isoleucine (I), Leucine (L), Methionine (M), and Valine (V);
  6) Phenylalanine (F), Tyrosine (Y), and Tryptophan (W);
  7) Serine (S) and Threonine (T); and
  8) Cysteine (C) and Methionine (M).

Naturally occurring residues may be divided into classes based on common side chain properties, for example: polar positive (histidine (H), lysine (K), and arginine (R)); polar negative (aspartic acid (D), glutamic acid (E)); polar neutral (serine (S), threonine (T), asparagine (N), glutamine (Q));

non-polar aliphatic (alanine (A), valine (V), leucine (L), isoleucine (I), methionine (M)); non-polar aromatic (phenylalanine (F), tyrosine (Y), tryptophan (W)); proline and glycine; and cysteine. As used herein, a "semi-conservative" amino acid substitution refers to the substitution of an amino acid in a peptide or polypeptide with another amino acid within the same class.

In some embodiments, unless otherwise specified, a conservative or semi-conservative amino acid substitution may also encompass non-naturally occurring amino acid residues that have similar chemical properties to the natural residue. These non-natural residues are typically incorporated by chemical peptide synthesis rather than by synthesis in biological systems. These include, but are not limited to, peptidomimetics and other reversed or inverted forms of amino acid moieties. Embodiments herein may, in some embodiments, be limited to natural amino acids, non-natural amino acids, and/or amino acid analogs. Non-conservative substitutions may involve the exchange of a member of one class for a member from another class.

As used herein, the term "sequence identity" refers to the degree to which two polymer sequences (e.g., peptide, polypeptide, nucleic acid, etc.) have the same sequential composition of monomer subunits. The term "sequence similarity" refers to the degree with which two polymer sequences (e.g., peptide, polypeptide, nucleic acid, etc.) differ only by conservative and/or semi-conservative amino acid substitutions. The "percent sequence identity" (or "percent sequence similarity") is calculated by: (1) comparing two optimally aligned sequences over a window of comparison (e.g., the length of the longer sequence, the length of the shorter sequence, a specified window, etc.), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

As used herein, the term "subject" broadly refers to any animal, including but not limited to, human and non-human animals (e.g., dogs, cats, cows, horses, sheep, poultry, fish, crustaceans, etc.). As used herein, the term "patient" typically refers to a human subject that is being treated for a disease or condition.

As used herein, the term "effective amount" refers to the amount of a sufficient to effect beneficial or desired results. An effective amount can be administered in one or more administrations, applications or dosages and is not intended to be limited to a particular formulation or administration route.

As used herein, the terms "administration" and "administering" refer to the act of giving a drug, prodrug, or other agent, or therapeutic treatment to a subject or in vivo, in vitro, or ex vivo cells, tissues, and organs. Exemplary routes of administration to the human body can be through space under the arachnoid membrane of the brain or spinal cord (intrathecal), the eyes (ophthalmic), mouth (oral), skin (topical or transdermal), nose (nasal), lungs (inhalant), oral mucosa (buccal), ear, rectal, vaginal, by injection (e.g., intravenously, subcutaneously, intratumorally, intraperitoneally, etc.) and the like.

As used herein, the terms "co-administration" and "co-administering" refer to the administration of at least two agent(s) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

As used herein, the term "treatment" means an approach to obtaining a beneficial or intended clinical result. The beneficial or intended clinical result may include alleviation of symptoms, a reduction in the severity of the disease, inhibiting an underlying cause of a disease or condition, steadying diseases in a non-advanced state, delaying the progress of a disease, and/or improvement or alleviation of disease conditions.

As used herein, the term "pharmaceutical composition" refers to the combination of an active agent (e.g., Sel1-derived peptide) with a carrier, inert or active, making the composition especially suitable for diagnostic or therapeutic use in vitro, in vivo or ex vivo. The terms "pharmaceutically acceptable" or "pharmacologically acceptable," as used herein, refer to compositions that do not substantially produce adverse reactions, e.g., toxic, allergic, or immunological reactions, when administered to a subject.

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintegrants (e.g., potato starch or sodium starch glycolate), and the like. The compositions also can include stabilizers and preservatives. For examples of carriers, stabilizers and adjuvants, see, e.g., Martin, Remington's Pharmaceutical Sciences, 15th Ed., Mack Publ. Co., Easton, Pa. (1975), incorporated herein by reference in its entirety.

DETAILED DESCRIPTION

Provided herein are compositions comprising Sel1-derived peptides thereof, and method of use thereof for the treatment/prevention of excess oxalate levels and conditions and diseases related thereto. In particular, peptides comprise Sel-like repeat (SLR) domains and/or tetratricopeptide (TPR) domains and may be linked together or administered with other peptides or polypeptides to treat/prevent diseases/conditions related to excess oxalate levels, such as hyperoxaluria and/or hyperoxalemia.

Most kidney stones (KS) are composed of calcium oxalate, and small increases in urine oxalate affect the stone risk. The mammalian intestine plays a crucial role in oxalate homeostasis. Intestinal oxalate secretion mediated by anion exchanger SLC26A6 (A6) plays a major role in limiting net intestinal absorption of ingested oxalate; thereby preventing hyperoxaluria and calcium oxalate kidney stones (COKS). Hyperoxaluria and a high incidence of KS are commonly seen in IBD patients. Hyperoxaluria is also emerging as a major complication of bariatric surgery for obesity. Primary hyperoxaluria (PH) is an inherited disease in which there is endogenous oxalate overproduction. Enhancing intestinal oxalate secretion is expected to lead to reduced urine and plasma oxalate levels. In addition to degrading intraluminal dietary oxalate, the probiotic bacterium *Oxalobacter formigenes* (Of) also interacts with colonic epithelium by inducing colonic oxalate secretion, leading to reduced urinary excretion. Significant difficulties exist in sustaining Of colonization in animals and humans in the absence of high exogenous oxalate.

Sel1-like repeat (SLR) proteins (e.g. Sel1, Hrd3, Chs4, Nif1, PodJ, ExoR, AlgK, HcpA, Hsp12, EnhC, LpnE, MotX, and MerG) are involved in signal transduction pathways. SLR proteins (e.g., Sel1 proteins) have repeat units (e.g., repeat peptides). Most repeats are 5 to 40 amino acids (e.g., 5, 6, 7, 8, 9, 10, 11, 12, 13, 14, 15, 16, 17, 18, 19, 20, 21, 22, 23, 24, 26, 27, 28, 29, 30, 31, 32, 33, 34, 35, 36, 37, 38, 39, 40, or ranges therebetween), but longer repeat peptides (e.g., 45, 50, 55, 60, 65, 70, 75, 80, 85, 90, 95, 100, or longer or ranges therebetween) are within the scope of the SLR proteins (e.g., Sel1 proteins) herein. In some embodiments, repeat units fold into two to four secondary structural elements. In some embodiments, SLR proteins (e.g., Sel1 proteins) serve as adaptor proteins for the assembly of membrane-bound macromolecular complexes. Several bacterial and eukaryotic SLR proteins (e.g. Sel1 & Hrd3) are activated upon cellular stress. In some embodiments, Of Sel1 proteins are activated when oxalate is low in the culture medium (e.g., as evidenced by the observation of a CM of higher (>2-fold) bioactivity under this condition). Bacterial LpnE, EnhC, HcpA, ExoR, and AlgK proteins mediate the interactions between bacterial and eukaryotic host cells. In some embodiments, the SLR motif establishes a link between signal transduction pathways from eukaryotes and bacteria. In some embodiments, an SLR protein (e.g., Sel1 proteins) comprises leader sequences. In some embodiments, SLR proteins (e.g., Sel1 proteins) without leader sequences, such as PodJ or leaderless analogs of natural SLR proteins (e.g., Sel1 proteins), are active in the periplasmic space. In some embodiments, bacterial SLR proteins (e.g., Sel1 proteins), such as HcpA, ExoR, EnhC and LpnE are responsible for the adaptation of bacteria to different eukaryotic hosts.

Provided herein are compositions (e.g., Sel1-derived peptides, fusions of multiple Sel1-derived peptides, combinations of Sel1-derived peptides, fusions of Sel1-derived peptides with other peptides/polypeptides, etc.) which stimulate the clearance of oxalate (e.g., activate oxalate transport) from a biological environment (e.g., blood, urine, etc.). In some embodiments, compositions significantly reduce oxalate concentrations (e.g., urine oxalate, blood oxalate, etc.) for example, by at least 10%, 15%, 20%, 25%, 30%, 35%, 40%, 45%, 50%, 55%, 60%, 65%, 70%, 75%, 80%, 85%, 90%, 95%, or ranges therebetween. In some embodiments, compositions herein stimulate oxalate transport, thereby reducing in vivo oxalate levels in the blood (e.g., plasma oxalate levels), urine, etc., through mechanisms such as, for example, PKA activation and increased activity of SLC26 family members (e.g., SLC26A6) or other transporter(s); although embodiments herein are not limited to any particular mechanism of action and an understanding of the mechanism of action is not necessary to practice such embodiments.

In some embodiments, provided herein are compositions, kits, systems, and/or methods to treat, prevent, reduce the likelihood, treat/prevent a side effect of one or more of: hyperoxalemia, hyperoxaluria, nephrolithiasis, chronic kidney disease, end stage renal disease, calcium oxalate kidney stones, nephrocalcinosis, oxalate nephropathy, primary hyperoxaluria (PH), enteric hyperoxaluria (seen for example in IBD, following small bowel surgery or bariatric surgery, obesity, and celiac disease) and systemic oxalosis. In some embodiments, the reduction in oxalate levels and/or activation of oxalate transport is activated by compositions and methods described herein. In some embodiments, oxalate transport pathways are activated by the compositions and methods described herein. In some embodiments, compositions and methods are utilized in the treatment and/or prevention of hyperoxalemia, hyperoxaluria, and/or related diseases and conditions. In some embodiments, compositions and methods are utilized in screening for peptides and polypeptides useful in the treatment and/or prevention of hyperoxalemia, hyperoxaluria, and/or related diseases and conditions.

In some embodiments, provided herein are pharmaceutical compositions, SLR peptides (e.g., Sel1 peptides), TPR peptides (and fusions thereof), fusions of two or more Sel1-derived peptides (e.g., Sel1 peptides, Sel1 peptide analogs, etc.), fusions of Sel1-derived peptides (e.g., Sel1 peptides, Sel1 peptide analogs, etc.) with other peptides/polypeptides, nucleic acids encoding the peptides, proteins and polypeptides herein, molecular complexes of the foregoing, etc. for the treatment or prevention of hyperoxalemia, hyperoxaluria, and/or related diseases and conditions. In some embodiments, provided herein are peptides derived from (e.g., a fragment of, derived from a fragment of, etc.) SEQ ID NO: 2 or SEQ ID NO: 4. In some embodiments, peptides comprise at least 50% (e.g., 50%, 55%, 60%, 65%, 70%, 75%, 80%, 85%, 90%, 95%, less than 100%, 100%, or ranges therebetween) sequence identity to a portion of SEQ ID NO: 2 or SEQ ID NO: 4. In some embodiments, peptides comprise at least 50% (e.g., 50%, 55%, 60%, 65%, 70%, 75%, 80%, 85%, 90%, 95%, less than 100%, 100%, or ranges therebetween) sequence similarity to a portion of SEQ ID NO: 2 or SEQ ID NO: 4. In some embodiments, provided herein are peptides derived from (e.g., a fragment of, derived from a fragment of, etc.) SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO:

41, SEQ ID NO: 42, SEQ ID NO: 43, SEQ ID NO: 44, SEQ ID NO: 45, or SEQ ID NO: 46. In some embodiments, peptides comprise at least 50% (e.g., 50%, 55%, 60%, 65%, 70%, 75%, 80%, 85%, 90%, 95%, less than 100%, 100%, or ranges therebetween) sequence identity to all or a portion of SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, or SEQ ID NO: 46. In some embodiments, peptides comprise at least 50% (e.g., 50%, 55%, 60%, 65%, 70%, 75%, 80%, 85%, 90%, 95%, less than 100%, 100%, or ranges therebetween) sequence similarity to all or a portion of SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, or SEQ ID NO: 46.

In some embodiments, provided herein are fusions of two or more Sel1-derived peptides. In some embodiments, a fusion comprises a first peptide sequence derived from SEQ ID NOs: 1-46 linked directly or indirectly (via a linker or connector) to a second peptide sequence derived from SEQ ID NOs: 1-46. A fusion may additionally comprise one or more (e.g., 2, 3, 4, 5, 6, etc.) peptide sequence derived from SEQ ID NOs: 1-46 linked directly or indirectly. Embodiments are not limited by the combinations of various Sel1-derived peptides or the order in which they are fused.

In embodiments, a peptide/polypeptide/fusion provided herein is an artificial, not naturally-occurring, sequence. In some embodiments, a peptide/polypeptide/fusion described herein is prepared by methods known to those of ordinary skill in the art. For example, the peptide/polypeptide/fusion can be synthesized using solid phase polypeptide synthesis techniques (e.g. Fmoc or Boc chemistry). Alternatively, the peptide/polypeptide/fusion can be produced using recombinant DNA technology (e.g., using bacterial or eukaryotic expression systems). Further, a peptide/polypeptide/fusion may be expressed within a subject (e.g., following administration of an appropriate vector). Accordingly, to facilitate such methods, provided herein are genetic vectors (e.g., plasmids, viral vectors (e.g. AAV), etc.) comprising a sequence encoding the peptide/polypeptide/fusion, as well as host cells comprising such vectors. Furthermore, provided herein are the peptide/polypeptide/fusion produced via such methods.

In some embodiments, the administration of compositions described herein (e.g. Sel1 peptides, fusions of Sel1 peptides, variants and mimetics of Sel1-derived peptides, nucleic acids encoding Sel1-derived peptides, etc.) is provided. In some embodiments, provided herein is the administration of bioactive agents which reduce oxalate levels in vivo, or are otherwise described herein.

In some embodiments, a peptide is provided comprising or consisting of all or a portion of SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, or SEQ ID NO: 46. In some embodiments, a peptide is provided comprising at least 50% sequence identity to one of SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, or SEQ ID NO: 46. (e.g. at least 60% sequence identity, at least 70% sequence identity, at least 80% sequence identity, at least 90% sequence identity, at least 95% sequence identity, etc.). In some embodiments, a peptide comprises at least one substitution (e.g., 1, 2, 3, 4, 5, 6, 7, 8, 9, 10, 11, 12, 13, 14, 15, 16, 17, 18, 19, 20, or ranges therebetween (e.g., 1-10 substitutions)) from a Sel1 peptide sequence described herein (e.g., SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, or SEQ ID NO: 46.).

In some embodiments, a peptide/polypeptide is provided that is a fusion of two or more of SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, or SEQ ID NO: 46. In some embodiments, a peptide/polypeptide is provided that is a fusion of one or more peptides derived from (e.g., fragments of, comprising substitutions relative to, etc.) SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, or SEQ ID NO: 46. In some embodiments, a fusion comprises a portion (or portions) having one or more substitutions (e.g., 1, 2, 3, 4, 5, 6, 7, 8, 9, 10, 11, 12, 13, 14, 15, 16, 17, 18, 19, 20, or more) compared to SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, or SEQ ID NO: 46.

In some embodiments, fusions are provided comprising two or more (e.g., 2, 3, 4, 5, 6, 7, 8, 9, 10, or more) of the peptides herein or variants thereof. In some embodiments, a fusion may comprise multiple (e.g., 2, 3, 4, 5, 6, 7, 8, 9, 10, or more) copies of a single Sel1-derived peptide or variant thereof. In some embodiments, fusions comprise one or more (e.g., 2, 3, 4, 5, 6, 7, 8, 9, 10, or more) of the peptides herein or variants thereof and one or more non-Sel1-derived peptides or polypeptides. In some embodiments, a fusion may comprise a functional peptide or polypeptide segment. In some embodiments, the functional peptide or polypeptide segment comprises a signaling moiety, therapeutic moiety, localization moiety (e.g., cellular import signal, nuclear localization signal, etc.), detectable moiety (e.g., fluorescent moiety, contrast agent), or isolation/purification moiety (e.g., streptavidin, His$_6$, etc.). Such fusions may be expressed from a recombinant DNA which encodes the Sel1-derived peptide(s) and the additional peptide/polypeptide or may be formed by chemical synthesis. For instance, the fusion may comprise a Sel1-derived peptide(s) and an enzyme of interest, a luciferase, RNasin or RNase, and/or a channel protein (e.g., ion channel protein), a receptor, a membrane protein, a cytosolic protein, a nuclear protein, a structural protein, a phosphoprotein, a kinase, a signaling protein, a metabolic protein, a mitochondrial protein, a receptor associated protein, a fluorescent protein, an enzyme substrate, a transcription factor, selectable marker protein, nucleic acid binding protein, extracellular matrix protein, secreted protein, receptor ligand, serum protein, a protein with reactive cysteines, a transporter protein, a targeting sequence (e.g., a myristylation sequence), a mitochondrial localization sequence, or a nuclear localization sequence. The additional peptide/polypeptide may be fused to the N-terminus and/or the C-terminus of the Sel1-derived peptide(s). In one embodiment, the fusion protein comprises a first peptide/polypeptide at the N-terminus and another (different) peptide/polypeptide at the C-terminus of the Sel1-derived peptide(s). Optionally, the elements in the fusion are separated by a connector sequence, e.g., preferably one having at least 2 amino acid residues, such as one having 13 and up to 40 or 50 amino acid residues. In some embodiments, the presence of a connector sequence in a fusion protein of the invention does not substantially alter the function of either element (e.g., Sel1-derived peptide(s)) in the fusion relative to the function of each individual element, likely due to the connector sequence providing flexibility (autonomy) for each element in the fusion. In certain embodiments, the connector sequence is a sequence recognized by an enzyme or is photocleavable. For example, the connector sequence may include a protease recognition site.

In some embodiments, compositions are provided containing two or more unlinked peptides/polypeptides/fusions comprising SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, and SEQ ID NO: 46. In some embodiments, a composition is provided two or more peptides derived from (e.g., fragments of, comprising substitutions relative to, etc.) SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, and SEQ ID NO: 46. In some embodiments, a composition comprises two or more peptides comprising one or more substitutions (e.g., 1, 2, 3, 4, 5, 6, 7, 8, 9, 10, 11, 12, 13, 14, 15, 16, 17, 18, 19, 20, or more) compared to SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, and SEQ ID NO: 46.

Embodiments are not limited to the specific sequences listed herein. In some embodiments, peptides/polypeptides/fusions meeting limitations described herein and having substitutions not explicitly described are within the scope of embodiments here. In some embodiments, the peptides/polypeptides/fusions described herein are further modified (e.g., substitution, deletion, or addition of standard amino acids; chemical modification; etc.). Modifications that are understood in the field include N-terminal modification, C-terminal modification (which protects the peptide from proteolytic degradation), alkylation of amide groups, hydrocarbon "stapling" (e.g., to stabilize conformations). In some embodiments, the peptides/polypeptides described herein may be modified by conservative residue substitutions, for example, of the charged residues (K to R, R to K, D to E and E to D). Modifications of the terminal carboxy group include, without limitation, the amide, lower alkyl amide, constrained alkyls (e.g. branched, cyclic, fused, adamantyl) alkyl, dialkyl amide, and lower alkyl ester modifications. Lower alkyl is C1-C4 alkyl. Furthermore, one or more side groups, or terminal groups, may be protected by protective groups known to the ordinarily-skilled peptide chemist. The α-carbon of an amino acid may be mono- or dimethylated.

In some embodiments, peptides (or fusions thereof) are provided comprising: (i) one or more of the amino acid residues in the peptide are D-enantiomers, (ii) an N-terminally acetyl group, (iii) a deamidated C-terminal group, (iv) one or more unnatural amino acids, (v) one or more amino acid analogs, and/or (vi) one or more peptoid amino acids. In some embodiments, the peptide (or fusions thereof) or an amino acid therein comprises a modification selected from the group consisting of phosphorylation, glycosylation, ubiquitination, S-nitrosylation, methylation, N-acetylation, lipidation, lipoylation, deimination, eliminylation, disulfide bridging, isoaspartate formation, racemization, glycation; carbamylation, carbonylation, isopeptide bond formation, sulfation, succinylation, S-sulfonylation, S-sulfinylation, S-sulfenylation, S-glutathionylation, pyroglutamate formation, propionylation, adenylylation, nucleotide addition, iodination, hydroxylation, malonylation, butyrylation, amidation, C-terminal amidation, de-amidation, alkylation, acylation, biotinylation, carbamylation, oxidation, and pegylation. In some embodiments, the peptide exhibits enhanced stability relative to one of SEQ ID NOs: 5-46. In some embodiments, the peptide exhibits enhanced oxalate transport stimulation activity relative to one of SEQ ID NOs: 5-46.

In some embodiments, any embodiments described herein may comprise mimetics corresponding to Sel1-derived peptide and/or variants thereof, with various modifications that are understood in the field. In some embodiments, residues in the peptide sequences described herein may be substituted with amino acids having similar characteristics (e.g., hydrophobic to hydrophobic, neutral to neutral, etc.) or having other desired characteristics (e.g., more acidic, more hydrophobic, less bulky, more bulky, etc.). In some embodiments, non-natural amino acids (or naturally-occurring amino acids other than the standard 20 amino acids) are substituted in order to achieve desired properties.

In some embodiments, residues having a side chain that is positively charged under physiological conditions, or residues where a positively-charged side chain is desired, are substituted with a residue including, but not limited to: lysine, homolysine, 6-hydroxylysine, homoarginine, 2,4-diaminobutyric acid, 3-homoarginine, D-arginine, arginal (—COOH in arginine is replaced by —CHO), 2-amino-3-guanidinopropionic acid, nitroarginine (N(G)-nitroarginine), nitrosoarginine (N(G)-nitrosoarginine), methylarginine (N-methyl-arginine), c-N-methyllysine, allo-hydroxylysine, 2,3-diaminopropionic acid, 2,2'-diaminopimelic acid, ornithine, sym-dimethylarginine, asym-dimethylarginine, 2,6-diaminohexinic acid, p-aminobenzoic acid and 3-aminotyrosine and, histidine, 1-methylhistidine, and 3-methylhistidine.

A neutral residue is a residue having a side chain that is uncharged under physiological conditions. A polar residue preferably has at least one polar group in the side chain. In some embodiments, polar groups are selected from hydroxyl, sulfhydryl, amine, amide and ester groups or other groups which permit the formation of hydrogen bridges.

In some embodiments, residues having a side chain that is neutral/polar under physiological conditions, or residues where a neutral side chain is desired, are substituted with a residue including, but not limited to: asparagine, cysteine, glutamine, serine, threonine, tyrosine, citrulline, N-methylserine, homoserine, allo-threonine and 3,5-dinitro-tyrosine, and β-homoserine.

Residues having a non-polar, hydrophobic side chain are residues that are uncharged under physiological conditions, preferably with a hydropathy index above 0, particularly above 3. In some embodiments, non-polar, hydrophobic side chains are selected from alkyl, alkylene, alkoxy, alkenoxy, alkylsulfanyl and alkenylsulfanyl residues having from 1 to 10, preferably from 2 to 6, carbon atoms, or aryl residues having from 5 to 12 carbon atoms. In some embodiments, residues having a non-polar, hydrophobic side chain are, or residues where a non-polar, hydrophobic side chain is desired, are substituted with a residue including, but not limited to: leucine, isoleucine, valine, methionine, alanine, phenylalanine, N-methylleucine, tert-butylglycine, octylglycine, cyclohexylalanine, β-alanine, 1-aminocyclohexylcarboxylic acid, N-methylisoleucine, norleucine, norvaline, and N-methylvaline.

In some embodiments, peptide and polypeptides are isolated and/or purified (or substantially isolated and/or substantially purified). Accordingly, in such embodiments, peptides and/or polypeptides are provided in substantially isolated form. In some embodiments, peptides and/or polypeptides are isolated from other peptides and/or polypeptides as a result of solid phase peptide synthesis, for example. Alternatively, peptides and/or polypeptides can be substantially isolated from other proteins after cell lysis from recombinant production. Standard methods of protein purification (e.g., HPLC) can be employed to substantially purify peptides and/or polypeptides. In some embodiments, the present invention provides a preparation of peptides and/or polypeptides in a number of formulations, depending on the desired use. For example, where the polypeptide is substantially isolated (or even nearly completely isolated from other proteins), it can be formulated in a suitable medium solution for storage (e.g., under refrigerated conditions or under frozen conditions). Such preparations may contain protective agents, such as buffers, preservatives, cryprotectants (e.g., sugars such as trehalose), etc. The form of such preparations can be solutions, gels, etc. In some embodiments, peptides and/or polypeptides are prepared in lyophilized form. Moreover, such preparations can include other desired agents, such as small molecules or other peptides, polypeptides or proteins. Indeed, such a preparation comprising a mixture of different embodiments of the peptides and/or polypeptides described here may be provided.

In some embodiments, provided herein are peptidomimetic versions of the peptide sequences described herein or variants thereof. In some embodiments, a peptidomimetic is characterized by an entity that retains the polarity (or non-polarity, hydrophobicity, etc.), three-dimensional size, and functionality (bioactivity) of its peptide equivalent but wherein all or a portion of the peptide bonds have been replaced (e.g., by more stable linkages). In some embodiments, 'stable' refers to being more resistant to chemical degradation or enzymatic degradation by hydrolytic enzymes. In some embodiments, the bond which replaces the amide bond (e.g., amide bond surrogate) conserves some properties of the amide bond (e.g., conformation, steric bulk, electrostatic character, capacity for hydrogen bonding, etc.). Cyclization (head-to-tail, head/tail-to-side-chain, and/or side-chain-to-side-chain) enhances peptide stability and permeability by introducing conformation constraint, thereby reducing peptide flexibility, and a cyclic enkephalin analog is highly resistant to enzymatic degradation. Chapter 14 of "Drug Design and Development", Krogsgaard, Larsen, Liljefors and Madsen (Eds) 1996, Horwood Acad. Publishers provides a general discussion of techniques for the design and synthesis of peptidomimetics and is herein incorporated by reference in its entirety. Suitable amide bond surrogates include, but are not limited to: N-alkylation (Schmidt, R. et al., Int. J. Peptide Protein Res., 1995, 46,47; herein incorporated by reference in its entirety), retro-inverse amide (Chorev, M. and Goodman, M., Acc. Chem. Res, 1993, 26, 266; herein incorporated by reference in its entirety), thioamide (Sherman D. B. and Spatola, A. F. J. Am. Chem. Soc., 1990, 112, 433; herein incorporated by reference in its entirety), thioester, phosphonate, ketomethylene (Hoffman, R. V. and Kim, H. O. J. Org. Chem., 1995, 60, 5107; herein incorporated by reference in its entirety), hydroxymethylene, fluorovinyl (Allmendinger, T. et al., Tetrahydron Lett., 1990, 31, 7297; herein incorporated by reference in its entirety), vinyl, methyleneamino (Sasaki, Y and Abe, J. Chem. Pharm. Bull. 1997 45, 13; herein incorporated by reference in its entirety), methylenethio (Spatola, A. F., Methods Neurosci, 1993, 13, 19; herein incorporated by reference in its entirety), alkane (Lavielle, S. et. al., Int. J. Peptide Protein Res., 1993, 42, 270; herein incorporated by reference in its entirety) and sulfonamido (Luisi, G. et al. Tetrahedron Lett. 1993, 34, 2391; herein incorporated by reference in its entirety).

As well as replacement of amide bonds, peptidomimetics may involve the replacement of larger structural moieties with di- or tripeptidomimetic structures and in this case, mimetic moieties involving the peptide bond, such as azole-derived mimetics may be used as dipeptide replacements. Suitable peptidomimetics include reduced peptides where the amide bond has been reduced to a methylene amine by treatment with a reducing agent (e.g. borane or a hydride reagent such as lithium aluminum-hydride); such a reduction has the added advantage of increasing the overall cationicity of the molecule.

Other peptidomimetics include peptoids formed, for example, by the stepwise synthesis of amide-functionalised polyglycines. Some peptidomimetic backbones will be readily available from their peptide precursors, such as peptides which have been permethylated, suitable methods are described by Ostresh, J. M. et al. in Proc. Natl. Acad. Sci. USA (1994) 91, 11138-11142; herein incorporated by reference in its entirety.

In some embodiments, provided herein are pharmaceutical compositions comprising of one or more Sel1-derived peptides or fusions or variants thereof and a pharmaceutically acceptable carrier. Any carrier which can supply an active peptide or polypeptide (e.g., without destroying the peptide or polypeptide within the carrier) is a suitable carrier, and such carriers are well known in the art. In some embodiments, compositions are formulated for administration by any suitable route, including but not limited to, orally (e.g., such as in the form of tablets, capsules, granules or powders), sublingually, bucally, parenterally (such as by subcutaneous, intravenous, intramuscular, intradermal, or intracisternal injection or infusion (e.g., as sterile injectable aqueous or non-aqueous solutions or suspensions, etc.)), nasally (including administration to the nasal membranes, such as by inhalation spray), topically (such as in the form of a cream or ointment), transdermally (such as by transdermal patch), rectally (such as in the form of suppositories), etc.

In some embodiments, provided herein are methods for treating patients suffering from (or at risk of) hyperoxaluria, hyperoxalemia, and/or in need of treatment (or preventative therapy). In some embodiments, a pharmaceutical composition comprising at least one Sel1-derived peptide described herein (or fusions or variants thereof) is delivered to such a patient in an amount and at a location sufficient to treat the condition. In some embodiments, peptides and/or polypeptides (or pharmaceutical composition comprising such) can be delivered to the patient systemically or locally, and it will be within the ordinary skill of the medical professional treating such patient to ascertain the most appropriate delivery route, time course, and dosage for treatment. It will be appreciated that application methods of treating a patient most preferably substantially alleviates or even eliminates such symptoms; however, as with many medical treatments, application of the inventive method is deemed successful if, during, following, or otherwise as a result of the inventive method, the symptoms of the disease or disorder in the patient subside to an ascertainable degree.

A pharmaceutical composition may be administered in the form which is formulated with a pharmaceutically acceptable carrier and optional excipients, adjuvants, etc. in accordance with good pharmaceutical practice. The Sel1-derived peptide (or fusions or variants thereof) pharmaceutical composition may be in the form of a solid, semi-solid or liquid dosage form: such as powder, solution, elixir, syrup, suspension, cream, drops, paste and spray. As those skilled in the art would recognize, depending on the chosen route of administration (e.g. pill, injection, etc.), the composition form is determined. In general, it is preferred to use a unit dosage form in order to achieve an easy and accurate administration of the active pharmaceutical peptide or polypeptide. In general, the therapeutically effective pharmaceutical compound is present in such a dosage form at a concentration level ranging from about 0.5% to about 99% by weight of the total composition, e.g., in an amount sufficient to provide the desired unit dose. In some embodiments, the pharmaceutical composition may be administered in single or multiple doses. The particular route of administration and the dosage regimen will be determined by one of skill in keeping with the condition of the individual to be treated and said individual's response to the treatment. In some embodiments, Sel1-derived peptide described herein (or fusions or variants thereof) pharmaceutical composition is provided in a unit dosage form for administration to a subject, comprising one or more nontoxic pharmaceutically acceptable carriers, adjuvants or vehicles. The amount of the active ingredient that may be combined with such materials to produce a single dosage form will vary depending upon various factors, as indicated above. A variety of materials can be used as carriers, adjuvants and vehicles in the composition of the invention, as available in the pharmaceutical art. Injectable preparations, such as oleaginous solutions, suspensions or emulsions, may be formulated as known in the art, using suitable dispersing or wetting agents and suspending agents, as needed. The sterile injectable preparation may employ a nontoxic parenterally acceptable diluent or solvent such as sterile nonpyrogenic water or 1,3-butanediol. Among the other acceptable vehicles and solvents that may be employed are 5% dextrose injection, Ringer's injection and isotonic sodium chloride injection (as described in the USP/NF). In addition, sterile, fixed oils may be conventionally employed as solvents or suspending media. For this purpose, any bland fixed oil may be used, including synthetic mono-, di- or triglycerides. Fatty acids such as oleic acid can also be used in the preparation of injectable compositions.

In various embodiments, the peptides disclosed herein are derivatized by conjugation to one or more polymers or small molecule substituents.

In certain of these embodiments, the Sel1-derived peptides described herein (or fusions or variants thereof) are derivatized by coupling to polyethylene glycol (PEG). Coupling may be performed using known processes. See, Int. J. Hematology, 68:1 (1998); Bioconjugate Chem., 6:150 (1995); and Crit. Rev. Therap. Drug Carrier Sys., 9:249 (1992) all of which are incorporated herein by reference in their entirety. Those skilled in the art, therefore, will be able to utilize such well-known techniques for linking one or more polyethylene glycol polymers to the peptides and polypeptides described herein. Suitable polyethylene glycol polymers typically are commercially available or may be made by techniques well known to those skilled in the art. The polyethylene glycol polymers preferably have molecular weights between 500 and 20,000 and may be branched or straight chain polymers.

The attachment of a PEG to a peptide or polypeptide described herein can be accomplished by coupling to amino, carboxyl or thiol groups. These groups will typically be the N- and C-termini and on the side chains of such naturally occurring amino acids as lysine, aspartic acid, glutamic acid and cysteine. Since the peptides and polypeptides of the present disclosure can be prepared by solid phase peptide chemistry techniques, a variety of moieties containing diamino and dicarboxylic groups with orthogonal protecting groups can be introduced for conjugation to PEG.

The present disclosure also provides for conjugation of the Sel1-derived peptides described herein (or fusions or variants thereof) to one or more polymers other than polyethylene glycol.

In some embodiments, the Sel1-derived peptides described herein (or fusions or variants thereof) are derivatized by conjugation or linkage to, or attachment of, polyamino acids (e.g., poly-his, poly-arg, poly-lys, etc.) and/or fatty acid chains of various lengths to the N- or C-terminus or amino acid residue side chains. In certain embodiments, the peptides and polypeptides described herein are derivatized by the addition of polyamide chains, particularly polyamide chains of precise lengths, as described in U.S. Pat. No. 6,552,167, which is incorporated by reference in its entirety. In yet other embodiments, the peptides and polypeptides are modified by the addition of alkylPEG moieties as described in U.S. Pat. Nos. 5,359,030 and 5,681,811, which are incorporated by reference in their entireties.

In select embodiments, the Sel1-derived peptides described herein (or fusions or variants thereof) are derivatized by conjugation to polymers that include albumin and gelatin. See, Gombotz and Pettit, Bioconjugate Chem., 6:332-351, 1995, which is incorporated herein by reference in its entirety.

In further embodiments, the Sel1-derived peptides described herein (or fusions or variants thereof) are conjugated or fused to immunoglobulins or immunoglobulin fragments, such as antibody Fc regions.

In some embodiments, the pharmaceutical compositions described herein (e.g., comprising the Sel1-derived peptides described herein (or fusions or variants thereof) find use in the treatment and/or prevention of hyperoxaluria, hyperoxalemia, and related conditions. In some embodiments, the compositions are administered to a subject. In certain embodiments, the patient is an adult. In other embodiments, the patient is a child.

In various embodiments, the Sel1-derived peptides described herein (or fusions or variants thereof) are administered in an amount, on a schedule, and for a duration sufficient to decrease triglyceride levels by at least 5%, 10%, 15%, 20% or 25% or more as compared to levels just prior to initiation of treatment. In some embodiments, the Sel1-derived peptides described herein (or fusions or variants thereof) are administered in an amount, on a dosage schedule, and for a duration sufficient to decrease oxalate levels (e.g., in urine, in plasma) by at least 10%, 15%, 20%, 25%, 30%, 35%, 40%, 45% or 50%. In particular embodiments, the Sel1-derived peptides described herein (or fusions or variants thereof) are administered in an amount, on a schedule, and for a time sufficient to decrease oxalate levels (e.g., in urine, in plasma) by at least 55%, 60%, 65%, even at least about 70% or more.

In certain embodiments, the Sel1-derived peptides described herein (or fusions or variants thereof) are administered in an amount, expressed as a daily equivalent dose regardless of dosing frequency, of 50 micrograms ("mcg") per day, 60 mcg per day, 70 mcg per day, 75 mcg per day, 100 mcg per day, 150 mcg per day, 200 mcg per day, or 250 mcg per day. In some embodiments, the Sel1-derived peptides described herein (or fusions or variants thereof) are administered in an amount of 500 mcg per day, 750 mcg per day, or 1 milligram ("mg") per day. In yet further embodiments, the Sel1-derived peptides described herein (or fusions or variants thereof) are administered in an amount, expressed as a daily equivalent dose regardless of dosing frequency, of 1-10 mg per day, including 1 mg per day, 1.5 mg per day, 1.75 mg per day, 2 mg per day, 2.5 mg per day, 3 mg per day, 3.5 mg per day, 4 mg per day, 4.5 mg per day, 5 mg per day, 5.5 mg per day, 6 mg per day, 6.5 mg per day, 7 mg per day, 7.5 mg per day, 8 mg per day, 8.5 mg per day, 9 mg per day, 9.5 mg per day, or 10 mg per day.

In various embodiments, the Sel1-derived peptides described herein (or fusions or variants thereof) are administered on a monthly, biweekly, weekly, daily ("QD"), or twice a day ("BID") dosage schedule. In other embodiments, the peptide/polypeptide is administered. In typical embodiments, the peptide/polypeptide is administered for at least 3 months, at least 6 months, at least 12 months, or more. In some embodiments, Sel1-derived peptides described herein (or fusions or variants thereof) are administered for at least 18 months, 2 years, 3 years, or more.

EXPERIMENTAL

Of-derived factors are secreted in its culture conditioned medium (CM) that significantly stimulate (>2.8-fold) oxalate transport by human intestinal Caco2-BBE (C2) cells through PKA activation and stimulation of the oxalate transporters SLC26A6 (A6) and SLC26A2 (A2). In vivo, rectal administration of Of CM reduced urinary oxalate excretion >32.5% in hyperoxaluric mice, and stimulated colonic oxalate secretion >42%, reflecting the therapeutic impact of these factors. Multiple Sel1 proteins are involved in protein-protein interactions and signal transduction pathways as the major Of-derived factors. These Sel1 proteins closely recapitulate the effects of the Of-derived factors and similarly stimulate (1.4-2.4-fold) oxalate transport by C2 cells via PKA and the A2/A6 transporters. 35-amino acid peptides (P7-10) within a Sel1 protein are identified which significantly stimulate (1.5-fold individually and >2.4-fold by P8+9) oxalate transport by C2 cells. P8+9 peptides also significantly stimulated oxalate transport by human sigmoid colon (1.8-fold), distal colon (1.7-fold), and ileum (2-fold) organoids (ex vivo intestinal epithelia models fully mimicking the in vivo physiological responses), indicating that P8+9 peptides will stimulate oxalate transport in human colonic and ileal epithelia in vivo. Therefore, the identification and characterization of the active motifs responsible for colonic oxalate transport provides an effective drug for reducing plasma and urine oxalate levels.

Sel1 (sel: suppressor-enhancer of lin) proteins are identified as the major Of-derived secreted factors. Sel1 proteins are in the family of solenoid proteins, distinguishable from general globular proteins by the presence of intra-molecular sequence similarities (repeats) that lead to their modular architectures (Ref. 25; incorporated by reference in its entirety). A cross-genome analysis of repeats revealed an a/a-repeat consisting of 36 to 44 amino acids called Sel1-like repeat (SLR). SLR proteins (e.g. Sel1, Hrd3, etc.) are involved in protein-protein interactions and signal transduction pathways (Ref. 25; incorporated by reference in its entirety) and the latter is important since CM stimulates oxalate transport through PKA activation. SLR proteins serve as adaptor proteins for the assembly of membrane-bound macromolecular complexes (Ref. 25; incorporated by reference in its entirety), which might include oxalate transporters (e.g. A6) and other regulatory proteins. Several bacterial and eukaryotic SLR proteins (e.g. Sel1) are activated upon cellular stress (Ref. 25; incorporated by reference in its entirety), which of significant interest since Of Sel1 proteins might be activated when oxalate is limited given the observation of >2-fold higher stimulatory effects from the CM under this condition (Ref. 4; incorporated by reference in its entirety). The Of genome has 44 Sel1 genes, which are significantly over-represented and reflects the importance of Sel1 proteins for Of. The dependence of Of on oxalate for viability might explain why it has 44 Sel1 proteins, and it is possible that Of utilizes Sel1 proteins to derive oxalate from blood by inducing colonic secretion, as observed with CM, to sustain its survival when dietary oxalate is limited. Supporting this notion, SLR proteins mediate the interactions between bacterial and eukaryotic host cells and establishes a link between signal transduction pathways from eukaryotes and bacteria. Most of the 44 Sel1 proteins have signal peptides and therefore are secreted proteins. SLR proteins are involved in the ER-associated protein degradation (ERAD) and may also be responsible for the adaptation of bacteria to different eukaryotic hosts.

Experiments conducted during development of embodiments herein demonstrated that certain Sel1 proteins (e.g., 301, 310, 318, and 321) are capable of significantly stimulating oxalate transport by cells (See, PCT/US18/14494; herein incorporated by reference in its entirety). Sel1 proteins 301 and 318 have been demonstrated to be the most potent stimulators of oxalate transport in human Caco2-BBE (C2) cells, and are predicted to have six (P1-P6; Table 1) and five (P7-P11; Table 2) SLR domains (each 30-35 amino acids in length and called peptides here), respectively.

TABLE 1

Predicted 301 SLR domains

| | | |
|---|---|---|
| P1 | ADAQNRLGIAYRYGTGVRKNPALSVKWLEKAAKQG | SEQ ID NO: 5 |
| P2 | QYNLGVAYYYGRGIKKDFSEAVSWYKKSAE | SEQ ID NO: 6 |
| P3 | AYHNLGTAYYDGIGVDKNPHEAVRWWKKAAELG | SEQ ID NO: 7 |
| P4 | QSQYNLGIAYEEGWGAEKNPENAVFWYRKAAEQGH | SEQ ID NO: 8 |
| P5 | ARAQFNLGKTFYIGAGINKNTDKAVYWFIKAANQG | SEQ ID NO: 9 |
| P6 | ESQNNLGALYNDGNGVDRDYQEAVFWYRKSALQGD | SEQ ID NO: 10 |

TABLE 2

Predicted 318 SLR domains

| | | |
|---|---|---|
| P7 | EAQYNMGYHYAEGKGVPRDQGKAVFWYEKAAAAGD | SEQ ID NO: 11 |
| P8 | DAQYMLGAMSVEGIGLPKDSQVALTWLSKAAAQGD | SEQ ID NO: 12 |
| P9 | AKAQYGLGILYAKGQGVAPDQEKALILYRMAATQG | SEQ ID NO: 13 |
| P10 | ATAEYAVGLAYAYGRGTAQNDVKAADWFEAAAQQG | SEQ ID NO: 14 |
| P11 | EAQRRWALMLASGRGVAKNEGEALKWFKKAAVAGD | SEQ ID NO: 15 |

Sel1 proteins 310, 301 (from the human strain OXCC13), 317, 319, 321, 304, and 322 also contain predicted SLR domains (Tables 3-9).

TABLE 3

Predicted 310 SLR domains

| | | |
|---|---|---|
| P12 | ALAQSNLGVLYASGRGVESSPKRALEWYKKAAVQGN | SEQ ID NO: 16 |
| P13 | SQAQFSLGNMYEDGSGVEKNLAVAAAWYQKSAEQGN | SEQ ID NO: 17 |
| P14 | AEAQTNLGVLYSYGLGVDKDLSKAFYWY | SEQ ID NO: 18 |
| P15 | ESQDRLGLMLTNGVGVKQDYKQAYSWFRKAARQG | SEQ ID NO: 19 |
| P16 | AESQNNLGVLYARGLGVEKDYKQAVAWYRKA | SEQ ID NO: 20 |
| P17 | QAQFNLGTMYLQGHGVKQDVKQARHWFTKAAAQ | SEQ ID NO: 21 |

TABLE 4

Predicted 301 (human strain OXCC13) SLR domains

| | | |
|---|---|---|
| P1H | AQAQHNLGVTYYEGEGIKKDYAKAVYWWKKAAEQG | SEQ ID NO: 22 |
| P2H | PQSQYNLGIAYEEGWGAEKNPENAVFWYRKAAEQGH | SEQ ID NO: 23 |
| P3H | EAQAYIGMIYFKGKYVAKNEKKGFYWLKKAAEKDS | SEQ ID NO: 24 |

TABLE 5

Predicted 317 SLR domains

| | |
|---|---|
| ALYGLGVMATNGLGMPRNDEKALVWFREGAAKG | SEQ ID NO: 25 |
| EAQFGLGAMYDLSRGVRQDMTLAIDWYEKSARAG | SEQ ID NO: 26 |

TABLE 6

Predicted 319 SLR domains

| | |
|---|---|
| QLYLGLMYGHGKGVPRDLNKSLFWVEKAADRG | SEQ ID NO: 27 |
| AQYLMGMAYLEGKSVPQDLPVAAAWFYKAAMQGN | SEQ ID NO: 28 |
| ADAQLRLGYMYARGIGVPVDKPKAVAWLEKAASAGN | SEQ ID NO: 29 |

TABLE 7

Predicted 321 SLR domains

| | |
|---|---|
| GSMLSQGKGVEKDPKKGLEWFVQAGQDGD | SEQ ID NO: 30 |
| SEAQQMMGFLYGEGWGAKRDPVKAEYWFDKAAASGD | SEQ ID NO: 31 |

TABLE 8

Predicted 304 SLR domains

| | |
|---|---|
| QAEHEMGSLYLMGIGVAQSNVMAVAWYRKAAIQG | SEQ ID NO: 32 |
| APSQTAMGYAYEEGAGVPQDADLARYWFDKAAAQGN | SEQ ID NO: 33 |

TABLE 9

Predicted 322 SLR domains

| | |
|---|---|
| AQAGLGWMYAAGRGVNKDETLSFSWYERAAVAG | SEQ ID NO: 34 |
| AQYMLGRYYEKGIGVAKDRVLAKEWYEKAAAQGN | SEQ ID NO: 35 |

Also identified herein are tetratricopeptide repeat (TPR) sequences. A TPR is a structural motif comprising a degenerate 34 amino acid sequence. The TPR sequences identified herein (Table 10) and variants and mimetics thereof find use in the embodiments described herein (e.g., in place of SLR peptides, with SLR peptides, etc.).

TABLE 10

Predicted TPR sequences

| | | |
|---|---|---|
| TRP1 | KAAKSGNAEAQYLFGMLVYDGRGVQQDNCVAMLW WMKAAEQNHAKALVMLGNLHRKGQCIAENYPKAIA YWKRAAVQNNV | SEQ ID NO: 36 |
| TRP2 | LGTAYYDGIGVDKNPHEAVRWWKKAAELGFPESQN NLGALYNDGNGVDRDYQEAVFWYRKSALQGDELG QYNLGVAYYGRGIKKDFSEAVSWYKKSAE | SEQ ID NO: 37 |

TABLE 10-continued

Predicted TPR sequences

| TRP3 | YRKAAEQGHADAQNRLGIAYRYGTGVRKNPALSVK WLEKAAKQGLARAQFNLGKTFYIGAGINKNTDKAV YWFIKAANQGFTEAQAY | SEQ ID NO: 38 |
|------|---|---|

Experiments were conducted during development of embodiments herein to determine whether individual Sel1 301 SLR peptides and/or combinations of multiple Sel1 301 SLR peptides are capable of stimulating oxalate influx into human Caco2-BBE (C2) cells. Significant stimulation of $^{14}$C-oxalate influx into human C2 cells was observed (FIG. 1).

Figure 2:
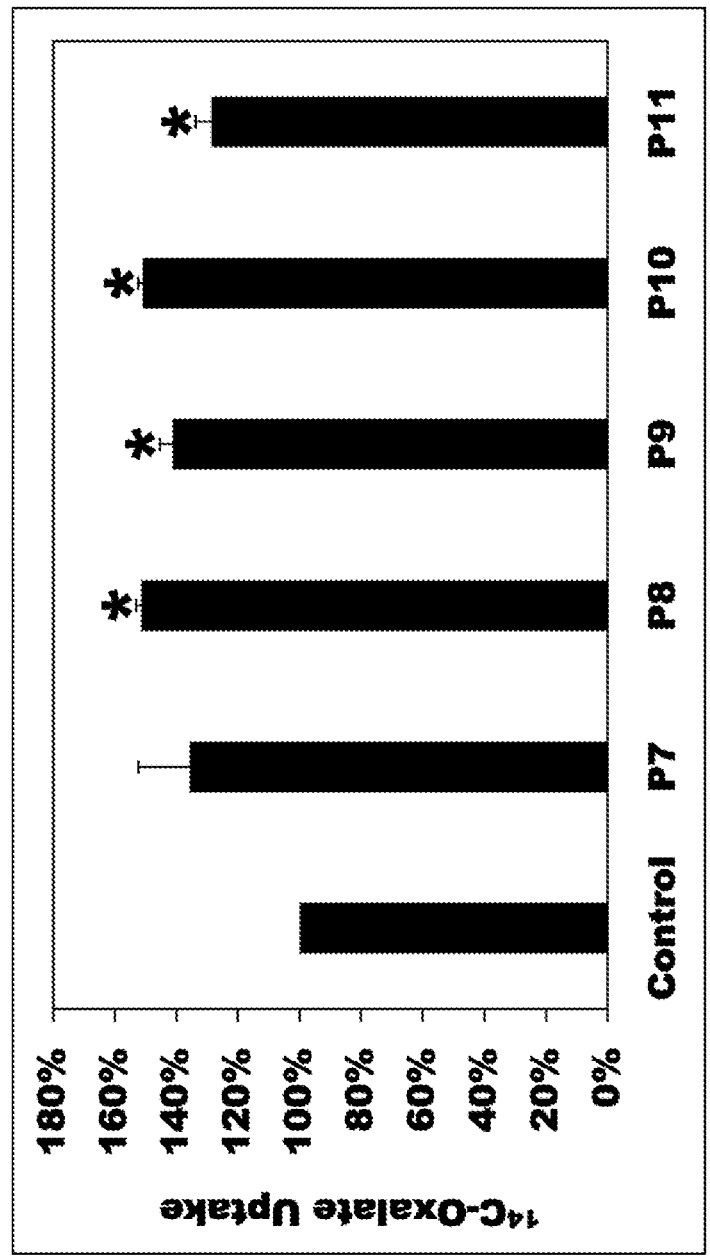
FIG. 2. Several 318-derived peptides significantly stimulate $^{14}C$-oxalate influx into C2 cells.

Sel1 318 is the only Sel1 protein identified by mass spectroscopic analysis of the human *Oxalobacter formigenes* (Of) strain OXCC13 genome using a stringent search (Maxquant: 20 ppm, with additional filtering at 1% FDR); several Sel1 proteins are identified by a less stringent search. Sel1 318 is separated by 3 genes from 5 other Sel1 genes located together in a potential operon (304/319-322); Sel1 318 is also a few genes away from Sel1 317 and Sel1 310, which are located near each other. Collectively, these observations indicate that Sel1 318 a key Sel1 protein for Of. Several Sel1 318-derived peptides individually stimulate 14C-oxalate influx into Caco2-BBE cells (FIG. 2).

Figure 8:
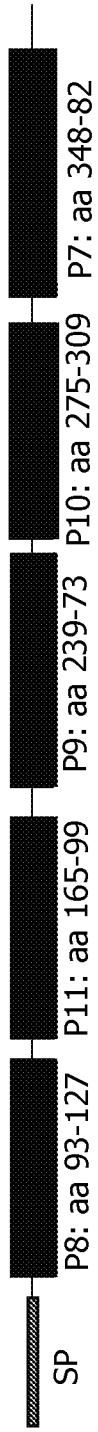
FIG. 8. 318 Sel1 protein. SP=signal peptide. Boxes=SLR motifs and they represent P7-11 peptides.
Figure 9:
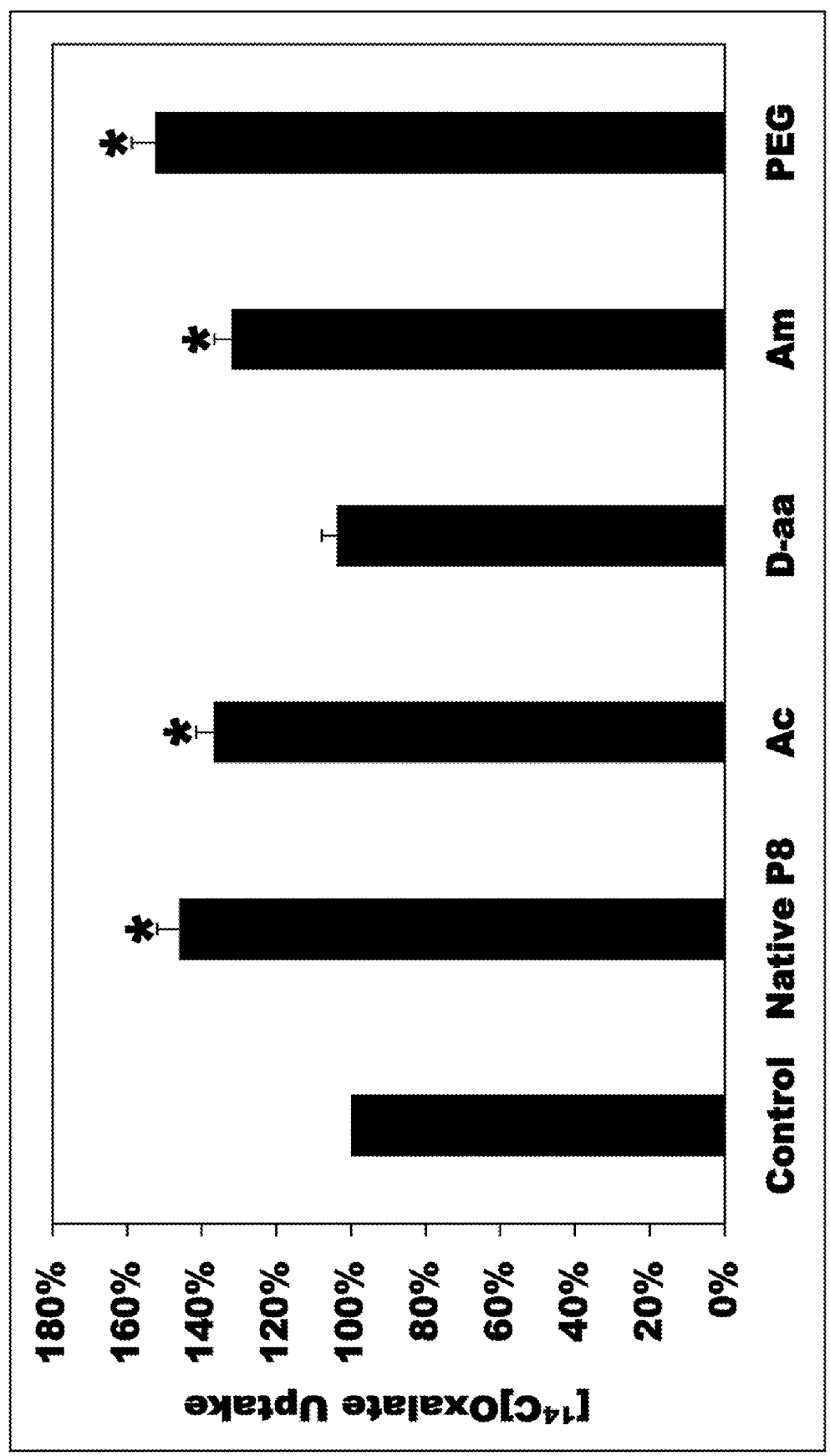
FIG. 9. Compared with native P8 peptide, P8 with N-terminal acetylation (Ac), C-terminal amidation (Am), all glycines replaced with PEG6 significantly stimulate 14C-oxalate influx into Caco2-BBE cells. Replacing natural amino acids with D-amino acids (D-aa) produces a nonfunctional P8 peptide.
Figure 10:
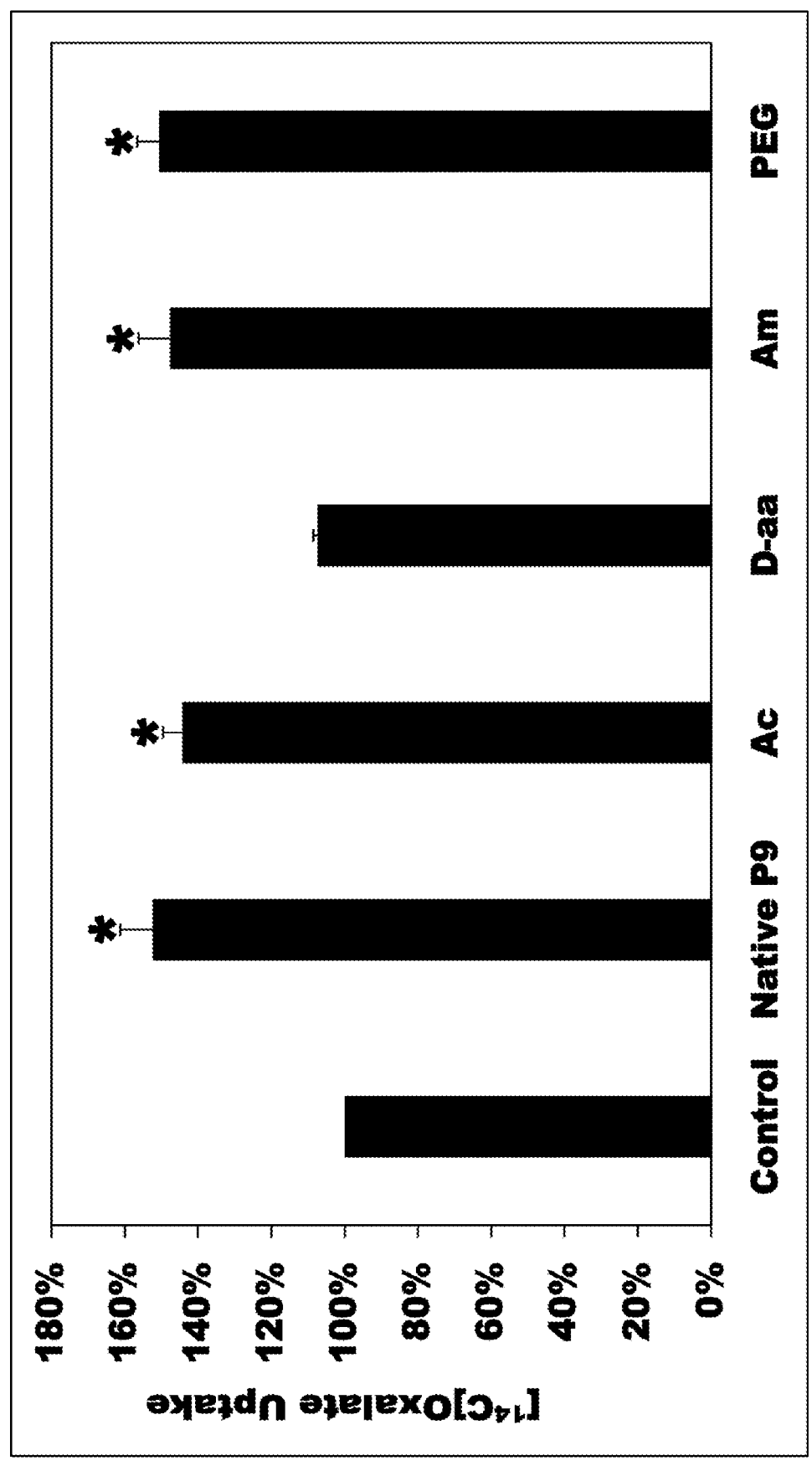
FIG. 10. Compared with native P9 peptide, P9 with N-terminal acetylation (Ac), C-terminal amidation (Am), all glycines replaced with PEG6 significantly stimulate 14C-oxalate influx into Caco2-BBE cells. Replacing natural amino acids with D-amino acids (D-aa) produces a nonfunctional P9 peptide.
Figure 11:
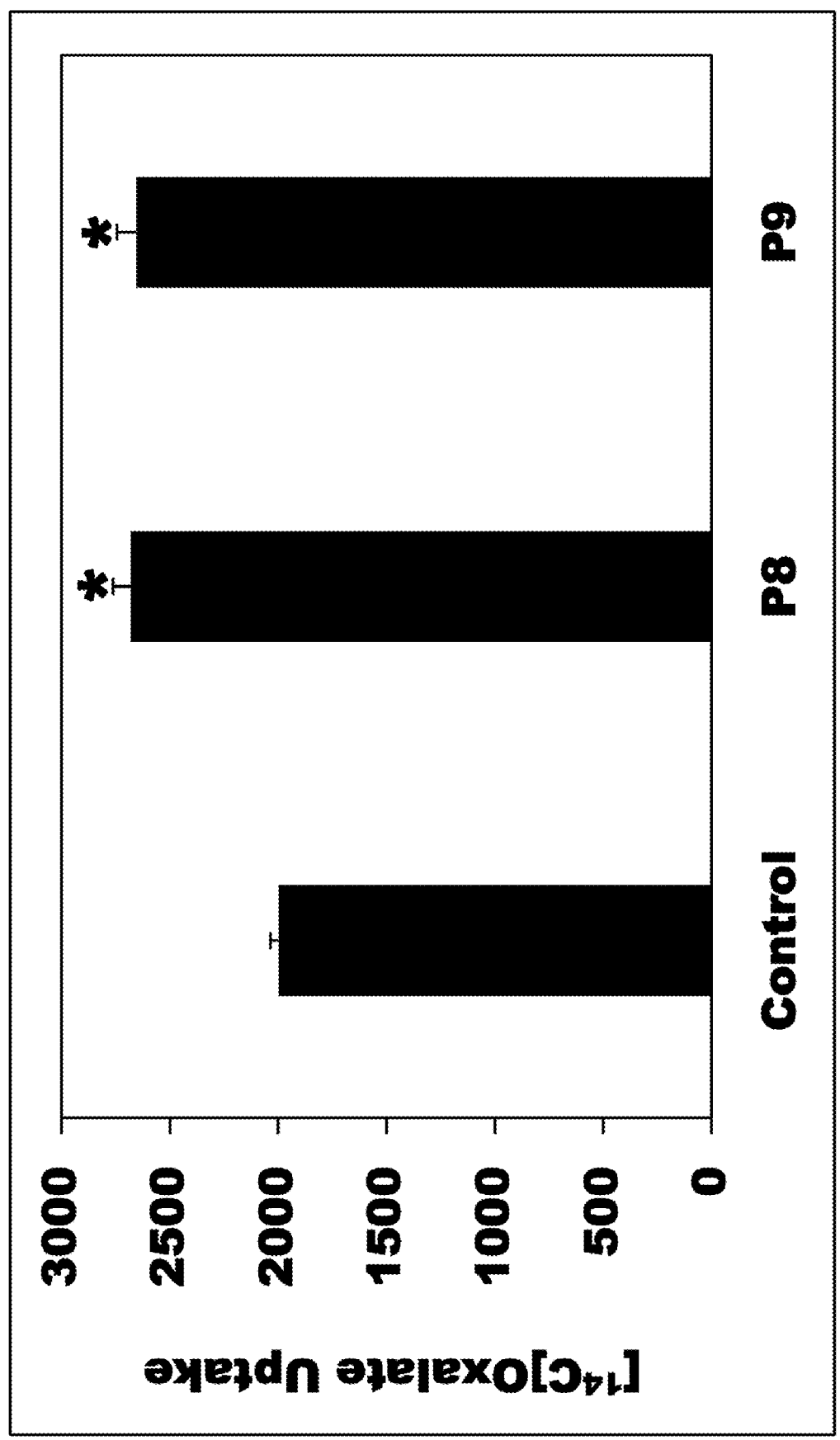
FIG. 11. P8 with G15 replaced with D-alanine and P9 with G16 replaced with D-alanine significantly stimulate $^{14}C$-oxalate influx into Caco2-BBE cells.
Figure 12:
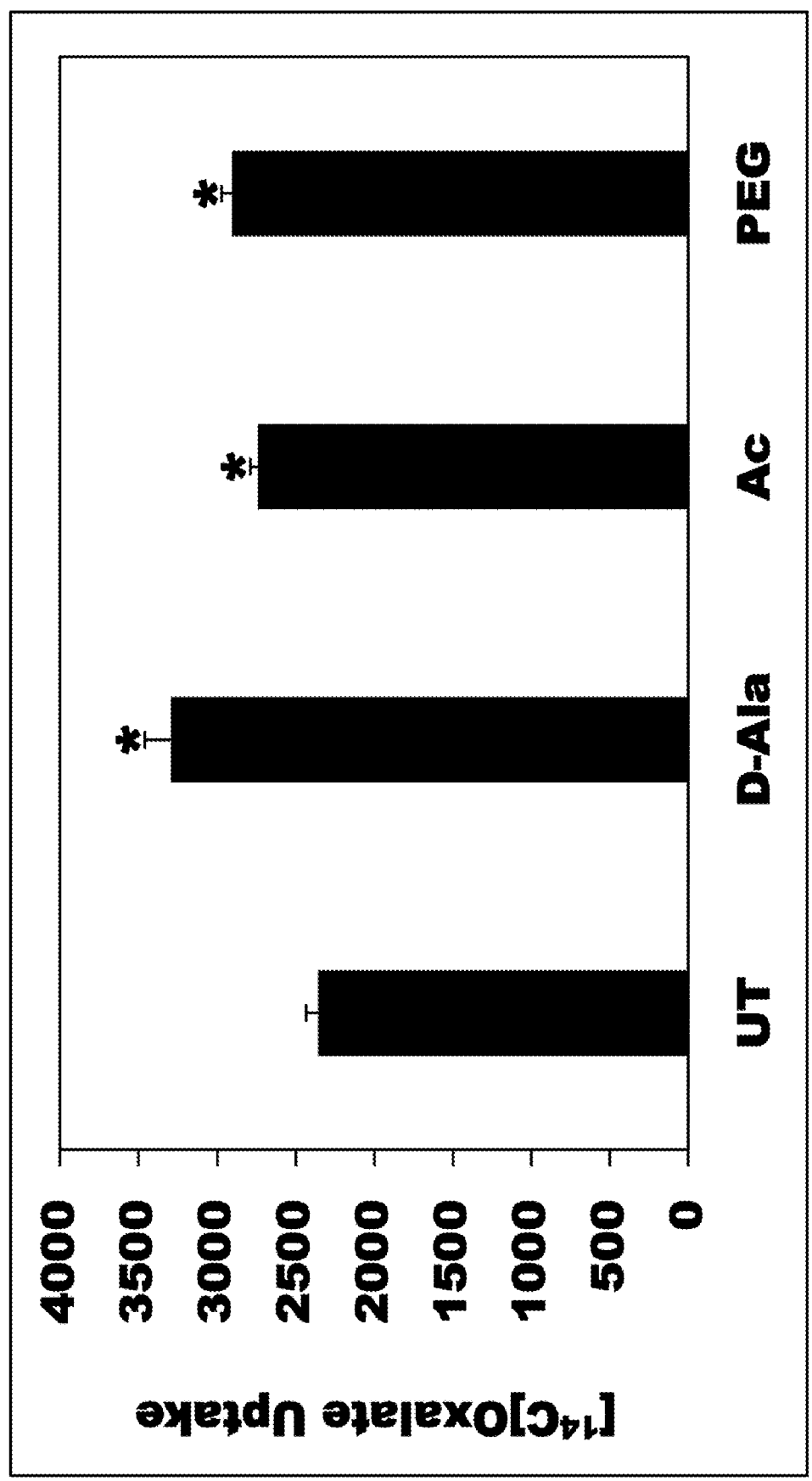
FIG. 12. P9 with N-terminal acetylation (Ac), C-terminal amidation (Am), and G16 replaced with D-alanine (D-Ala) significantly stimulate oxalate transport by a human distal colon organoid.
Figure 13:
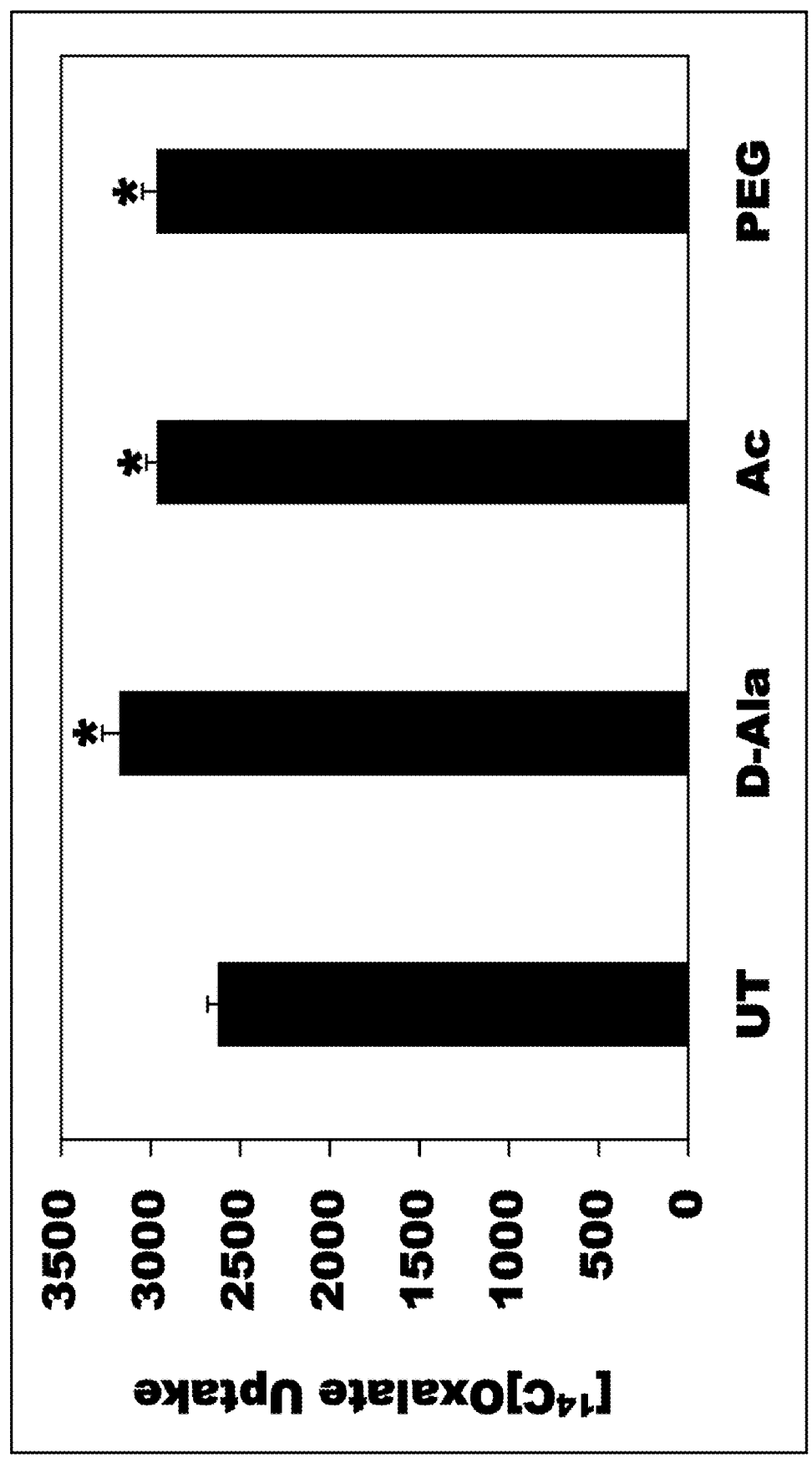
FIG. 13. P9 with N-terminal acetylation (Ac), C-terminal amidation (Am), and G16 replaced with D-alanine (D-Ala) significantly stimulate oxalate transport by a human sigmoid colon organoid.

301 (54 kDa) and 318 (52 kDa) Sel1 proteins have several SLR motifs (30-35 amino acids [aa] in length; called here peptides 1-6 [P1-6 for 301] and 7-11 [P7-11 for 318]; FIG. 8); it is contemplated that one or more of these domains mediate the observed stimulation, given their importance in protein-protein interactions and signal transduction pathways. To test this hypothesis, P1-6 and P7-11 peptides from the human Of strain OXCC13 were chemically synthetized by Genscript (NJ, USA). P4 (1.5-fold) and P4-6 (1.8-fold) significantly stimulated oxalate transport by C2 cells (FIG. 1), while P1-3, 5 & 6 had no effects. Individually, P7-10 significantly stimulated (~1.5-fold) oxalate transport by C2 cells (FIG. 2). The combination of P8+9 stimulated oxalate transport >2.4-fold by C2 cells, similar to the CM (FIG. 3), in a dose-dependent manner (FIG. 4) and more than any other combination. Of interest is that 318 (P7-11) is the only Sel1 protein identified when the Mass-Spec data was analyzed against OXCC13 genome when a highly stringent search was used. 318 gene is near 7 other Sel1 genes (319-323, located together in a potential operon, and 310/317), collectively making 318 a key Sel1 protein for Of. P8+9-induced stimulation is better than the 318-induced stimulation potentially due to the batch to batch variability observed with recombinant 318 generated in *E. coli*. In addition to SLR motifs, 318 is also predicted to have 2 TPR (tetratricopeptide repeat; 34 aa) motifs, and studies are in progress to evaluate their effects on oxalate transport given their important roles in protein-protein interactions and signaling pathways. Having identified these small peptides, the potential for therapeutic development increases since from a drug development prospective it is highly desirable to work with small peptides rather than large proteins.

Figure 3:
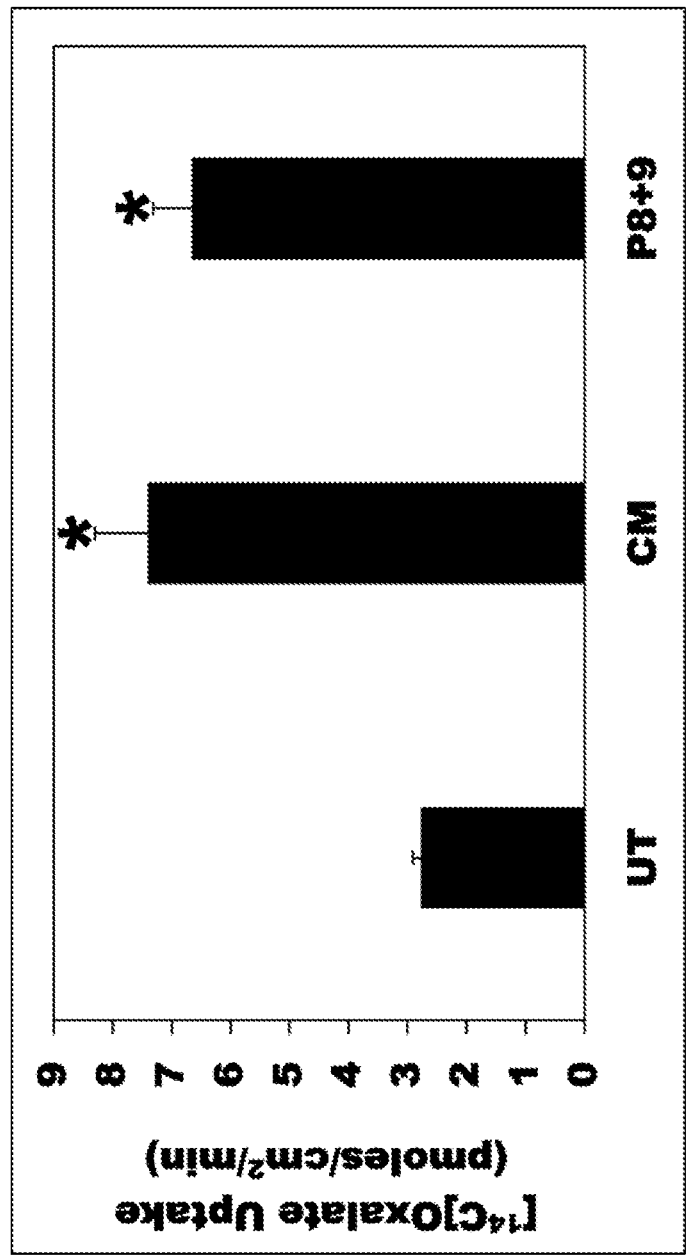
FIG. 3. P8+9 peptides significantly stimulate (>2.4-fold) oxalate transport by C2 cells and similar to the conditioned medium (CM).
Figure 4:
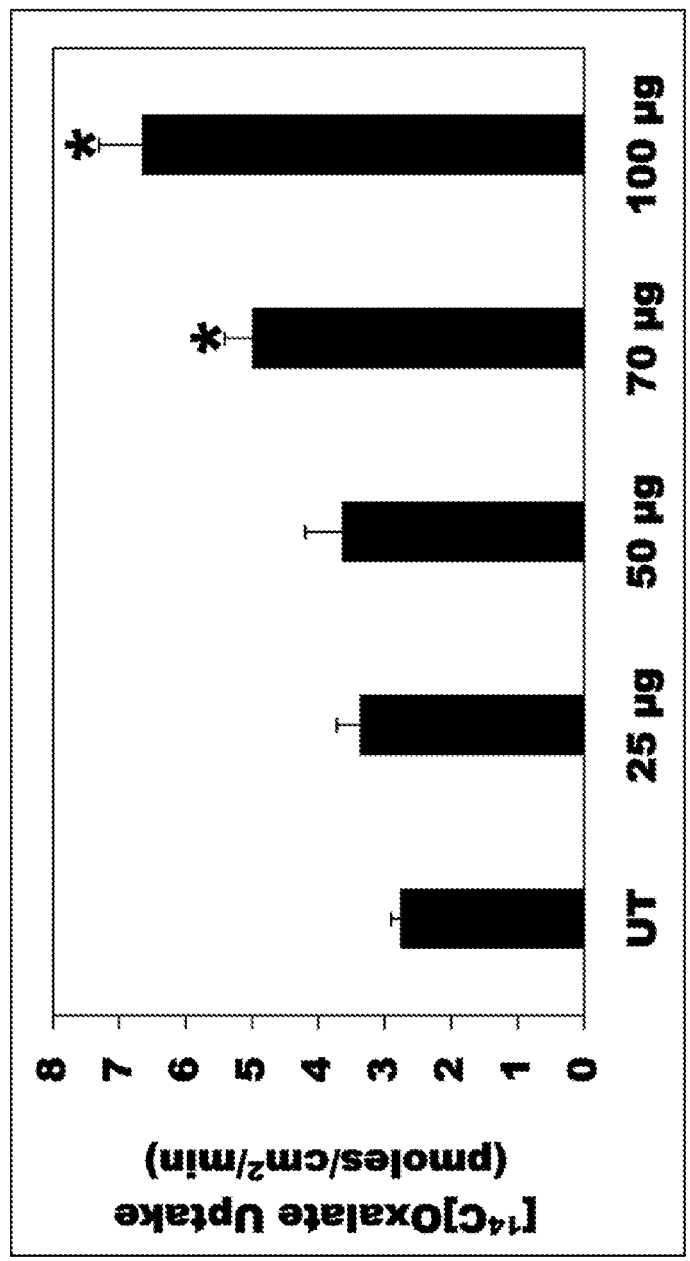
FIG. 4. P8+9 peptides significantly stimulate oxalate transport by C2 cells in a dose-dependent manner.

Two of the most potent stimulators of oxalate influx were tested together, and it was demonstrated that P8+9 peptides significantly stimulate (>2.4-fold) oxalate transport by C2 cells to a level about similar to the *Oxalobacter*-derived culture conditioned medium (CM: >2.6-fold) (FIG. 3). The P8+9 peptides significantly stimulate oxalate transport by C2 cells in a dose-dependent manner, indicating a receptor-ligand-type interaction (FIG. 4). Several other P7-P11 peptide combinations (including all of them together) stimulate oxalate transport by C2 cells to a level less than observed with P8+9 in preliminary studies.

Although the transformed C2 cells resemble the native epithelium, they don't fully recapitulate the in vivo physiological responses. Primary stem-cell derived intestinal organoids (Orgs) were recently established as an ex vivo model of the intestinal epithelium, and they mimic the full spectrum of physiological responses in vivo. Therefore, experiments were conducted during development of embodiments herein to confirm the C2 findings in colonic organoids. P7-10 peptides significantly stimulate (1.8-fold) oxalate transport by human sigmoid colon organoid and human ileum organoid (FIG. 6); thereby confirming the results determined in C2 cells. Additionally, experiments conducted during development of embodiments herein demonstrate that P8+9 peptides significantly stimulated oxalate transport by an ileum (FIG. 5A; ~2-fold), sigmoid colon (FIG. 5B; ~1.8-fold), and distal colon (~1.7-fold; not shown) organoids.

The intestine plays a major role in oxalate homeostasis, responsible for dietary oxalate absorption and gastrointestinal oxalate secretion/excretion. Animals and humans studies show that Of metabolizes dietary oxalate leading to reduced intestinal absorption and urinary oxalate excretion (Refs. 8, 30; incorporated by reference in their entireties). Of is an anaerobic colonic bacterium which utilizes oxalate as its exclusive energy source (Ref. 17; incorporated by reference in its entirety). In addition to degrading dietary oxalate, Of, for its own potential survival benefit, also interacts with the colonic epithelium to induce colonic oxalate secretion via a secretagogue, leading to reduced urinary oxalate excretion (Ref. 15; incorporated by reference in its entirety). Of colonization of a mouse model for PH type I was associated with 50% reduction in serum and urinary oxalate levels due to induction of colonic oxalate secretion (Ref. 18; incorporated by reference in its entirety). However, PH1 mice lost colonization within 18 days when switched from a high oxalate/low calcium diet (1.5% oxalate/0.5% calcium) to regular mouse chow (0.25% oxalate/1% calcium) (Ref. 18; incorporated by reference in its entirety). In addition, sustaining Of colonization in rats required a 3% dietary oxalate and colonized rats lost Of colonization within 5 days of dietary oxalate removal. Of colonized rats on high oxalate diets demonstrated greater urinary oxalate levels than that of non-colonized rats on a low oxalate diet and colonization was not maintained without reducing dietary calcium intake. Furthermore, studies in PH patients & PH1 mice raise the possibility that the intraluminal environment in PH is not supportive of sustained Of colonization (Refs. 18-19; incorporated by reference in their entireties). These limitations have resulted in the failure of several phase I-III trials using Of to lower urine or plasma oxalate levels in PH patients. Therefore, an appropriate strategy is to use Of-derived factors that can be directly administered to stimulate intestinal oxalate secretion to lower urine and plasma oxalate levels.

Toward this end, Of culture conditioned medium (CM) was prepared as recently reported (Ref. 4; herein incorporated by reference in its entirety) and human intestinal Caco2-BBE (C2) cells were used to evaluate the effects of Of CM on intestinal oxalate transport. Apical oxalate uptake by C2 cells was measured by imposing an outward Cl gradient by removing extracellular Cl [Cli>Clo] (Refs. 3, 4, 14; incorporated by reference in their entireties) and measuring DIDS (anion exchange inhibitor)-sensitive influx of 14C-oxalate in exchange for intracellular Cl [i.e. apical Cl-oxalate exchange activity, ≥49% of which is mediated by the oxalate transporter SLC26A6 (A6) in C2 cells (4, 12))]. A6 is the critical transport mechanism for exchanging intracellular oxalate for mucosal Cl during the process of transepithelial intestinal oxalate secretion, but its activity was measured by the more convenient assay of cellular oxalate uptake since it can transport oxalate in either direction (Ref. 22; incorporated by reference in its entirety) Of note is that A6 null mice have a critical defect in intestinal oxalate secretion resulting in enhanced net absorption of dietary oxalate, hyperoxalemia, hyperoxaluria, and a high incidence of COKS (Refs. 13, 21; incorporated by reference in their entireties).

Of-derived factors, such as the peptides described herein, stimulate oxalate transport in vitro: Preincubation of C2 cells with Of CM (1:50 dilution×24 h) stimulated oxalate transport >2.8-fold compared to untreated cells (UT) or cells treated with Of growth medium without bacteria included (OM) (UT=3.1±0.2; OM=2.9±0.3; CM=9.1±0.9 pmoles/cm2/min) (Ref. 4: herein incorporated by reference in its entirety). CM from *Lactobacillus acidophilus* did not impact oxalate transport, indicating specificity (Ref. 4: herein incorporated by reference in its entirety. Pretreatment of the CM with heat, pepsin, or trypsin completely abolished its stimulatory effects, indicating that the secreted factor(s) is/are likely to be proteins and/or peptides (Ref. 4: herein incorporated by reference in its entirety). Selective ultrafiltration revealed that the secreted factors have molecular weights mostly between 10-30 kDa (Ref. 4: herein incorporated by reference in its entirety). Pretreatment with the PKA inhibitor H89 completely blocked CM-induced oxalate transport, indicating that it is mediated by PKA activation (4). CM-induced stimulation is DIDS-sensitive and knockdown studies showed that stimulation is largely mediated by A6 (Ref. 4: herein incorporated by reference in its entirety), as well as A2. Lowering oxalate concentration in the culture medium from 5 g/L to 1 g/L led to a CM with >2-fold higher stimulatory effect (Ref. 4: herein incorporated by reference in its entirety), while increasing oxalate to 25 g/L led to a CM with 50% reduced activity, indicating that the secretion of these factors is inducible. CM-induced transport is due to >2-fold increase in Vmax (i.e. enhanced transport capacity) and >3.4-fold reduction in Km [i.e. increased affinity for oxalate] of the involved transporter(s) (Ref. 4: herein incorporated by reference in its entirety). CM did not affect A6 surface protein expression (Ref. 4: herein incorporated by reference in its entirety), and given the reduced Km (greater A6 affinity for oxalate), the observed stimulation is due to CM-induced increase in the intrinsic activity of the preexisting A6 membrane transporters.

Figure 5:
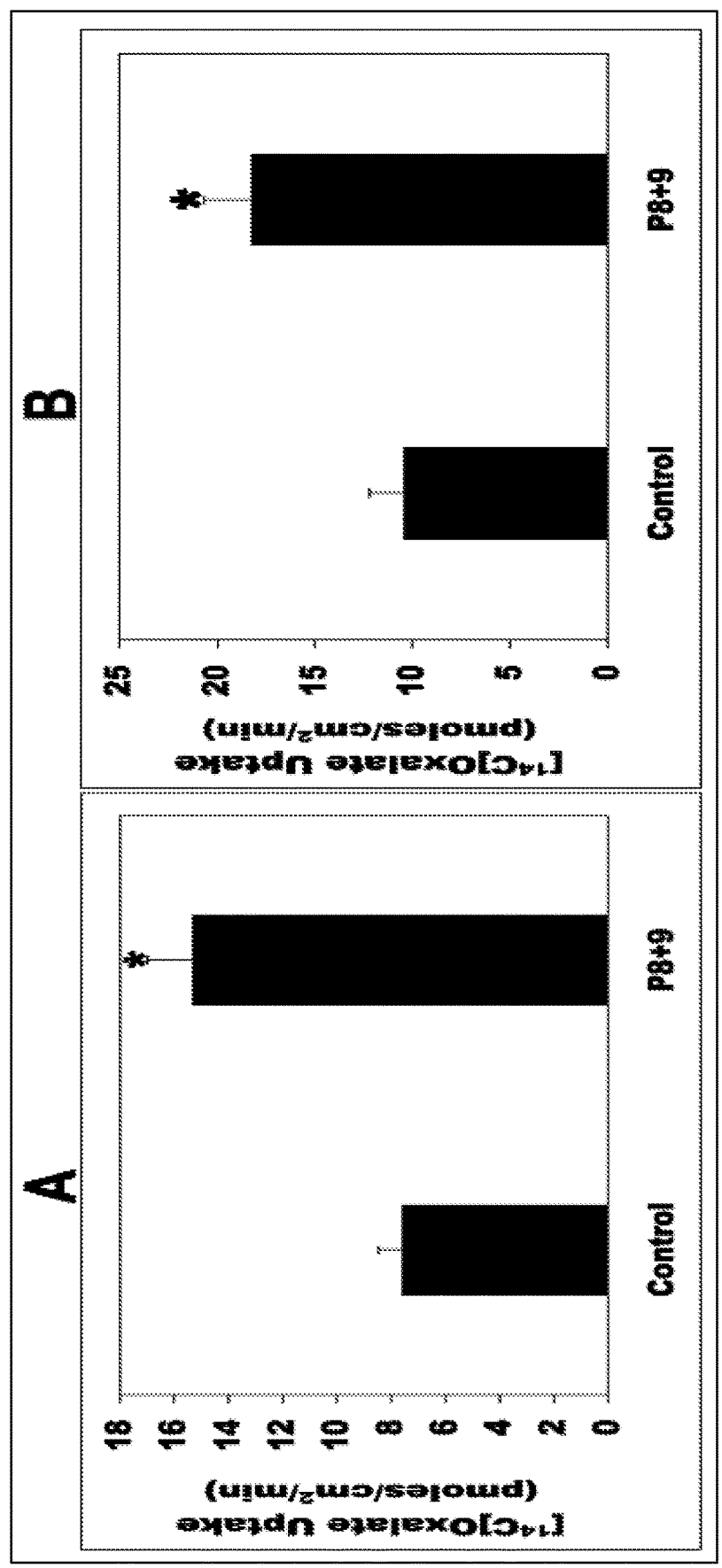
FIG. 5. P8+9 peptides significantly stimulated oxalate transport by an ileum (A) and sigmoid (B) Organoids.
Figure 6:
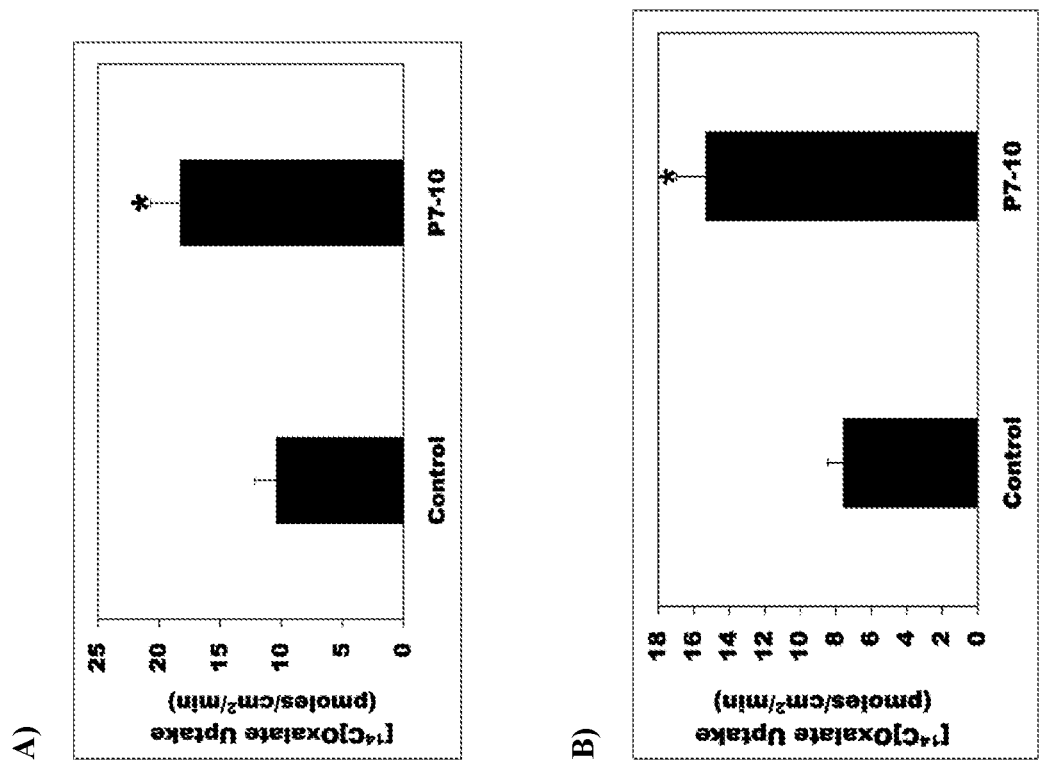
FIG. 6. P7-10 peptides significantly stimulated oxalate transport by an ileum (A) and sigmoid (B) Organoids.

To recapitulate the findings in vivo, primary stem-cell derived intestinal organoids (Org) were used which have been established as an ex vivo model of the intestinal epithelium with a full spectrum of physiological responses found in vivo (Ref. 35; incorporated by reference in its entirety). A human sigmoid colonic Org (from a healthy individual) was grown and maintained as previously reported (Ref. 34; incorporated by reference in its entirety). Org cells were plated onto collagen-coated transwell filters and formed monolayers. Monolayer confluency and differentiation was confirmed by transepithelial electrical resistance measurements (Ref. 34; incorporated by reference in its entirety). Org cells demonstrated transport of oxalate measured as influx of $^{14}$C-oxalate in exchange for intracellular Cl. The influx of $^{14}$C-oxalate is DIDS-sensitive (inhibited by ~70% with 100 μM DIDS), indicating that it is anion exchange mediated oxalate transport. An ileum Org was developed which demonstrates DIDS-sensitive (inhibited by ~80% with 500 μM DIDS) oxalate transport. Importantly, P8+9 (100 μg/ml×24 h) significantly stimulated oxalate transport by the ileum Org (2-fold; FIG. 5A) and the sigmoid Org (1.8-fold; FIG. 5B). These results show that P8+9 stimulates oxalate transport by human Org as observed in C2 cells, suggesting that these peptides are very likely to work in humans in vivo.

Peptides Modifications to Enhance their In Vivo Stabilities

Given P4-10 peptides susceptibilities to proteolytic degradation, the lead peptides are optimized to improve peptide druggability through structural modification approaches that reduce proteolysis and thus enhance stability. Proteolytic enzymes like aminopeptidases and carboxypeptidases break down peptide sequences from the N- and C-termini, and therefore N-(acetylation) and/or C-(amidation) terminal modifications can improve peptide stability (Ref. 36; herein incorporated by reference in its entirety). Of note is that the N-terminal acetylated forms of GLP1 7-34 and somatostatin analogs were shown to be much more stable than the native peptides (Ref. 36; herein incorporated by reference in its entirety). In addition, substitution of natural L-amino acids with non-natural D-amino is known to reduce the substrate recognition and binding affinity of proteolytic enzymes and enhances peptide stability (Ref. 36; herein incorporated by reference in its entirety). An example is the drug-octreotide, in which replacing L-amino acids with D-amino acids prolonged the human in vivo half-life from a few minutes to 1.5 h (Ref. 36; herein incorporated by reference in its entirety). Moreover, cyclization (head-to-tail, head/tail-to-side-chain, and/or side-chain-to-side-chain) enhances peptide stability and permeability by introducing conformation constraint, thereby reducing peptide flexibility, and a cyclic enkephalin analog is highly resistant to enzymatic degradation (Ref. 36; herein incorporated by reference in its entirety). Furthermore, modification of natural amino acids improves peptide stability by introducing steric hindrance or disrupting enzyme recognition. An example is buserelin, in which one Gly is replaced with a t-butyl-D-Ser and another Gly is replaced with ethylamide, leading to prolonged half-life in humans compared to a very short half-life (minutes) in the unmodified GRH (Ref. 36; herein incorporated by reference in its entirety). P4-11 peptides are subjected to all of the above described modifications. The Gly residues in each peptide are substituted with PEG6, which is much better than PEG4 for peptide stabilization. In addition, both N-acetylation and C-amidation in the same peptide as well as applying N-acetylation or C-amidation in conjunction with amino acid substitution are made. Moreover, peptides that are cationic show fast degradation due to their arginine (R) and lysine (K) contents and therefore, the R residues in the peptides of this invention are replaced with the arginine homologue Agp to enhance their stabilities (Ref. 36; herein incorporated by reference in its entirety). Replacing all R with Agp in peptide Sub3 led to a dramatic increase in its stability (Ref. 37; herein incorporated by reference in its entirety).

Identification of P8 and P9 Functional Subdomains

Figure 7:
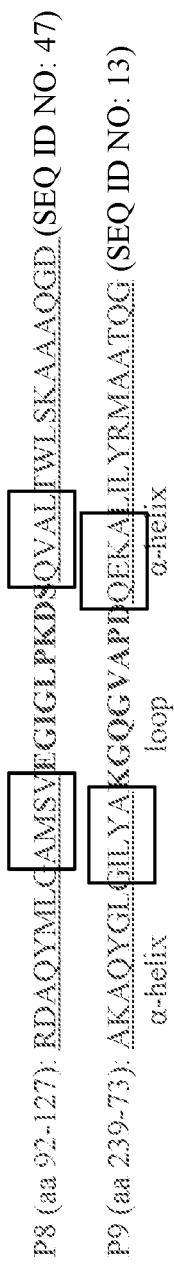
FIG. 7. P8 and P9 peptides sequences.

The 318 homology-based structure has a long helical structure composed of many alpha helix hairpins. 318 is predicted to have 5 SLR motifs (P7-11; FIG. 8), and each SLR motif is composed of 2 alpha helices (underlined aa for P8 and P9; FIG. 7), separated by a loop (bolded aa; FIG. 7). G14 & 16 in the loop are conserved in all P1-11 peptides and they are likely important for the structure. Y96, A122, Q125, and G126 in P8 and Y243, A269, Q272, and G273 in P9 are close to each other and potentially form the binding sites. Similar sequences are also found in P4 (from 301), P7, and P10. Of remarkable interest is that only P4 and P7-10 individually stimulated oxalate transport (~1.5-fold) by C2 cells. P1-3, 5, 6, and 11 don't have similar sequences, especially Y, and they don't stimulate oxalate transport by C2 cells. Conserved P8 & P9 aa are the same in the two sequences (FIG. 7). Detailed analysis of the P8 and 9 structures indicates that the only regions that can be potentially deleted without affecting their functions will be the 4 aa (boxed) from each helix. Deleting >4 aa would likely disrupt the helix function. Therefore, AMSV (SEQ ID NO: 48)/QVAL (SEQ ID NO: 49) and ILYA (SEQ ID NO: 50)/QEKA (SEQ ID NO: 51) will be deleted from P8 and P9, respectively, to identify the smallest P8 and P9 subdomains that stimulate oxalate transport similar to the full-length peptides. The truncated peptides (truncated P8: RDAQYMLGEGIGLPKDSTWLSKAAAQGD; truncated P9: AKAQYGLGKGQGVAPDLILYRMAATQG) will be chemically synthesized by Genscript, 1-4 mg which is sufficient for the studies, and >95% purity. If the truncated P8 and truncated P9 similarly stimulate oxalate transport by C2 cells as the full-length peptides, this will confirm successful shortening of each peptide by 8 aa. Additional modifications include deleting the first and last aa in each loop (E/S in P8 and K/D in P9) and the effects of the truncated P8 and truncated 9 will be similarly assessed. If the truncated P8 and truncated P9 similarly stimulate oxalate transport by C2 cells as the full-length peptides, this will confirm successful shortening of each peptide by 10 aa. Additional modifications include deleting the first and last aa in each loop (E/S in P8 and K/D in P9) and the effects of the truncated P8 and 9 will be similarly assessed. If the truncated P8 and P9 similarly stimulate oxalate transport by C2 cells as the full-length peptides, this will confirm successful shortening of each peptide by 10 aa.

The SLR consensus sequence highlights conserved alanine (A) and glycine (G) residues at positions 3, 8, 14, 24, 32, 39, 40 and 43. The G residues at positions 14, 24, and 43 facilitate sharp turns in the loop regions and small residues at positions 3, 8, 32, 39, and 40 allow tight packing of α-helices. Both P8 and P9 have A at positions 3, 24, & 32 (A94/241, A115/262, and A123/270, respectively) and G at positions 8 & 14 (G99/246 and G105/252). In addition, Y96, A122, Q125, and G126 in P8 and Y243, A269, Q272, and G273 in P9 form the potential binding sites. It is contemplated that one or more of these conserved aa (individually or in combination), especially those form the potential binding site, is/are crucial for the observed stimulation by facilitating the binding to a receptor and/or other interacting proteins. To define the critical aa in the identified subdomains, the above described conserved aa is substituted as follows. Y96/243 will be substituted with phenylalanine (F), while the specified A, Q, & G will be substituted with tyrosine (Y). The individual substitutions are Y96/243, A122/269, Q125/272, G126/G273, A94/241, A115/262, A123/270G8, G99/246, and G105/252 or combinations thereof. Further deletion combinations include 3 aa (AMS/QVA or MSV/VAL and ILY/QEK or LYA/EKA), 2 aa (AM/QV, MS/VA, or SV/AL and IL/QE, LY/EK, or YA/KA), or single aa deletions (e.g. A/Q or V/L). Complete abolishment or reduction of subdomain-mediated stimulation of oxalate transport by C2 cells denote critical residues needed to activity.

P8+9 are designed to have N-terminal or C-terminal biotin tags used to pull down complexes. Biotinylated P4-6 peptides with N-terminal biotin tags stimulated oxalate transport by C2 cells similar to the untagged P4-6 peptides, indicating that the biotin tags are unlikely to affect P8+9 activities.

In vivo efficacy testing of peptides.

Having effectively optimized the characterized P8+9 subdomains, the optimized subdomains are tested to determine whether the peptides retain their biological activities in vivo and significantly reduce urine and plasma oxalate levels in hyperoxaluric and hyperoxalemic mice. The CM significantly reduced (>32.5%) urinary oxalate excretion in PH1 mice (Ref. 4; herein incorporated by reference in its entirety), and therefore these mice are used to evaluate the therapeutic potential of the optimized peptides and peptides subdomains. PH1 mice using one sex (males; 3 doses; n=5/dose; Control mice receive a vehicle) receive optimized subdomains SD8 and SD9 in pilot dose ranging (3 different doses for each of SD8, SD9, and SD8+9 for up to 4 weeks). The doses found to work well (leading to the highest reduction in urine and plasma oxalate levels) are further tested in both sexes. To this end, PH1 mice (12-20 weeks old; n=14/sex/treatment group) are placed individually in metabolic cages and urine & feces are collected on days 0, 7, 14, 21, & 28. Blood samples are collected on days 0, 14, and 28. Following baseline urine, blood, and fecal samples collection, the mice receive SD8+9 (if found to give the highest reduction in urine and plasma oxalate levels in the pilot studies described above) rectally as enemas (100 μl twice daily×28 days) using the optimal doses developed in the pilot studies. Control mice receive vehicle (the buffer in which the subdomains are dissolved). The urine and blood samples are acidified with 4N HCL and stored at −80° C. Urine, plasma, and fecal oxalate levels are measured enzymatically using oxalate oxidase, employing sodium nitrite (Ref. 32; herein incorporated by reference in its entirety) to prevent interference by ascorbic acid.

Observing normalization or significantly reduced urine and plasma oxalate levels in SD8+9-treated PH1 mice compared with vehicle-treated ones reflect in vivo retention of SD8+9 biological activities and the significant therapeutic potential of these peptides. As a result of enhanced colonic oxalate secretion, fecal oxalate levels are higher in the SD8+9-treated mice. In addition to reducing urinary oxalate excretion in PH and without being bound by theory, SD8+9 effectively lowers urinary oxalate excretion in EH, which is seen in association with many conditions, including IBD, obesity, and post-bariatric surgery. This is very important since showing that SD8+9 can significantly reduce urine oxalate levels in both PH and EH prove that SD8+9 are effective in all forms of hyperoxalurias and thus have a wider clinical applicability. To this end, SD8+9 is administered rectally to SAPM1/YitFc (SAM) and ob/ob (ob) mice (8-12 weeks old; n=14/sex/treatment group). SAM is a mouse model with remarkable similarities to human Crohn's disease that the inventors developed as a good model for the IBD-associated hyperoxaluria. SAM mice have 2-fold hyperoxaluria compared to controls, as well as significantly reduced A6 ileal mRNA (>87%) and total protein (>60%) levels. ob is an obesity model developed as a good model for the obesity-associated hyperoxaluria (>3.2-fold hyperoxaluria compared to controls) (Ref. 32; incorporated by reference in its entirety). Of note is that the doses found to work in PH1 mice are expected to work in SAM mice (similar body weights), but unlikely to work in the obese ob mice (having at least twice the body weights of PH1 mice). Therefore, a dose ranging study will be done in ob mice. SAM and ob mice are similarly treated with SD8+9 and the data are analyzed as described above with the PH1 mice.

Having shown that SD8+9 significantly reduce plasma and urine oxalate levels in PH1 as well as urine oxalate levels in the ob and SAM mice, experiments are conducted to demonstrate that the observed reduction in urine and plasma oxalate levels is due to SD8+9-induced enhanced colonic oxalate secretion. Toward this end, cecal, proximal, and distal colonic tissues from SD8+9- and vehicle-treated PH1, ob, and SAM mice are isolated and mounted in Ussing chambers at the end of treatment. Two unidirectional [mucosa to serosa=JMS (absorptive flux), and serosa to mucosa=JSM (secretory flux)] are assessed and the magnitude and direction of the net flux (Jnet) across conductance-matched tissues are determined by calculating the difference between the two measured unidirectional fluxes as previously reported (Ref. 4; herein incorporated by reference in its entirety). Compared to vehicle-treated mice, if net basal cecal oxalate flux is converted from absorption to secretion, or significantly higher net basal secretory flux is observed in the proximal and/or the distal colon of SD8+9-treated mice [due to significantly increased secretory flux and/or reduced absorptive flux(es)], then such findings strongly support the idea that SD8+9 reduce serum and urine oxalate levels in PH1 mice and urine oxalate levels in ob and SAM mice by enhancing colonic oxalate secretion. Collectively, such findings provide a molecular basis for therapeutic application of SD8+9 for prevention and/or treatment of hyperoxaluria, hyperoxalemia, and related COKS.

Experiments were conducted during development of embodiments herein to determine the effects of various peptide modifications (Table 11) including N-terminal acetylation, C-terminal amidation, replacing glycines with PEG, and replacing L-amino acids with D-amino acids on stimulation of oxalate transport. Results are depicted in FIG. 9-13.

The results in FIGS. 9-13 show that P8 and P9 peptides with N-terminal acetylation and C-terminal amidation significantly stimulated oxalate transport by C2 cells to a level similar to native P8 and P9 peptides. In addition, P8 and P9 peptides with all Glycines replaced with PEG6 also similarly stimulated oxalate transport by C2 cells compared with native P8 and P9 peptides. Moreover, replacing G15 in P8 and G16 in P9 with D-alanine also similarly stimulated oxalate transport by C2 cells compared with native P8 and P9 peptides. Collectively, these results indicate that all of the above described structural modifications did not impact the functional activities of P8 and P9 peptides. P8 and P9 peptides having all natural L-amino acids replaced by D-amino acids were nonfunctional.

TABLE 11

Modified 318 SLR domain peptides

| | | |
|---|---|---|
| P8-Ac | Ac-DAQYMLGAMSVEGIGLPKDSQVALTWLSKAAAQGD | SEQ ID NO: 39 |
| P8-Daa | DAQYMLGAMSVEGI(d-alanine)LPKDSQVALTWLSKAAAQGD | SEQ ID NO: 40 |
| P8-Am | DAQYMLGAMSVEGIGLPKDSQVALTWLSKAAAQGD-Am | SEQ ID NO: 41 |
| P8-Peg | DAQYMLA(Peg)MSVE(Peg)I(Peg)LPKDSQVALTWLSKAAAQ(Peg)D | SEQ ID NO: 42 |
| P9-Ac | Ac-AKAQYGLGILYAKGQGVAPDQEKALILYRMAATQG | SEQ ID NO: 43 |
| P9-Daa | AKAQYGLGILYAKGQ(d-alanine)VAPDQEKALILYRMAATQG | SEQ ID NO: 44 |
| P9-Am | AKAQYGLGILYAKGQGVAPDQEKALILYRMAATQG-Am | SEQ ID NO: 45 |
| P9-Peg | AKAQY(Peg)L(Peg)ILYAK(Peg)Q(Peg)VAPDQEKALILYRMAATQ(Peg) | SEQ ID NO: 46 |

Oxalate Transport Enhanced by Addition of Select Trace Elements

Figure 14:
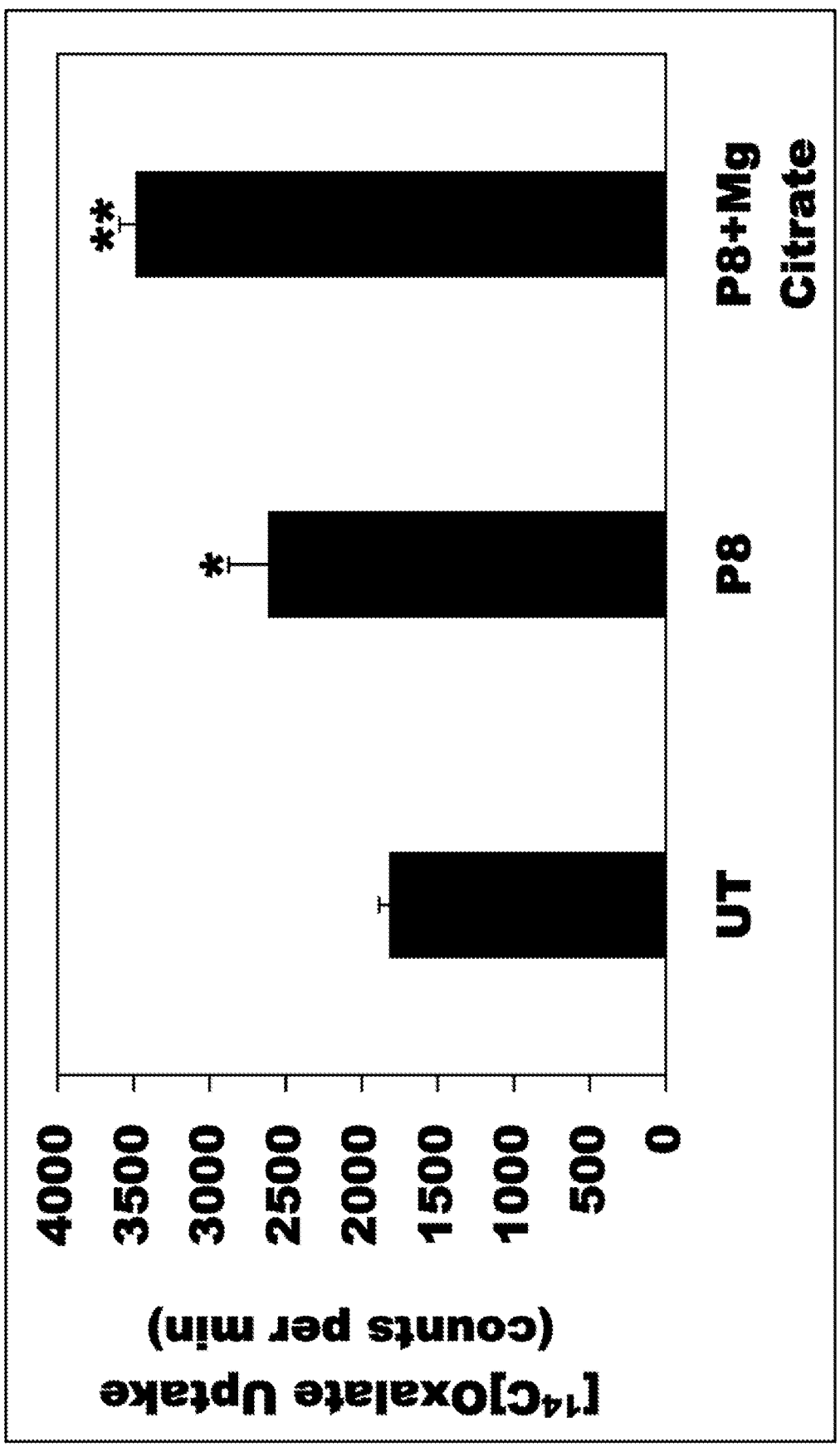
FIG. 14. P8 and magnesium citrate produced enhancement of oxalate uptake over P8 peptide alone.
Figure 15:
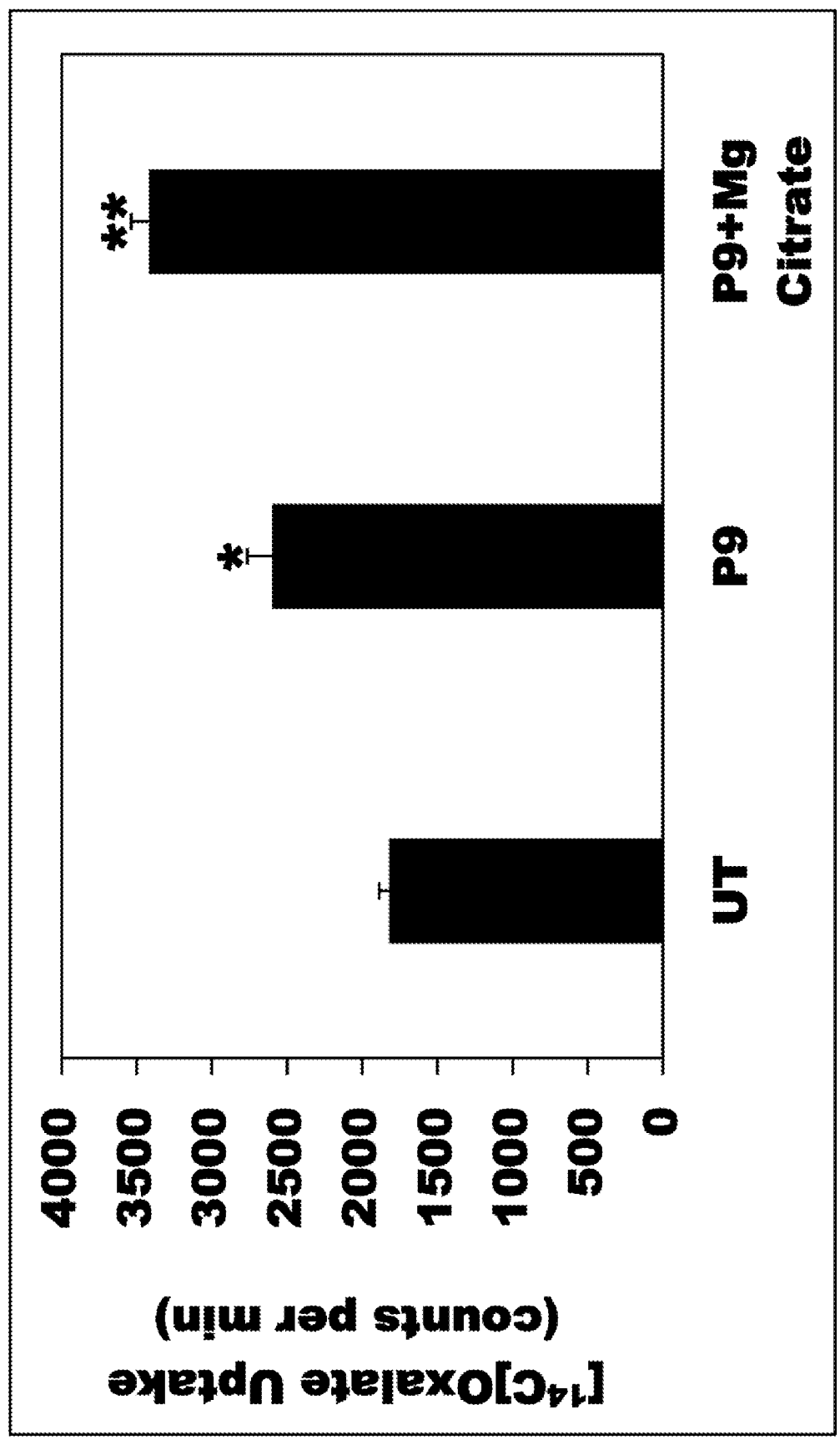
FIG. 15. P9 and magnesium citrate produced enhancement of oxalate uptake over P8 peptide alone.
Figure 16:
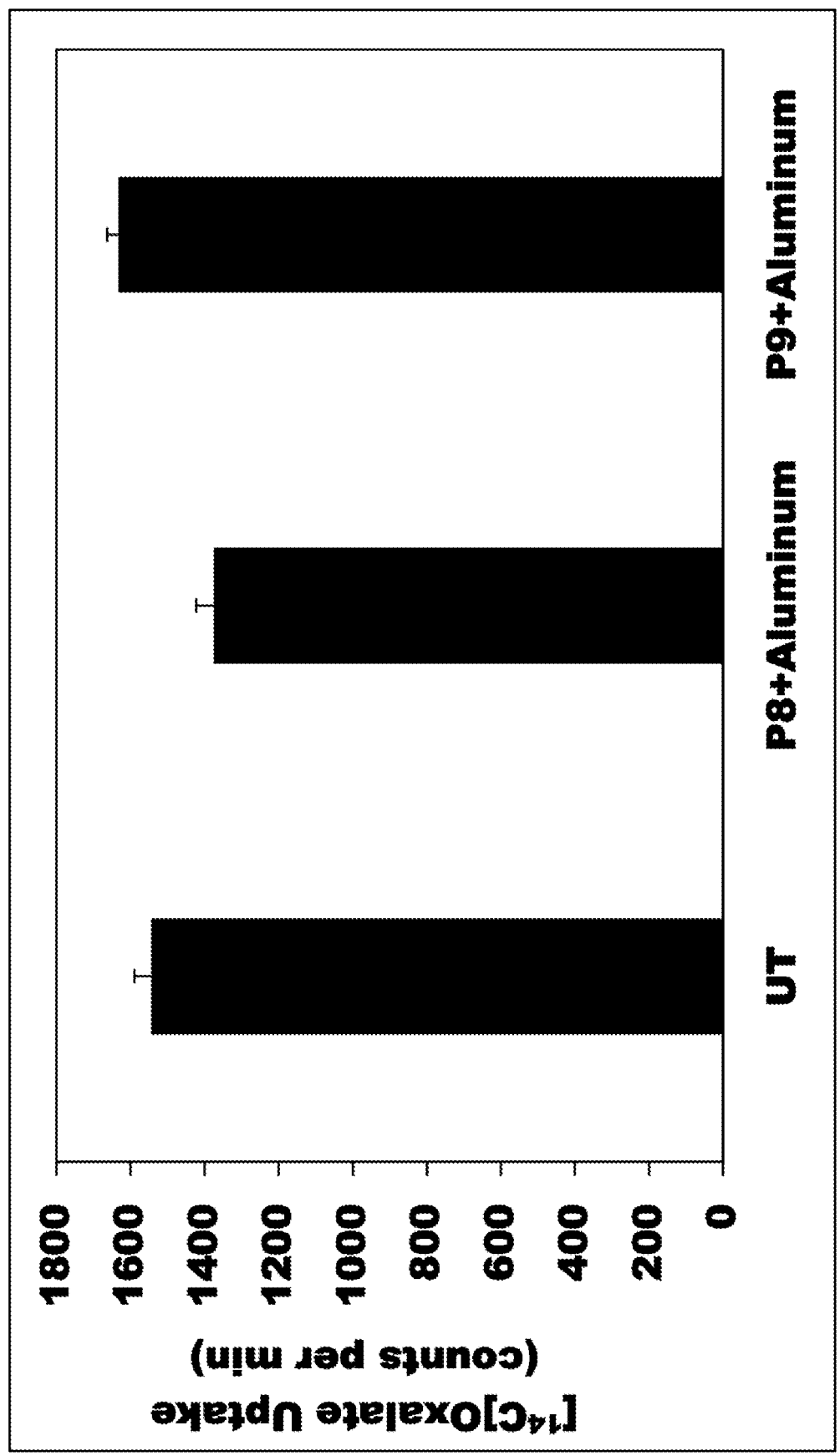
FIG. 16. The addition of aluminum to P8 or P9 did not result in increased oxalate transport and oxalate transport induction was similar to untreated

The inventors sought to identify trace elements to better stimulate oxalate transport by facilitating the binding of P8 and/or P9 to a cell surface receptor. The inventors analyzed combinations of P8 and P9 alone or with aluminum, zinc, or magnesium by measuring C14 oxalate transport in C2 cells. Peptides P8 and P9 were premixed with magnesium citrate prior to administration to human Caco2-BBE cells. The addition of magnesium citrate induced a 1.9-fold increase in oxalate transport (FIGS. 14 and 15) compared to peptide alone. Zinc citrate was observed to have similar stimulatory effects but not from zinc chloride or zinc sulfate. The addition of aluminum to P8 or P9 did not result in increased oxalate transport and oxalate transport induction was similar to untreated (FIG. 16).

REFERENCES

The following references are herein incorporated by reference in their entireties.

1. Alexander R T, Hemmelgarn B R, Wiebe N, Bello A, Morgan C, Samuel S, Klarenbach S W, Curhan G C, Tonelli M, and for the Alberta Kidney Disease N. Kidney stones and kidney function loss: a cohort study. *Bmj* 345: e5287, 2012.
2. Allison M J, Dawson K A, Mayberry W R, and Foss J G. *Oxalobacter formigenes* gen. nov., sp. nov.: oxalate-degrading anaerobes that inhabit the gastrointestinal tract. *Archives of Microbiology* 141: 1-7, 1985.
3. Amin R, Sharma S, Ratakonda S, and Hassan H A. Extracellular Nucleotides Inhibit Oxalate Transport by Human Intestinal Caco2-BBE Cells Through PKC-delta Activation. *American Journal of Physiology Cell Physiology*, 2013.
4. Arvans, D., Jung, Y., Antonopoulos, D., Koval, J., Granja, I., Bashir, M., Karrar, E., Roy-Chowdhury, J., Musch, M., Asplin, J., Chang, E., and Hassan, H. A. *Oxalobacter formigenes*-derived Bioactive Factors Stimulate Oxalate Transport by Intestinal Epithelial Cells. 2017. Journal of the American Society of Nephrology (JASN). 28: 876-887.
5. Borthakur A, Gill R K, Tyagi S, Koutsouris A, Alrefai W A, Hecht G A, Ramaswamy K, and Dudeja P K. The probiotic *Lactobacillus acidophilus* stimulates chloride/hydroxyl exchange activity in human intestinal epithelial cells. *The Journal of Nutrition* 138: 1355-1359, 2008.
6. Caudarella R, Rizzoli E, Pironi L, Malavolta N, Martelli G, Poggioli G, Gozzetti G, and Miglioli M. Renal stone formation in patients with inflammatory bowel disease. *Scanning Microscopy* 7: 371-379; discussion 379-380, 1993.
7. Coe F L, Evan A, and Worcester E. Kidney stone disease. *The Journal of Clinical Investigation* 115: 2598-2608, 2005.
8. Daniel S L, Hartman P A, and Allison M J. Microbial degradation of oxalate in the gastrointestinal tracts of rats. *Appl Environ Microbiol* 53: 1793-1797, 1987.
9. Danpure C J and Jennings P R. Peroxisomal alanine: glyoxylate aminotransferase deficiency in primary hyperoxaluria type I. *FEBS letters* 201: 20-24, 1986.
10. Dawson P A, Russell C S, Lee S, McLeay S C, van Dongen J M, Cowley D M, Clarke L A, and Markovich D. Urolithiasis and hepatotoxicity are linked to the anion transporter Sat1 in mice. *The Journal of Clinical Investigation* 120: 706-712, 2010.
11. Eisner B H, Porten S P, Bechis S K, and Stoller M L. Diabetic kidney stone formers excrete more oxalate and have lower urine pH than nondiabetic stone formers. *The Journal of Urology* 183: 2244-2248, 2010.
12. Freel R W, Morozumi M, and Hatch M. Parsing apical oxalate exchange in Caco-2BBe1 monolayers: siRNA-knockdown of SLC26A6 reveals the role and properties of PAT-1. *American Journal of Physiology* 297: G918-929, 2009.
13. Freel R W, Hatch M, Green M, and Soleimani M. Ileal oxalate absorption and urinary oxalate excretion are enhanced in Slc26a6 null mice. American journal of physiology Gastrointestinal and liver physiology 290: G719-728, 2006.
14. Hassan H A, Cheng M, and Aronson P S. Cholinergic signaling inhibits oxalate transport by human intestinal T84 cells. *American Journal of Physiology Cell Physiology* 302: C46-58, 2012.
15. Hatch M, Cornelius J, Allison M, Sidhu H, Peck A, and Freel R W. *Oxalobacter* sp. reduces urinary oxalate excretion by promoting enteric oxalate secretion. *Kidney International* 69: 691-698, 2006.
16. Hatch M and Freel R W. A human strain of *Oxalobacter* (HC-1) promotes enteric oxalate secretion in the small intestine of mice and reduces urinary oxalate excretion. *Urolithiasis*, 2013.
17. Hatch M and Freel R W. Intestinal transport of an obdurate anion: oxalate. *Urological Research* 33: 1-16, 2005.
18. Hatch M, Gjymishka A, Salido E C, Allison M J, and Freel R W. Enteric oxalate elimination is induced and oxalate is normalized in a mouse model of primary hyperoxaluria following intestinal colonization with *Oxalobacter. American Journal of Physiology Gastrointestinal and LiverPphysiology* 300: G461-469, 2011.
19. Hoppe B, Beck B, Gatter N, von Unruh G, Tischer A, Hesse A, Laube N, Kaul P, and Sidhu H. *Oxalobacter formigenes*: a potential tool for the treatment of primary hyperoxaluria type 1. *Kidney International* 70: 1305-1311, 2006.
20. Hoppe B, von Unruh G, Laube N, Hesse A, and Sidhu H. Oxalate degrading bacteria: new treatment option for patients with primary and secondary hyperoxaluria? *Urological Research* 33: 372-375, 2005.
21. Jiang Z, Asplin J R, Evan A P, Rajendran V M, Velazquez H, Nottoli T P, Binder H J, and Aronson P S. Calcium oxalate urolithiasis in mice lacking anion transporter Slc26a6. *Nature Genetics* 38: 474-478, 2006.
22. Jiang Z, Grichtchenko, II, Boron W F, and Aronson P S. Specificity of anion exchange mediated by mouse Slc26a6. *The Journal of Biological Chemistry* 277: 33963-33967, 2002.
23. Langmead B, Trapnell C, Pop M, and Salzberg S L. Ultrafast and memory-efficient alignment of short DNA sequences to the human genome. *Genome Biology* 10: R25, 2009.
24. Love M I, Huber W, and Anders S. Moderated estimation of fold change and dispersion for RNA-seq data with DESeq2. *Genome Biology* 15: 550, 2014.
25. Mittl P R and Schneider-Brachert W. Sel1-like repeat proteins in signal transduction. *Cellular Signalling* 19: 20-31, 2007.
26. Nelson W K, Houghton S G, Milliner D S, Lieske J C, and San M G. Enteric hyperoxaluria, nephrolithiasis, and oxalate nephropathy: potentially serious and unappreciated complications of Roux-en-Y gastric bypass. *Surg Obes Relat Dis* 1: 481-485, 2005.

27. Pardi D S, Tremaine W J, Sandborn W J, and McCarthy J T. Renal and urologic complications of inflammatory bowel disease. *Am J Gastroenterol* 93: 504-514, 1998.
28. Robertson W G and Peacock M. The cause of idiopathic calcium stone disease: hypercalciuria or hyperoxaluria? *Nephron* 26: 105-110, 1980.
29. Salido E C, Li X M, Lu Y, Wang X, Santana A, Roy-Chowdhury N, Tones A, Shapiro U, and Roy-Chowdhury J. Alanine-glyoxylate aminotransferase-deficient mice, a model for primary hyperoxaluria that responds to adenoviral gene transfer. *Proceedings of the National Academy of Sciences of the United States of America* 103: 18249-18254, 2006.
30. Sidhu H, Schmidt M E, Cornelius J G, Thamilselvan S, Khan S R, Hesse A, and Peck A B.
Direct correlation between hyperoxaluria/oxalate stone disease and the absence of the gastrointestinal tract-dwelling bacterium *Oxalobacter formigenes*: possible prevention by gut recolonization or enzyme replacement therapy. *Journal of the American Society of Nephrology: JASN* 10 Suppl 14: S334-340, 1999.
31. Tao Y, Drabik K A, Waypa T S, Musch M W, Alverdy J C, Schneewind O, Chang E B, and Petrof E O. Soluble factors from *Lactobacillus* GG activate MAPKs and induce cytoprotective heat shock proteins in intestinal epithelial cells. *American Journal of Physiology* 290: C1018-1030, 2006.
32 Amin R, Asplin J, Jung D, Bashir M, Alshaikh A, Ratakonda S, Sharma S, Jeon S, Granja I, Matern D, and Hassan H. Reduced active transcellular intestinal oxalate secretion contributes to the pathogenesis of obesity-associated hyperoxaluria. Kidney international 93: 1098-1107, 2018.
33. Kasidas G P and Rose G A. Continuous-flow assay for urinary oxalate using immobilised oxalate oxidase. Annals of clinical biochemistry 22 (Pt 4): 412-419, 1985.
34. In J, Foulke-Abel J, Zachos N C, Hansen A M, Kaper J B, Bernstein H D, Halushka M, Blutt S, Estes M K, Donowitz M, and Kovbasnjuk O. Enterohemorrhagic *Escherichia coli* reduce mucus and intermicrovillar bridges in human stem cell-derived colonoids. Cellular and molecular gastroenterology and hepatology 2: 48-62 e43, 2016.
35. Zachos N C, Kovbasnjuk O, Foulke-Abel J, In J, Blutt S E, de Jonge H R, Estes M K, and Donowitz M. Human Enteroids/Colonoids and Intestinal Organoids Functionally Recapitulate Normal Intestinal Physiology and Pathophysiology. The Journal of biological chemistry 291: 3759-3766, 2016.
36. Di L. Strategic approaches to optimizing peptide ADME properties. The AAPS journal 17: 134-143, 2015.
37. Knappe D, Henklein P, Hoffmann R, and Hilpert K. Easy strategy to protect antimicrobial peptides from fast degradation in serum. Antimicrobial agents and chemotherapy 54: 4003-4005, 2010.

SEQUENCES

Sel1 301

(SEQ ID NO: 1)
atgtcgtccgtcattgctgattcgcagcagcctgcagtttcagaagaaaa cgcaaataaaattatccttgatgaggaaaaggcggtcatccaatgtaacg aaagatataagacggaaaatgatgaaaagggcgatgaagaaaccgtttca tggtgccgaaaagccgcgaagtctggtaatgcggaggcacaatatcttt tggcatgctggtttatgatggcagaggcgtgcagcaggataattgtgttg ccatgttatggtggatgaaagcagcagagcagaatcatgccaaggcactc gttatgctgggaaatcttcatcgtaaaggtcagtgcattgctgagaatta tccgaaagccattgcctattggaagagagctgctgttcagaataacgtat gggcatatcataatttagggacagcttattacgatggtatcggtgtggat aaaaatcctcatgaagctgttcgctggtggaagaaggcagccgaattggg ttttcctgaatctcagaacaatctgggtgctttatacaatgatgggaatg gtgttgatcgtgattatcaggaggctgttttctggtacagaaaaagtgcc ctgcagggcgacgaattgggacagtacaatcttgggggcttattattac ggcagagggataaaaaaagatttttctgaagcagtgtcgtggtacaaaaa atcagcagaacaagactatgcacaagcacagcataatcttggtgttacgt attacgaaggtgagggaataaaaaaagattacgccaaggctgtgtactgg tggaaaaaggcagcagaacaggggattccccaatctcagtataaccttgg cattgcatatgaagaaggctgggcgctgaaaaaaatccggagaatgctg ttttttggtacagaaaagcggctgaacagggacatgctgatgctcaaaac agacttggcatcgcttacaggtatggaaccggagtcaggaaaaatcccgc attgtctgtcaaatggctggaaaaagcggcaaagcagggcttgcaagag cacagttcaatttggggaaaaccttctatatcggagcaggcattaacaag aatacagacaaagcggtttactggttcataaaagctgccaatcagggttt cacagaagcacaggcttatattggtatgatttattttaaaggtaaatatg tcgccaagaacgaaaaaaaaggttttactggttaaaaaaagcagcagaa aaagacagtgctaaagcacaagcatttcttggcgctttatacattgcagg aaatgaagtgaagccaaatataaaggaaggcgttgccttgacaaaaaaag cggcattacagggtaattacgaggcacaaaccctgctcggttttttgctac gagaatggcttggaagtaaaaaaagacctgattgccgcatatgcgcttta cttgtcggcgtcacctcatttcgattttgcagaaaaggcgcgtcttgatc ttgaacggaaattaagcgaacaggaaatagcaaaggcaatatccgttaat acagcaaaattgtttgagtga (SEQ ID NO: 2)
MSSVIADSQQPAVSEENANKIILDEEKAVIQCNERYKTENDEKGDEETVS

WCRKAAKSGNAEAQYLFGMLVYDGRGVQQDNCVAMLWWMKAAEQNHAKAL

VMLGNLHRKGQCIAENYPKAIAYWKRAAVQNNVWAYHNLGTAYYDGIGVD

KNPHEAVRWWKKAAELGFPESQNNLGALYNDGNGVDRDYQEAVFWYRKSA

LQGDELGQYNLGVAYYYGRGIKKDFSEAVSWYKKSAEQDYAQAQHNLGVT

YYEGEGIKKDYAKAVYWWKKAAEQGIPQSQYNLGIAYEEGWGAEKNPENA

VFWYRKAAEQGHADAQNRLGIAYRYGTGVRKNPALSVKWLEKAAKQGLAR

AQFNLGKTFYIGAGINKNTDKAVYWFIKAANQGFTEAQAYIGMIYFKGKY

VAKNEKKGFYWLKKAAEKDSAKAQAFLGALYIAGNEVKPNIKEGVALTKK

AALQGNYEAQTLLGFCYENGLEVKKDLIAAYALYLSASPHFDFAEKARLD
LERKLSEQEIAKAISVNTAKLFE

Sel1 318

(SEQ ID NO: 3)
atgaaaagacgggttttgtatggtgtgctgtttgcggtgctggcggggtg
ttctgccggtgcgttggcgtccgtgtccggcttgtcggatgggctggcgc
agcttgaacggaggcagttcgaatcggcttatgcgacgctcatgccggag
gcggagaaggggaatccccgtgcggcgctggaggtggggaagctgctgtt
gacggggcgcggggtggcaaaggatgaagcggcggcggtgaagtggcttc
tggtggcggcggatagtggcaaccgggatgcgcagtatatgctgggggcg
atgtcggtggaggggatcggtctgccgaaggattctcaggtggcgttgac
ctggctgtcgaaggcggcggcgcaggggatgcgcgtgcgaagacggctt
tggggattctgatgcagtccgccgggccgggatcgcagcatacggaacag
gcagcccggtggttcgagaggcggcggcgtcaggggaaccggaggcgca
acggcgctgggcgctgatgctggcgtctggccggggggggccaaaaatga
gggtgaggcactgaaatggtttaagaaggcggctgtcgcggggatgtgg
aagcgcagcgcaatctggggattatgctctcgacgggaaggggtgacg
gcggcaagccggattttgcggaagcggcacgctggtacggcctggcagc
gaagaaggggatgcgaaggcgcagtatgggttgggcattttgtatgcga
aggggcaggggtggcgcccgatcaggaaaaggcgctgattctgtatcgc
atggcggcgactcaggggctggcgacggcggagtatgccgtcgggctggc
gtatgcgtatggacggggacggcacaaaatgatgtgaaggcggccgact
ggttcgaggcggcggcgcagcaggggtggtgcgtgcgcaatataatctc
gctctgatgctggaggcgggtcgcggtcggcctgtggatacggtggcggc
gagcaagtggttttttgatggcggcggagaagggcttgcgggaggcacaat
acaatatgggggtatcactatgccgaggggaaaggggtgccacgcgatcag
ggcaaggcggtgttctggtatgaaaaggcggcggctgccggggatgtgaa
ggcccagtacaatctggggatgctgtatctgaacgggggttaatggcaagg
cggatgacgaaaaggcggcttttttctaccggatggcggccggggcggga
tatggcccggcgatgtaccggctggcggtgttgtatgaggaaggccgtgg
ggtaaagcagagttatcagctggcaggggaatggtatgagcgggcggatc
tggccgcgaaagtgaagattgacgaggcgatgaaaaagaatccgcatccg
tttgtgcaacggactctgcaggtgccggatgatttgaatcaatcttcaga
taaattggcgggacattag (SEQ ID NO: 4)
MKRRVLYGVLFAVLAGCSAGALASVSGLSDGLAQLERRQFESAYATLMPE
AEKGNPRAALEVGKLLLTGRGVAKDEAAAVKWLLVAADSGNRDAQYMLGA
MSVEGIGLPKDSQVALTWLSKAAAQGDARAKTALGILMQSAGPGSQHTEQ
AARWFERAAASGEPEAQRRWALMLASGRGVAKNEGEALKWFKKAAVAGDV
EAQRNLGIMLSTGKGVTGGKPDFAEAARWYGLAAKKGDAKAQYGLGILYA
KGQGVAPDQEKALILYRMAATQGLATAEYAVGLAYAYGRGTAQNDVKAAD
WFEAAAQQGVVRAQYNLALMLEAGRGRPVDTVAASKWFLMAAEKGLREAQ
YNMGYHYAEGKGVPRDQGKAVFWYEKAAAAGDVKAQYNLGMLYLNGVNGK
ADDEKAAFFYRMAAGAGYGPAMYRLAVLYEEGRGVKQSYQLAGEWYERAD
LAAKVKIDEAMKKNPHPFVQRTLQVPDDLNQSSDKLAGH

---

The invention claimed is:

1. A method of stimulating oxalate transport comprising administering to a subject a pharmaceutical composition comprising a suppressor-enhancer of lin 1 (Sel1)-derived peptide, wherein the Sel1-derived peptide comprises (i) the amino acid sequence of SEQ ID NO: 52 or 53 or (ii) the amino acid sequence that is at least 90% identical to SEQ ID NO: 12 or 13, and wherein the Sel1-derived peptide is no more than about 50 amino acids in length.

2. The method of claim 1, wherein the administration is rectal administration, oral administration, or injection.

3. The method of claim 1, wherein the subject suffers from or is at risk for hyperoxaluria and/or hyperoxalemia.

4. The method of claim 1, wherein the subject's risk of calcium oxalate kidney stones, nephrocalcinosis, oxalate nephropathy, end stage renal disease, chronic kidney disease, and/or systemic oxalosis is lowered by the administration.

5. The method of claim 1, wherein the Sel1-derived peptide comprises the amino acid sequence that is at least 90% identical to SEQ ID NO: 12 or 13.

6. The method of claim 1, wherein the Sel1-derived peptide comprises the amino acid sequence of SEQ ID NO: 52 or 53.

7. The method of claim 1, wherein the composition comprises 2 or more of the Sel1-derived peptides.

8. The method of claim 7, wherein the two or more Sel1-derived peptides are fused directly or indirectly to each other.

9. The method of claim 7, wherein the two or more Sel1-derived peptides are not fused to each other.

10. The method of claim 1, wherein:
(i) the Sel1-derived peptide comprises one or more D enantiomers,
(ii) the Sel1-derived peptide comprises one or more unnatural amino acids,
(iii) the Sel1-derived peptide comprises one or more amino acid analogs, and/or
(iv) the Sel1-derived peptide comprises one or more peptoid amino acids.

11. The method of claim 1, wherein the Sel1-derived peptide comprises a modification selected from the group consisting of phosphorylation, glycosylation, ubiquitination, S-nitrosylation, methylation, N-acetylation, C-terminal amidation, cyclization, substitution of natural L-amino acids with non-natural D-amino acids, lipidation, lipoylation, deimination, eliminylation, disulfide bridging, isoaspartate formation, racemization, glycation, carbamylation, carbonylation, isopeptide bond formation, sulfation, succinylation, S-sulfonylation, S-sulfinylation, S-sulfenylation, S-glutathionylation, pyroglutamate formation, propionylation, adenylylation, nucleotide addition, iodination, hydroxylation, malonylation, butyrylation, amidation, alkylation, acylation, biotinylation, carbamylation, oxidation, and pegylation.

12. The method of claim 1, wherein the pharmaceutical composition further comprises a pharmaceutically acceptable carrier.

13. The method of claim 12, wherein the pharmaceutical composition further comprises one or more additional therapeutic agents.

* * * * *